United States Patent
Serda et al.

(10) Patent No.: US 12,201,651 B2
(45) Date of Patent: Jan. 21, 2025

(54) SILICIFIED IMMUNOGENIC CELLS, METHODS OF MAKING, AND METHODS OF USING

(71) Applicant: UNM RAINFOREST INNOVATIONS, Albuquerque, NM (US)

(72) Inventors: Rita E. Serda, Albuquerque, NM (US); Jimin Guo, Albuquerque, NM (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 181 days.

(21) Appl. No.: 17/436,872

(22) PCT Filed: Mar. 3, 2020

(86) PCT No.: PCT/US2020/020776
§ 371 (c)(1),
(2) Date: Sep. 7, 2021

(87) PCT Pub. No.: WO2020/185449
PCT Pub. Date: Sep. 17, 2020

(65) Prior Publication Data
US 2022/0125835 A1 Apr. 28, 2022

Related U.S. Application Data

(60) Provisional application No. 62/815,521, filed on Mar. 8, 2019.

(51) Int. Cl.
*A61K 35/13* (2015.01)
*C12N 5/00* (2006.01)
*C12N 5/09* (2010.01)

(52) U.S. Cl.
CPC ............ *A61K 35/13* (2013.01); *C12N 5/0012* (2013.01); *C12N 5/0068* (2013.01); *C12N 5/0693* (2013.01); *C12N 2501/15* (2013.01); *C12N 2501/231* (2013.01); *C12N 2533/10* (2013.01); *C12N 2533/32* (2013.01); *C12N 2533/72* (2013.01)

(58) Field of Classification Search
CPC ...... A61K 35/13; A61K 35/12; C12N 5/0012; C12N 5/0068; C12N 5/0693; C12N 2501/15; C12N 2501/231; C12N 2533/10; C12N 2533/32; C12N 2533/72
See application file for complete search history.

(56) References Cited

U.S. PATENT DOCUMENTS

| | | |
|---|---|---|
| 6,294,177 B1 | 9/2001 | Fattom |
| 2004/0191229 A1 | 9/2004 | Link, Jr. et al. |
| 2009/0181078 A1 | 7/2009 | Reed et al. |
| 2014/0363872 A1 | 12/2014 | Jaroch et al. |
| 2020/0276286 A1 | 9/2020 | Serda et al. |

FOREIGN PATENT DOCUMENTS

| | | | |
|---|---|---|---|
| WO | WO-2014121132 A1 * | 8/2014 | ............ A61K 39/12 |
| WO | 2019055620 A1 | 3/2019 | |
| WO | 2020185449 A1 | 9/2020 | |
| WO | 2022132817 A1 | 6/2022 | |

OTHER PUBLICATIONS

Kim et al., Intra-mitochondrial biomineralization for inducing apoptosis of cancer cells, Chem. Sci., 2018, 9, 2474; DOI: 10.1039/c7sc05189a (Year: 2018).*
Serrano et al., Liposomal vaccine formulations as prophylactic agents: design considerations for modern vaccines; J Nanobiotechnol (2017) 15:83; DOI 10.1186/s12951-017-0319-9 (Year: 2017).*
Kröger, N., Deutzmann, R., Bergsdorf, C. and Sumper, M., 2000. Species-specific polyamines from diatoms control silica morphology. Proceedings of the National Academy of Sciences, 97(26), pp. 14133-14138. (Year: 2000).*
De Serrano, L.O. and Burkhart, D.J., 2017. Liposomal vaccine formulations as prophylactic agents: design considerations for modern vaccines. Journal of nanobiotechnology, 15(1), pp. 1-23. (Year: 2017).*
Kim, S., Palanikumar, L., Choi, H., Jeena, M.T., Kim, C. and Ryu, J.H., 2018. Intra-mitochondrial biomineralization for inducing apoptosis of cancer cells. Chemical science, 9(9), pp. 2474-2479. (Year: 2018).*
Rothenfusser, S., Tuma, E., Endres, S. and Hartmann, G., 2002. Plasmacytoid dendritic cells: the key to CpG. Human immunology, 63(12), pp. 1111-1119. (Year: 2002).*
Chiang et al., "Whole Tumor Antigen Vaccines: Where Are We?," Vaccines, 2015, vol. 3, pp. 344-372.
Flies et al., "PD-L1 Is Not Constitutively Expressed on Tasmanian Devil Facial Tumor Cells but Is Strongly Upregulated in Response to IFN-γ and Can Be Expressed in the Tumor Microenvironment," Frontiers in Immunology, Dec. 2016, vol. 7, No. 581, pp. 1-13.
Hamm et al., "Architecture and material properties of diatom shells provide effective mechanical protection," Nature, Feb. 20, 2003, vol. 421, pp. 841-843.
Hanna, M., "Immunotherapy with autologous tumor cell vaccines for treatment of occult disease in early stage colon cancer," Human Vaccines & Immunotherapeutics, Aug. 2012, vol. 8, No. 8, pp. 1156-1160.

(Continued)

*Primary Examiner* — Christopher M Babic
*Assistant Examiner* — Masudur Rahman
(74) *Attorney, Agent, or Firm* — MUETING RAASCH GROUP

(57) ABSTRACT

A pharmaceutical composition includes a silicified cell or fraction thereof, a cationic layer disposed on at least a portion of the surface of the silicified cell or fraction thereof, and an immunomodulatory moiety bound to at least a portion of the cationic layer. Alternatively, the pharmaceutical composition includes a silicified cell or fraction thereof, a cationic layer disposed on at least a portion of the surface of the silicified cell or fraction thereof, an anionic layer disposed on at least a portion of the cationic layer, and an immunomodulatory moiety bound to at least a portion of the anionic layer.

15 Claims, 46 Drawing Sheets

Specification includes a Sequence Listing.

(56) References Cited

OTHER PUBLICATIONS

Higuchi et al., "CTLA-4 Blockade Synergizes Therapeutically with PARP Inhibition in BRCA1-Deficient Ovarian Cancer," Cancer Immunology Research, Nov. 2015, vol. 3, No. 11, pp. 1257-1268.
International Preliminary Report on Patentability for PCT/US2018/050831, issued Mar. 17, 2020, 5 pages.
International Preliminary Report on Patentability for PCT/US2020/020776, issued Aug. 25, 2021, 7 pages.
International Preliminary Report on Patentability for PCT/US2021/063386, issued Jun. 13, 2023, 7 pages.
International Search Report and Written Opinion for PCT/US2018/050831, issued Dec. 20, 2018, 6 pages.
International Search Report and Written Opinion for PCT/US2020/020776, issued May 28, 2020, 7 pages.
International Search Report and Written Opinion for PCT/US2021/063386, issued Mar. 10, 2022, 10 pages.
Kaehr et al., "Cellular complexity captured in durable silica biocomposites," PNAS, Oct. 23, 2012, vol. 109, No. 43, pp. 17336-17341.
Koster et al., "Autologous tumor cell vaccination combined with systemic CpG-B and IFN-α promotes immune activation and induces clinical responses in patients with metastatic renal cell carcinoma: a phase II trial," Cancer Immunology, Immunotherapy, 2019, vol. 68, pp. 1025-1035.
Kurtz et al., "Current Status of Autologous Breast Tumor Cell-based Vaccines," Expert Review of Vaccines, Dec. 2014, vol. 13, No. 12, pp. 1439-1445.
Lou et al., "Silica bioreplication preserves three-dimensional spheroid structures of human pluripotent stem cells and HepG2 cells," Scientific Reports, Sep. 1, 2015, vol. 5, No. 13635, pp. 1-9.
Radford et al., "A recombinant *E.coli* vaccine to promote MHC class I-dependent antigen presentation: application to cancer immunotherapy," Gene Therapy, 2002, vol. 9, pp. 1455-1463.
Rhodes et al., "Using vaccine Immunostimulation/Immunodynamic modelling methods to inform vaccine dose decision-making," npj Vaccines, Sep. 17, 2018, vol. 3, No. 36, pp. 1-7.
Roby et al., "Development of a syngeneic mouse model for events related to ovarian cancer," Carcinogenesis, 2000, vol. 21, No. 4, pp. 585-591.
Serda et al., "The association of silicon microparticles with endothelial cells in drug delivery to the vasculature," Biomaterials, 2009, vol. 30, pp. 2440-2448.
Srivatsan et al., "Allogeneic tumor cell vaccines: The promise and limitations in clinical trials," Human Vaccines & Immunotherapeutics, Jan. 2014, vol. 10, pp. 52-63.
Sumper et al., "Silica Biomineralization in Diatoms: The Model Organism Thalassiosira pseudonana," Chembiochem, 2008, vol. 9, pp. 1187-1194.
The Cancer Genome Atlas Research Network, "Integrated Genomic Analyses of Ovarian Carcinoma," Nature, Dec. 30, 2011, vol. 474, No. 7353, pp. 609-615.
Utaisincharoen et al., "Kinetic studies of the production of nitric oxide (NO) and tumour necrosis factor-alpha (TNF-α) in macrophages stimulated with Burkholderia pseudomallei endotoxin," Clinical & Experimental Immunology, 2000, vol. 122, pp. 324-329.
Vacchelli et al., "Trial watch: FDA-approved Toll-like receptor agonists for cancer therapy," Oncoimmunology, Sep. 2012, vol. 1, No. 6, pp. 894-907.
Walker et al., "Geobiology of a microbial endolithic community in the Yellowstone geothermal environment," Nature, Apr. 21, 2005, vol. 434, pp. 1011-1014.
Wang et al., "Hydrated Silica Exterior Produced by Biomimetic Silicification Confers Viral Vaccine Heat-Resistance," ACS Nano, 2015, vol. 9, No. 1, pp. 799-808.
Wang et al., "Immunogenic effects of chemotherapy-induced tumor cell death," Genes & Diseases, 2018, vol. 5, pp. 194-203.
Xing et al., "A Mouse Model for the Molecular Characterization of Brca1-Associated Ovarian Carcinoma," Cancer Research, Sep. 15, 2006, vol. 66, No. 18, pp. 8949-8953.

\* cited by examiner

Fig. 13A   Si-PEI-CPG-MPL cell (mass ratio)
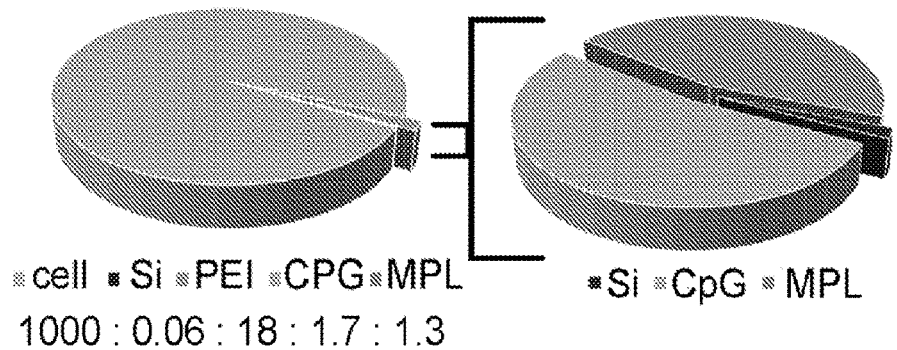
cell : Si : PEI : CPG : MPL
1000 : 0.06 : 18 : 1.7 : 1.3
Fig. 13B
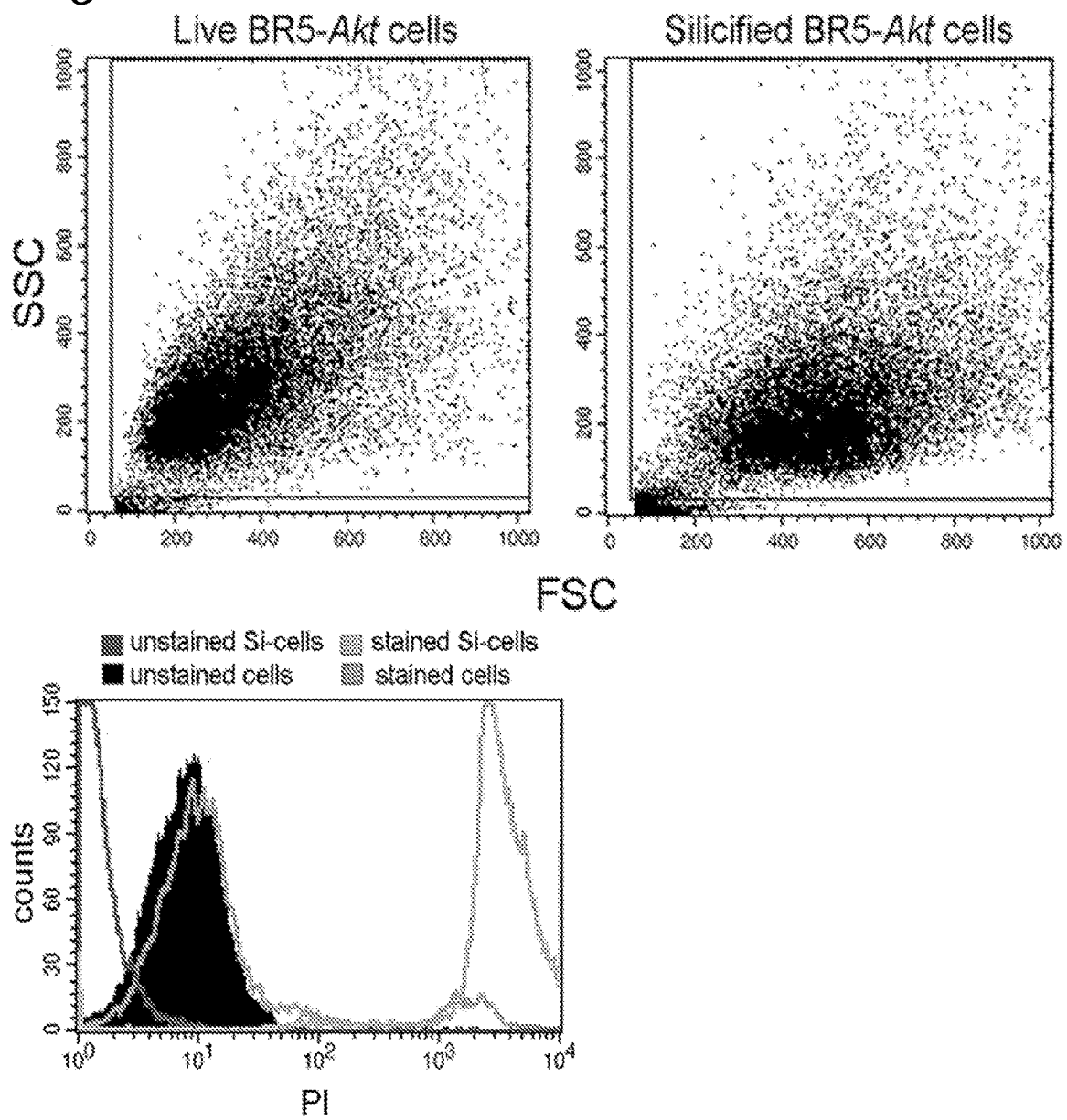

Fig. 17B-1
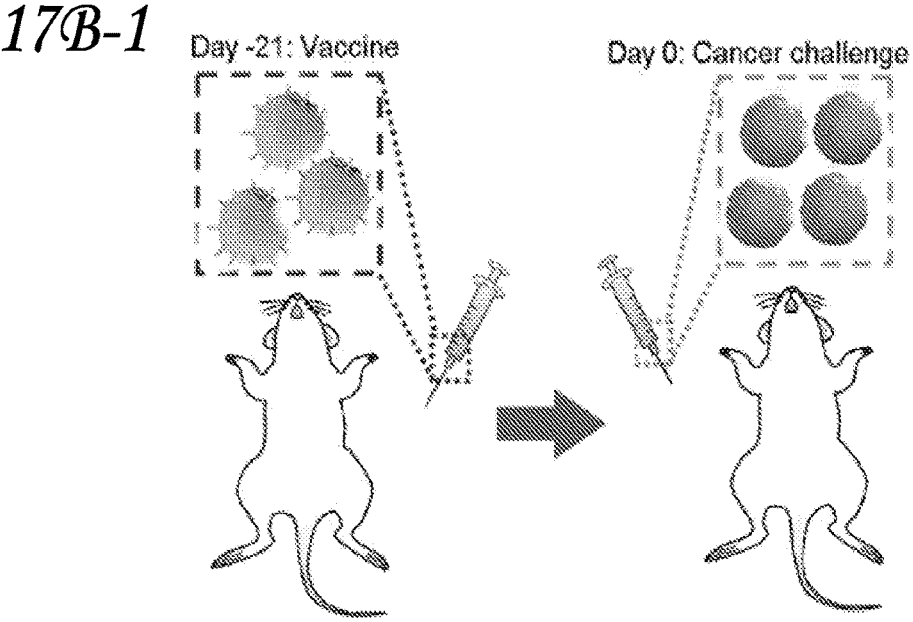
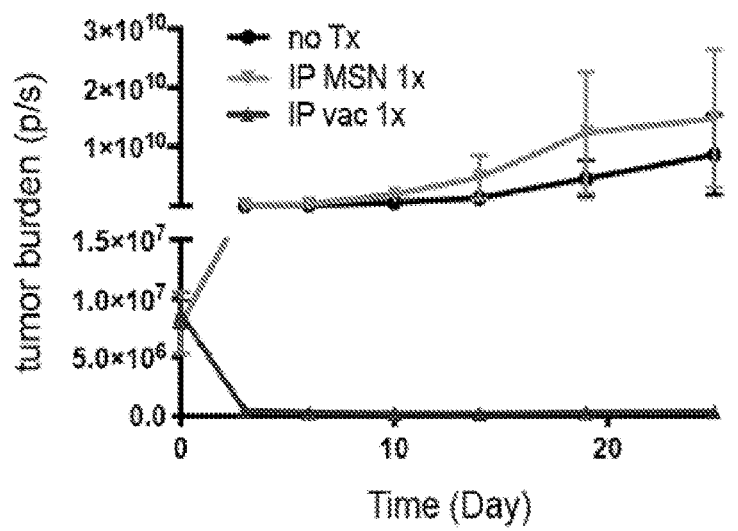
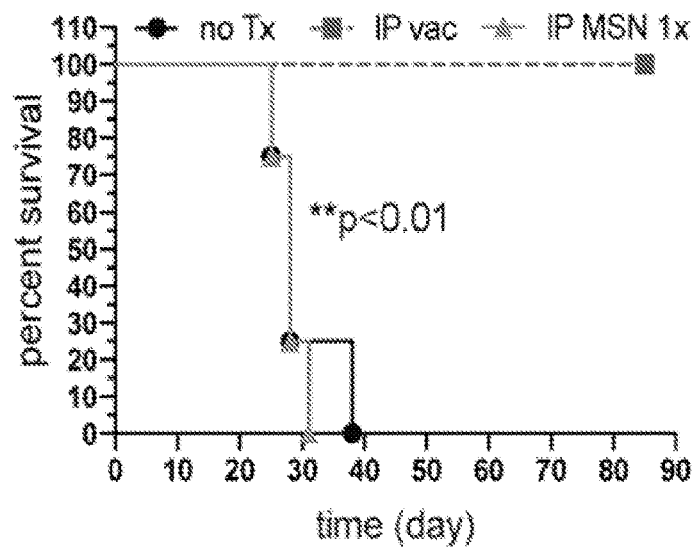

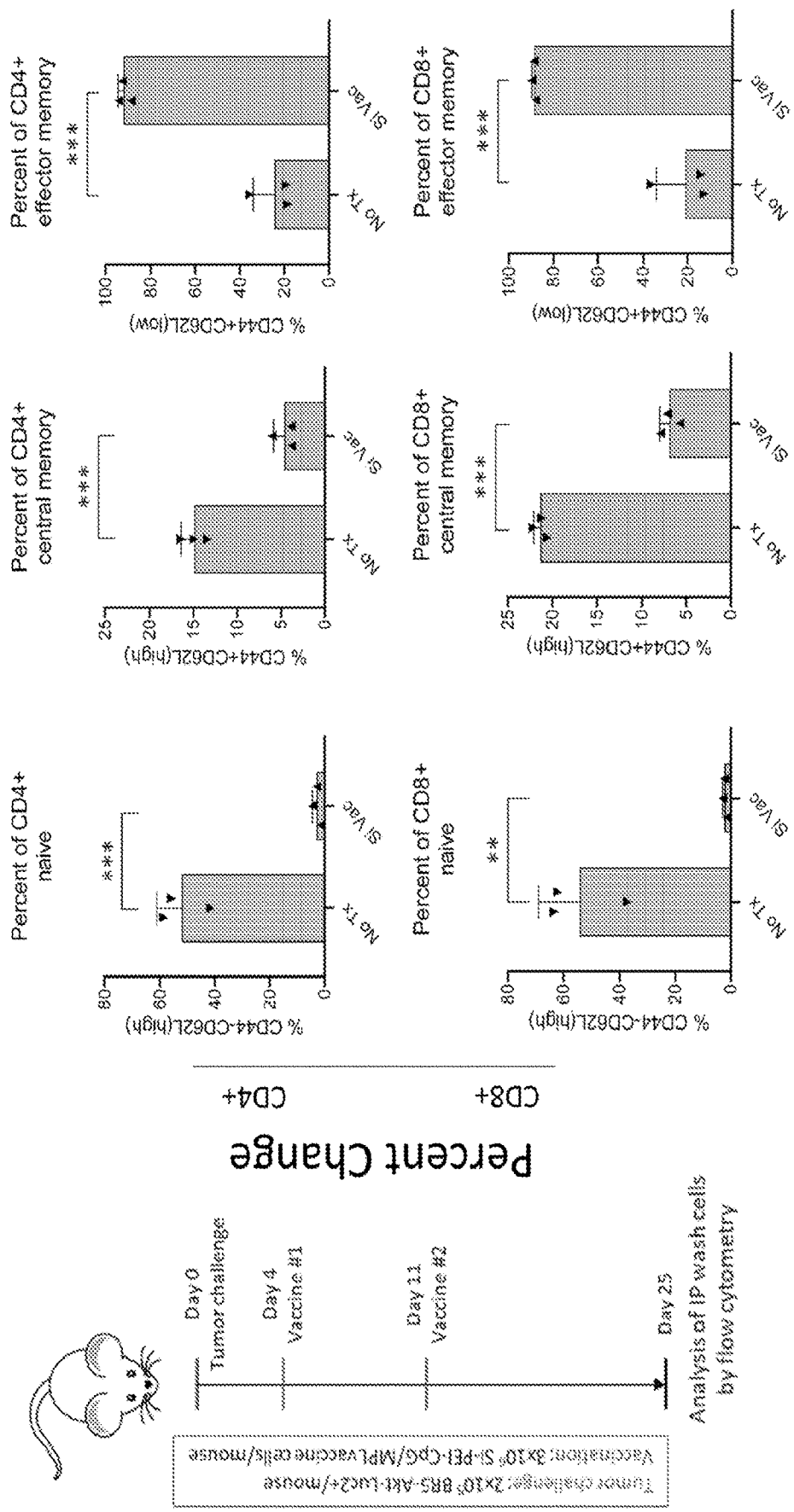

SEQUENCE LISTING

<160> NUMBER OF SEQ ID NOS: 1

<210> SEQ ID NO 1
<211> LENGTH: 8
<212> TYPE: PRT
<213> ORGANISM: artificial
<220> FEATURE:
<223> OTHER INFORMATION: Polypeptide

<400> SEQUENCE: 1

Ser Ile Ile Asn Phe Glu Lys Leu
1               5

SILICIFIED IMMUNOGENIC CELLS, METHODS OF MAKING, AND METHODS OF USING

CROSS-REFERENCE TO RELATED APPLICATION

This application is the § 371 U.S. National Stage of International Application No. PCT/US2020/020776, filed Mar. 3, 2020, which claims the benefit of U.S. Provisional Patent Application No. 62/815,521, filed Mar. 8, 2019, each of which is incorporated herein by reference in its entirety.

SEQUENCE LISTING

This application contains a Sequence Listing electronically submitted via EFS-Web to the United States Patent and Trademark Office as an ASCII text file entitled "03100147WO01_ST25.txt" having a size of 443 bytes and created on Mar. 3, 2020. The 15 information contained in the Sequence Listing is incorporated by reference herein.

SUMMARY

This disclosure describes, in one aspect, a pharmaceutical composition that includes a silicified cell or fraction thereof that is surface modified to present an immunomodulatory moiety.

In some embodiments, the silicified cell includes a cationic layer disposed on at least a portion of the surface of the silicified cell and an immunomodulatory moiety bound to at least a portion of the cationic layer.

In some embodiments, the silicified cell includes a cationic layer disposed on at least a portion of the surface of the silicified cell, an anionic layer disposed on at least a portion of the cationic layer, and an immunomodulatory moiety bound to at least a portion of the anionic layer.

In some embodiments, the immunomodulatory moiety can include a pathogen-associated molecular pattern (PAMP), a danger-associated molecular molecule (DAMP), a cytokine, an antibody, or other immunogenic entity. In some of these embodiments, the PAMP can include lipopolysaccharide (LPS), monophosphoryl lipid A (MPL), CpG, R-848, or PolyIC.

In another aspect, this disclosure describes a method of inducing an immune response against an immunogenic silicified cell. Generally, the method includes silicifying the cell, and administering the immunogenic silicified cell to a subject in an amount effective to induce the subject to produce an immune response directed against the immunogenic silicified cell.

In some embodiments, the immunogenic silicified cell is administered to the subject in a composition that comprises an effective amount of a pharmaceutically acceptable adjuvant.

In some embodiments, the immunogenic silicified cell is administered to the subject in a composition that includes an agent that blocks immune suppression. In some of these embodiments, the agent that blocks immune suppression can include an anti-TGF-β antibody or an anti-IL-10 antibody. In other embodiments, the agent that blocks immune suppression can include an immune checkpoint inhibitor.

In another aspect, this disclosure describes a method for treating a subject having, or at risk of having, a tumor. Generally the method includes obtaining a tumor cell that the subject has or is at risk of having, silicifying the tumor cell, and administering the silicified tumor cell to the subject in an amount effective to ameliorate at least one symptom or clinical sign of having the tumor.

In some embodiments, the tumor cell is an autologous cancer cell obtained from the subject. In some of these embodiments, the tumor cell can be obtained from ascites fluid. In other embodiments, the tumor cell can be obtained from a solid tumor, at least a portion of which is removed from the subject.

In some embodiments, the tumor cell can be an allogenic cancer cell obtained a second subject.

In some embodiments, the silicified cell is administered to the subject in a composition that includes an effective amount of a pharmaceutically acceptable adjuvant.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 13. Silicified cell characterization. (A) Pie charts showing Si-PEI-CpG-MPL cell composition by mass ratio. (B) Flow cytometry scatter dot plots of live or silicified BR5-Akt cells showing change in size (FSC) with silicification and histogram of cells before or after staining with propidium iodide (PI) to demonstrate that silicified cells are non-viable.

DETAILED DESCRIPTION OF ILLUSTRATIVE EMBODIMENTS

This disclosure describes a therapeutic vaccine strategy that involves surface modification of a silicified cell to enhance immunogenicity of the silicified cell.

The silicified cell can be any cell type that poses a danger to the host and where an immune response against antigens associated with the cell would benefit the host. This includes cancer cells (autologous or allogenic), pathogenic cells (e.g., microbes), or cells that express antigens associated with cancer (e.g., embryonic cells and cells genetically modified to cause expression of tumor antigens or tumor-associated antigens).

In the context of cancer cells, a silicified tumor cell vaccine can induce in vivo immune-mediated tumor cell clearance and/or effector T cell recruitment. A tumor cell can be mineralized and secondarily decorated with, for example, pathogen-associated molecular patterns (PAMPs). In another aspect, this disclosure describes a silicification strategy whereby the process is carried out at −80° C. Modification of the silicified cells with cationic molecules, anionic molecules, and/or hydrophobic molecules that enhance binding of immunogens (e.g., PAMPs, small molecules, adjuvants) to the surface of the silicified cell.

Many solid tumors can be treated by engaging the immune system. These approaches include the development of tumor vaccines, including whole cancer cell vaccines using allogeneic cell lines and autologous tumor cells. Despite evidence that certain cancers—e.g., ovarian cancer—are strong candidates for immune therapy, single agent immune interventions have underperformed clinically. This may be due, at least in part, to tumors creating a highly immune suppressive microenvironment and/or the lack of a universally expressed tumor antigen. The therapeutic vaccine strategy described herein overcomes some of the challenges that have caused conventional single agent immune interventions to underperform clinically.

Figure 1:
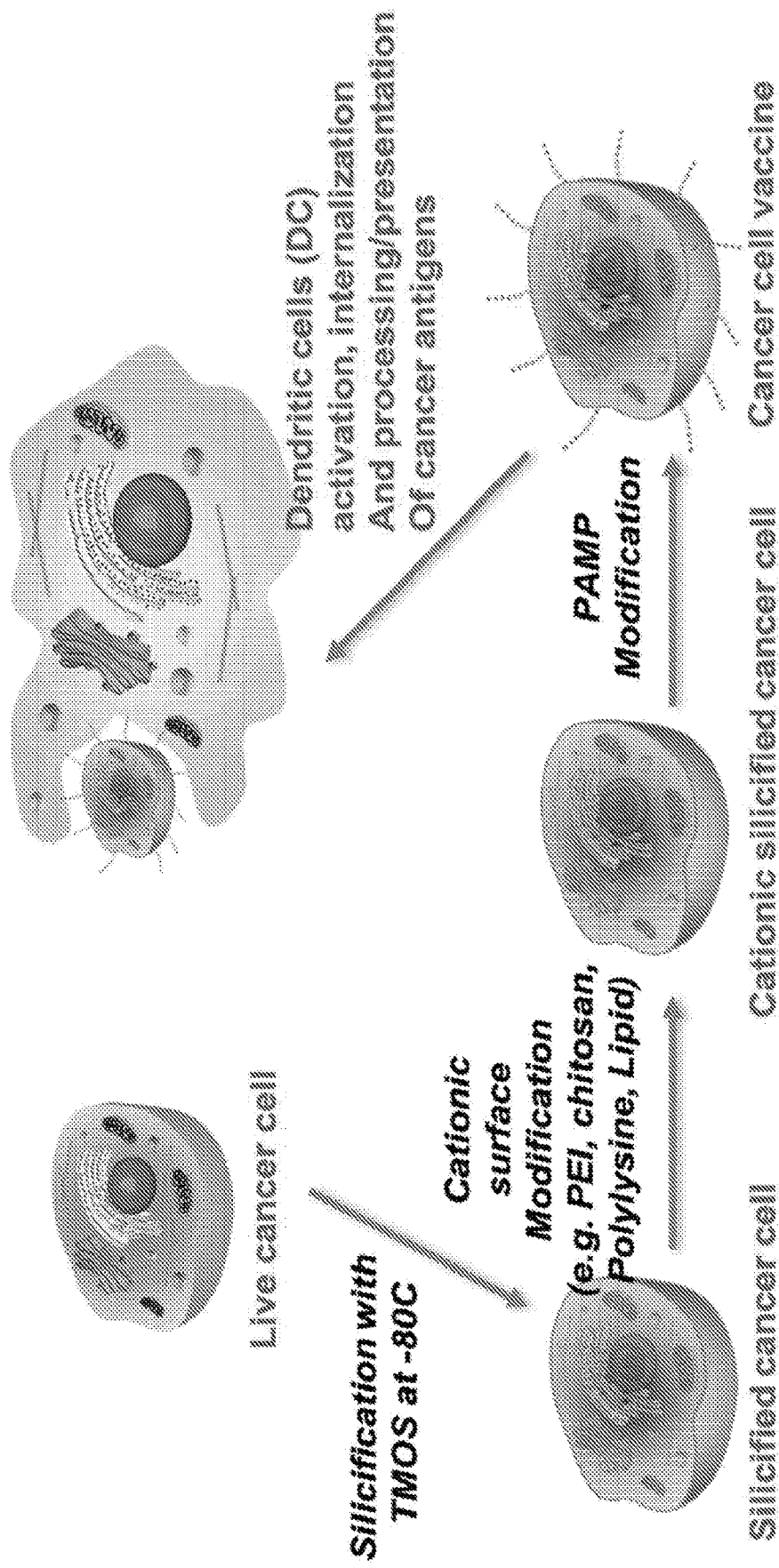
FIG. 1. Pathogen mimic cancer cell vaccine. This schematic shows silicification of cancer cells with TMOS at −80° C. The highly adsorbent silicified cancer cell is then modified with a secondary substance to tailor the surface to the chosen immunogenic ligand. Here we coat the silicified surface with cationic molecules (e.g. PEI, chitosan, polylysine or lipid). The cationic cell surface then robustly binds to immunogenic ligands (e.g., PAMPs, DAMPs, antibodies, cytokines, small molecules). The ligands enable binding to and activation of antigen presenting cells, which internalize the cancer cells, process and present antigens to T cells for elimination of cancer cells.
Figure 2A:
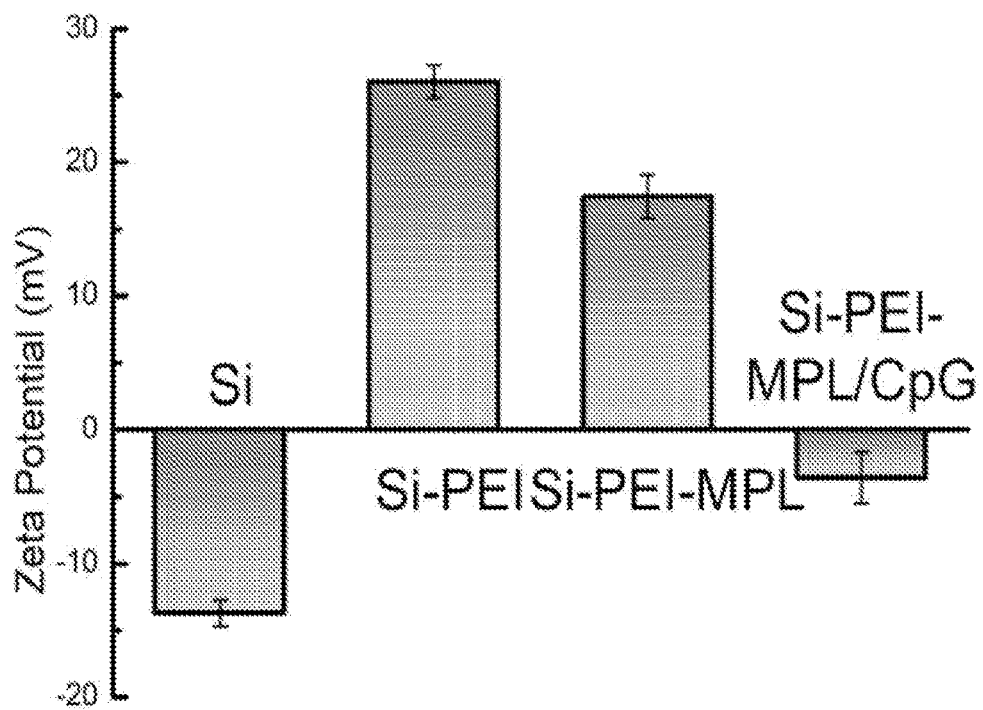
FIG. 2. Characterization of cell surface modifications. (A) cell surface charge (zeta potential) of silicified cancer cells (Si), PEI coated Si cells (Si-PEI), monophosphoryl lipid A (MPL)-coated Si PEI cells (Si-PEI-MPL) and MPL/CpG coated Si cells (Si-PEI-MPL/CpG. (B) Si-cells coated with chitosan (Si-CHI), and then coated with MPL or MPL (Si-CHI-MPL) and CpG (Si-CHI-MPL/CpG). (C) Silicified cell surface charge (Zeta potential) after incubation with 0-1 mg/ml PEI. (D) LPS binding as a function of cancer cell surface charge.
Figure 2B:
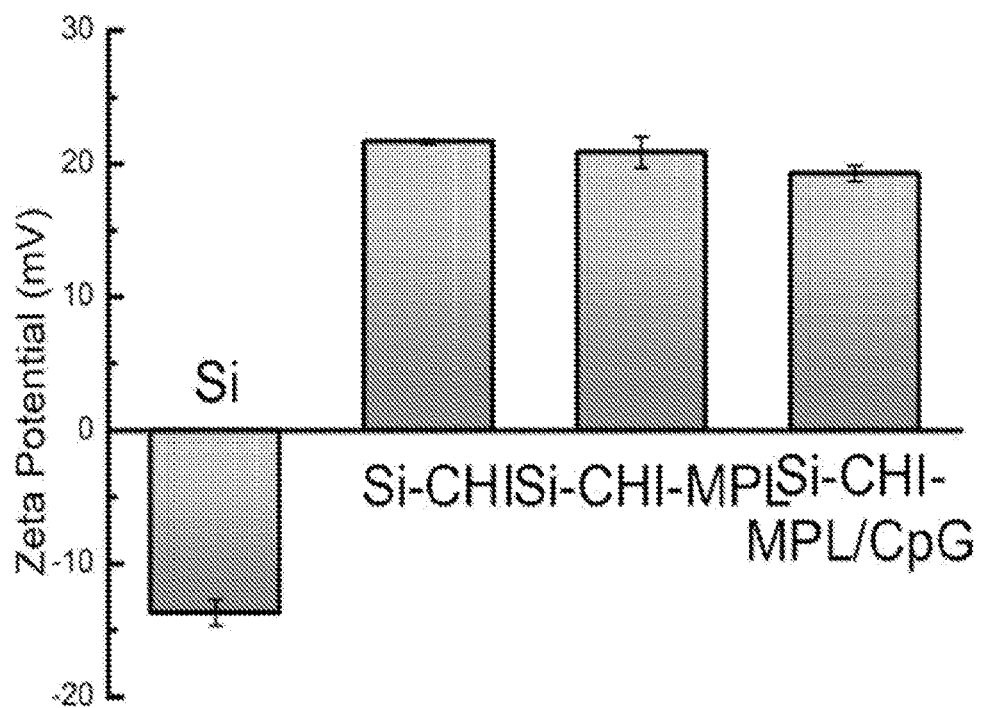
Figure 2C:
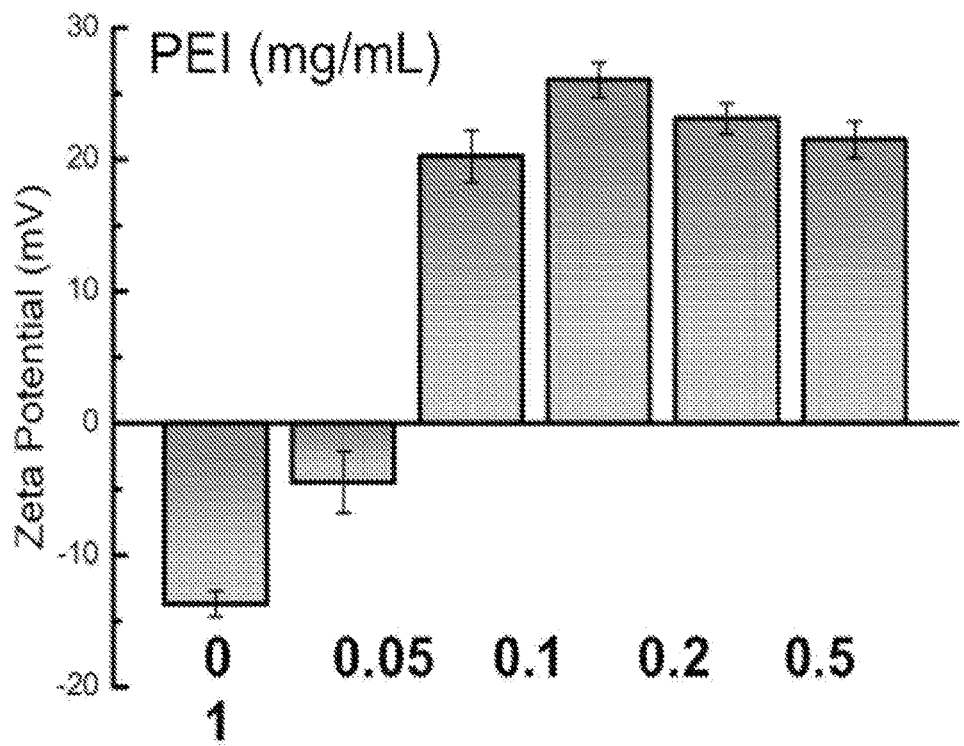
Figure 2D:
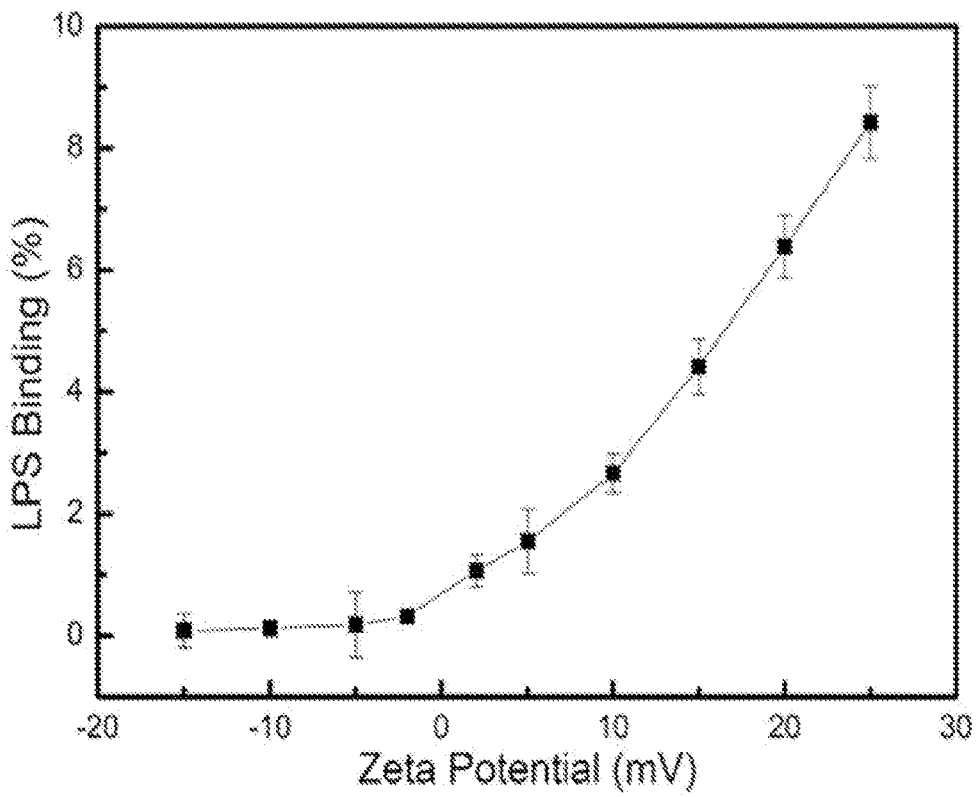
Figure 3A:
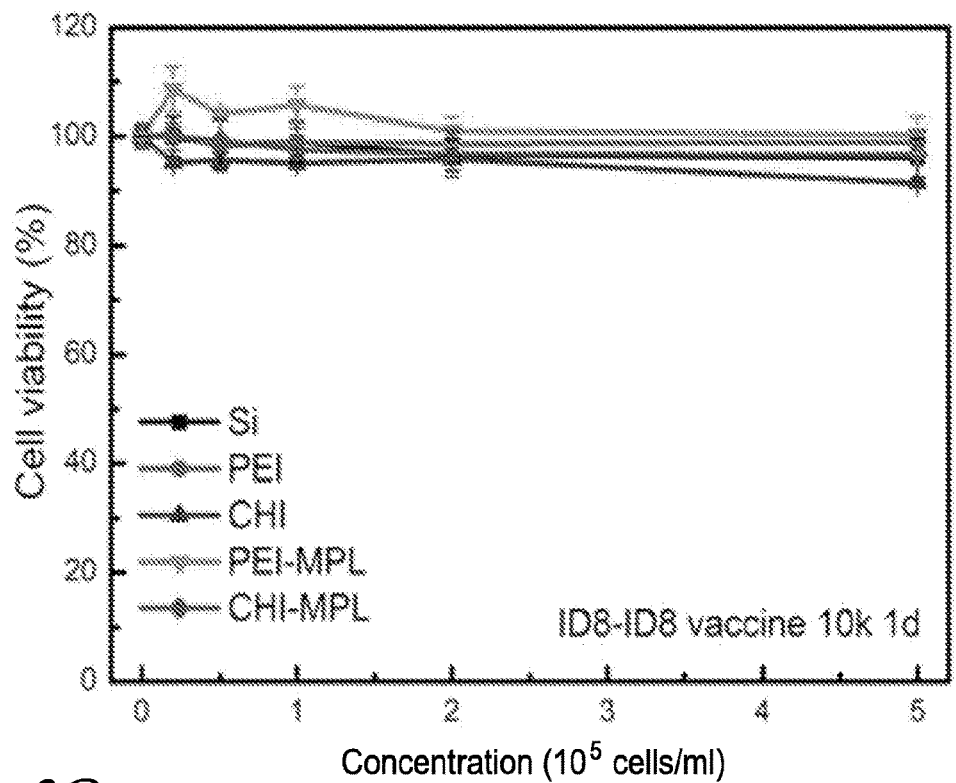
FIG. 3. Biocompatibility of cationic cancer cells. (A) Viability of ID8 cancer cells following incubation with increasing concentrations of silicified, surface functionalized cancer cells for 24 hours. Silicified cancer cells were modified using PEI or chitosan (CHI), followed by MPL. (B) Viability of BR5-Akt cancer cells following incubation with increasing concentrations of silicified, surface functionalized cancer cells for 24 hours. Silicified cancer cells were modified using PEI or chitosan (CHI), followed by MPL. (C) Viability of bone marrow-derived dendritic cells (BMDC) following 24 hours incubation with increasing concentrations of silicified cancer cells. (D) Viability of bone marrow-derived dendritic cells (BMDC) following 72 hours incubation with increasing concentrations of silicified cancer cells. Extended incubation of BMDC with high concentrations of chitosan-coated cancer cells reduced viability by 25%.
Figure 3B:
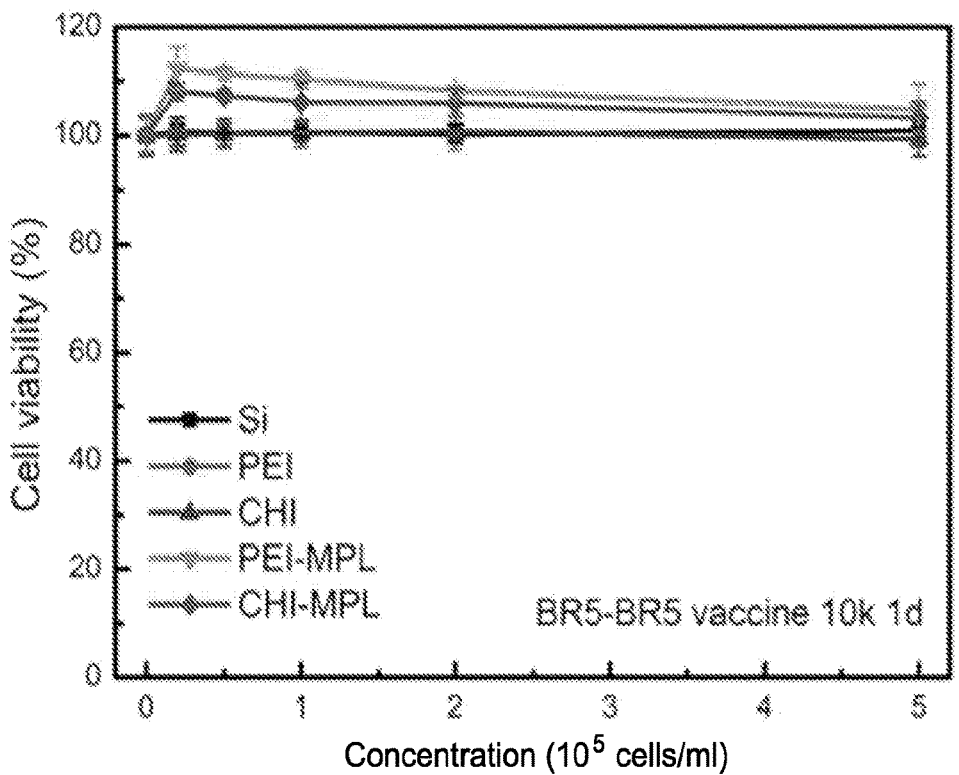
Figure 3C:
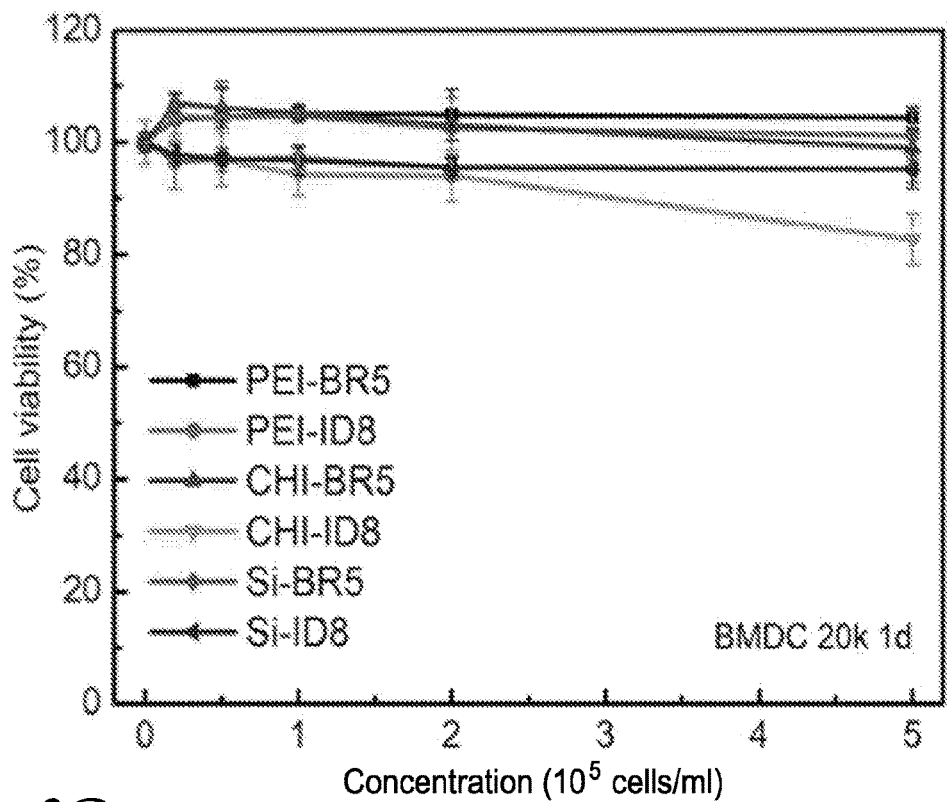
Figure 3D:
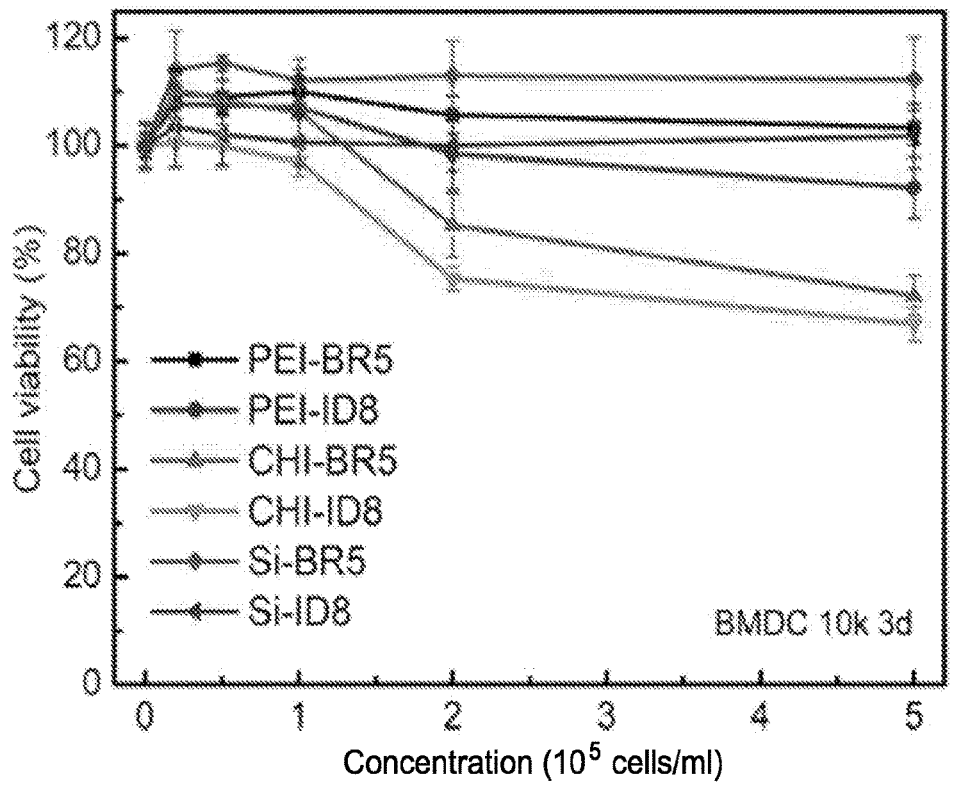

The vaccine strategy described herein involves binding immunogens to the surface of an immunogenic silicified cell, creating a cell mimic with enhanced immunogenicity compared to a non-silicified cell. FIG. 1 illustrates a process of silicifying (e.g., biomineralizing) cancer cells. In the illustrated exemplary embodiment, the silicified cells are preserved and become functionalized, enabling surface modification with pathogen associated molecules. The "pathogen mimics" function as vaccines, attracting and activating immune cells to process and present tumor antigens to T cells to eradicate tumors. Cell silicification in the illustrated exemplary embodiment is performed by immersing cells in an acidic TMOS solution and incubating the cells at −80° C. for self-limiting silicification of the cancer cells.

The type of secondary modification can be tailored to the chosen immunogenic ligand selected for presentation on the surface of the silicified cell surface. Thus, for example, modifying a silicified cancer cell surface with polyethyleneimine (PEI), chitosan, poly(L-lysine), poly(γ-glutamic acid), cationic lipid, or other cationic molecule increases binding of certain immunogens (e.g., PAMPs, CpG, MPL, LPS) to the silicified cancer cell surface. Alternatively, if the immunogenic molecule that one wishes to bind to the surface of the silicified cell is cationic, one can use an anionic molecule for secondary modification, such as alginate, poly(D-lactic acid), poly(acrylic acid), dextran sulphate, or hyaluronic acid.

Microbial products (PAMPs) stimulate antigen presenting cell (APC) maturation through Toll like receptors (TLR) or other pattern recognition receptors (PRR). Activation of TLR and/or PRR signaling pathways promotes expression of co-stimulatory molecules and cytokines. Monophosphoryl lipid-A (MPL), a nontoxic derivative of lipopolysaccharide (LPS), is a T helper (Th)1-biased adjuvant that binds to surface/endosomal TLR4 on antigen presenting cells and activates a proinflammatory signaling cascade. Adsorption of monophosphoryl lipid A (MPL) to the cell surface enables multivalent activation of antigen presenting cells, enabling cancer cells to both target and activate antigen presenting cells. The ensuing cytokine cascade polarizes macrophages, dendritic cells (DC) and natural killer cells towards a Th1 phenotype. Combinations of TLR agonists can induce synergistic immune activation. Unmethylated bacterial CpG oligonucleotide (ODN) binds to TLR9 present within the endolysosomal compartment, triggering signaling cascades that further stimulate a proinflammatory response. Signaling crosstalk between TLR4 and TLR9 has been shown to amplify immune responses.

While described herein in the context of exemplary embodiments in which the surface-modified silicified cells are decorated with TLR agonists as an exemplary surface functionalization, the compositions and methods described herein can involve silicified cells with surfaces modified so that the silicified cell can be functionalized with any suitable immunomodulatory or therapeutic moiety. The silicified cell surface can bind a broad array of molecules or drugs, presenting diverse opportunities for immunomodulation and targeted therapy. The choice of surface-bound adjuvant could be based on an individual patient's response to treatment or tailored for the immune landscape of a patient's tumor. In addition, the integration of antibodies or molecules that reverse inhibitory pathways in the tumor microenvironment would be expected to sustain the activation of cancer-specific T cells generated in response to the vaccine.

Tumor cell silicification establishes a modular platform for vaccine development. Ex vivo cell silicification of cancer cells as a method of fixation advances vaccine design by preserving cell integrity and the biofunctionality of proteinaceous components, and enabling surface functionalization with, for example, pathogen-associated molecular patterns (PAMPs). By silicifying tumor cells, then decorating the silicified tumor cell with one or more PAMPs, cancer cells are transformed into pathogen (bacteria) mimics.

Preparation and use of immunogenic silicified cells are described in International Patent Application No. PCT/US2018/050831. Alternatively, immunogenic silicified cells can be prepared as described herein. Briefly, cells can be rinsed with a buffer solution such as, for example, PBS and/or a NaCl solution before being suspended in a silicification solution. The silification solution can include an amount of a silica-containing material to silicify the cells. Exemplary suitable silica-containing materials include, but are not limited to, tetramethyl orthosilicate (TMOS); tetraethyl orthosilicate (TEOS); 1,2-bis(trimethoxysilyl)ethane; bis[3-(trimethoxysilyl)propyl]amine; 1,2-bis(triethoxysilyl)ethane; bis[3-(triethoxysilyl)propyl]tetrasulfide; 1,4-bis(triethoxysilyl)benzene; 4,4'-bis(triethoxysilyl)-1,1'-biphenyl; 3-aminopropyltriethoxysilane (APTES); or N-(2-aminoethyl)-3-aminopropyltrimethoxysilane (AAPTS). In some cases, the silification solution can include a combination of two or more silica-containing materials.

Figure 11A:
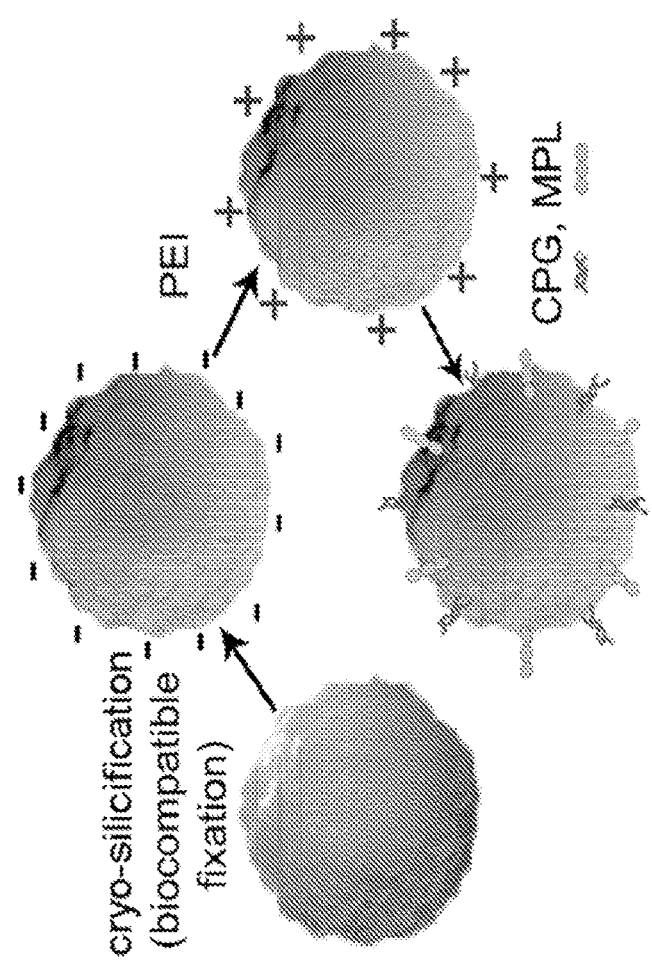
FIG. 11. Silicified cell preparation and characterization. (A) Cancer cells are transformed into bacteria mimetic cells through cryo-silicification and surface masking with PAMPs. (B) Confirmation of Si content in silicified BR5-Akt tumor cells using SEM and energy dispersive X-ray analysis of carbon (C), oxygen (O), and silicon (Si).
Figure 11B:
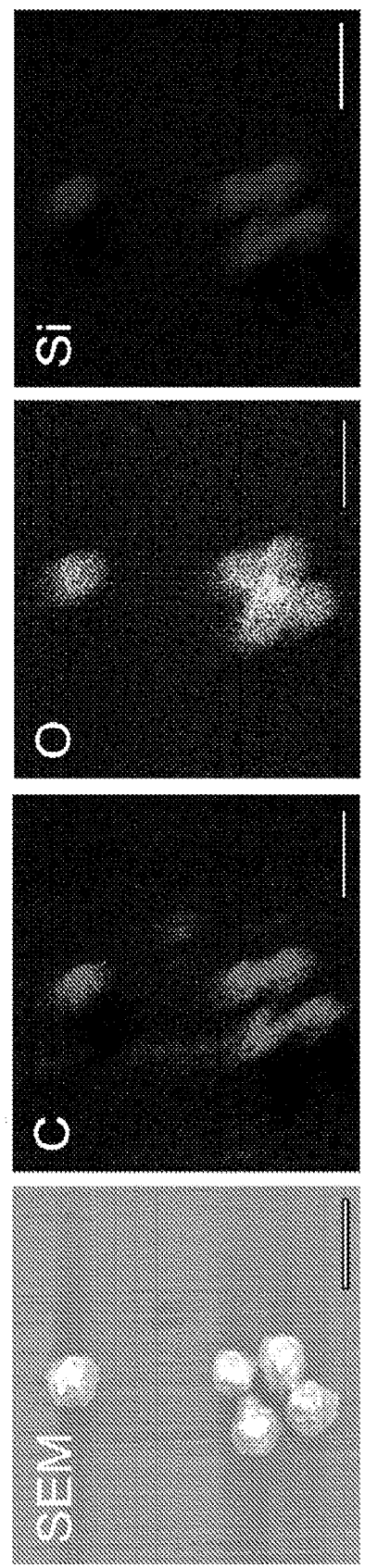
Figure 12A:
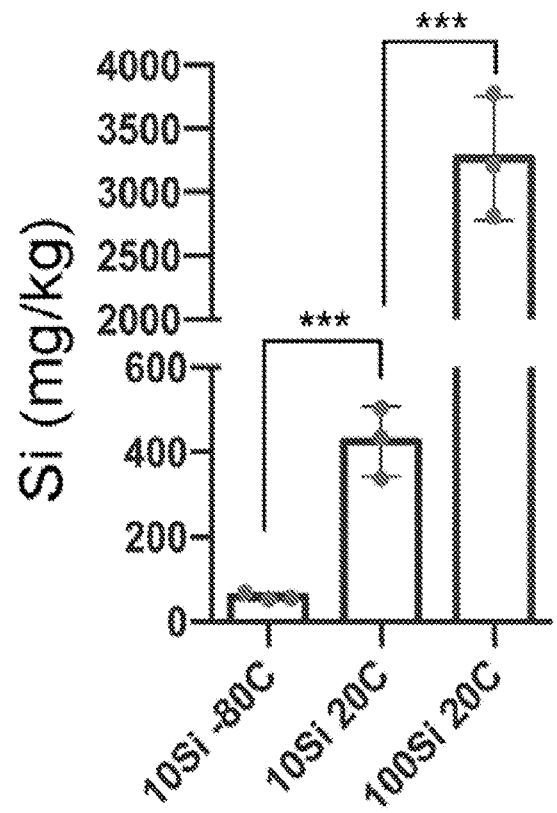
FIG. 12. Silicified cell characterization. (A) ICP-OES analysis of Si content in BR5-Akt cells silicified using either 10 mM or 100 mM silicic acid solution for 24 hours at 20° C. or −80° C. (B) Surface/zeta potential analysis of silicified cells with different surface modifications.

The silicification process can be performed by any suitable method. For example, cells may be silicified at room temperature, as described in International Patent Application No. PCT/US2018/050831. In other embodiments, cells may be silicified using a cryo-silification process described in detail herein that does not require aldehyde fixation. In addition to reducing or eliminating the use of toxic materials, cryo-silification better maintains the biofunctionality of cellular components. Moreover, cryo-silicification can be extended to any cell of interest, enabling personalization. Generally, cryo-silicification involves suspending cancer cells in a hypotonic aqueous solution and then maintaining the cells at −80° C. for 24 hours (FIG. 11A). Scanning electron microscopy (SEM) and energy dispersive spectroscopy (EDS) analysis of silicified murine ovarian cancer cells confirmed the presence of organic matter (C and O) and elemental Si (FIG. 11B). Inductively coupled plasma-optical emission spectroscopy (ICP-OES) analysis of silicified cells demonstrated that this approach resulted in significantly lower Si content compared to silicification at room temperature under higher silicic acid concentrations (FIG. 12A; $p<0.001$). This novel cell silicification process minimizes the overall extent of Si deposition/thickness, resulting in 55-fold less Si content than previously published processes used for cell silicification (Kaehr et al., 2012, *Proc Natl Acad Sci USA* 109:17336-17341). Reducing Si content allows rapid dissolution and revelation of the biomolecular functionality of the cellular components. The silicified cells can be rinsed and stored in a buffer (e.g., PBS) or stored dehydrated until used.

While described above in the context of exemplary embodiments in which the cell being silicified is an ovarian cancer cell, the compositions and methods described herein can involve silicifying any cell type. Alternative suitable cell types include, for example, any cell type that poses a danger to the host and where an immune response against antigens associated with the cell would benefit the host. This includes all types of cancer cells (autologous or allogeneic), pathogenic cells (e.g. microbes), or cells that express antigens associated with cancer. The latter includes embryonic cells and cells genetically modified to cause expression of tumor antigens or tumor-associated antigens.

The ovarian cancer cells used in the experiments described herein were selected as well established high grade syngeneic ovarian cancer models. The BR5-Akt cell line was developed on an FVB background, facilitating in vivo imaging with the IVIS SPECTRUM in vivo imaging system (PerkinElmer, Inc., Waltham, MA). An ID8ova cell line, developed from the ID8 cancer model established in a C57BL/6 strain and transduced to express the model antigen ovalbumin was used for assessments of tumor antigen-specificity.

Surface modification of silicified cells (Si-cells) enable functionalization of the cell surface. Silicified cells can be coated to enhance decoration with pathogen-associated molecular pattern (PAMP), danger-associated molecular molecule (DAMP), or other immunomodulatory moieties. Silica-based surface modification enables surface binding of adjuvants or other immunomodulatory compounds. The native chemistry of the silicified cell surface is dominated by hydroxyl (silanol ≡Si—OH) groups. At physiological pH, the silanol groups are largely dehydroxylated creating an anionic (≡Si—O⁻) surface that adsorbs cationic molecules and polymers that, in turn, can adsorb and retain anionic ligands.

Thus, for example, at least a portion of the surface of a silicified cell can be coated with a cationic polymer/molecule such as, for example, chitosan, polyethyleneimine (PEI), or polylysine. In such embodiments, silicified cells can be incubated with a cationic polymer/molecule under conditions effective to promote coating of at least a portion of the surface of the silicified cell with the cationic polymer. In certain embodiments, silicified cells can be incubated for 5-30 minutes in a chitosan solution (e.g., 2 mg/ml chitosan in 1×PBS or water). In other embodiments, silicified cells can be incubated for 5-30 minutes in a PEI solution (e.g., 0.2 mg/mL in 1×PBS or water; or 0.05-1 mg/ml for titration). In either case, the coating process can be performed under constant rotation.

Figure 12B:
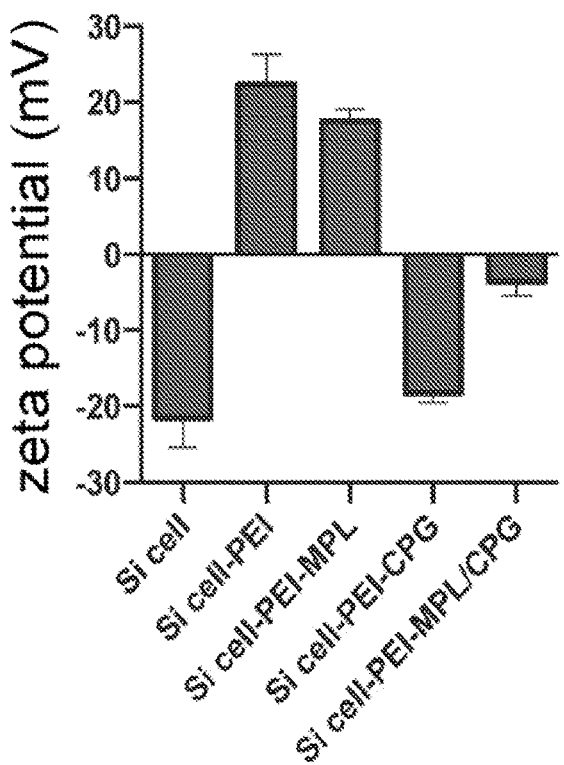
Figure 26A:
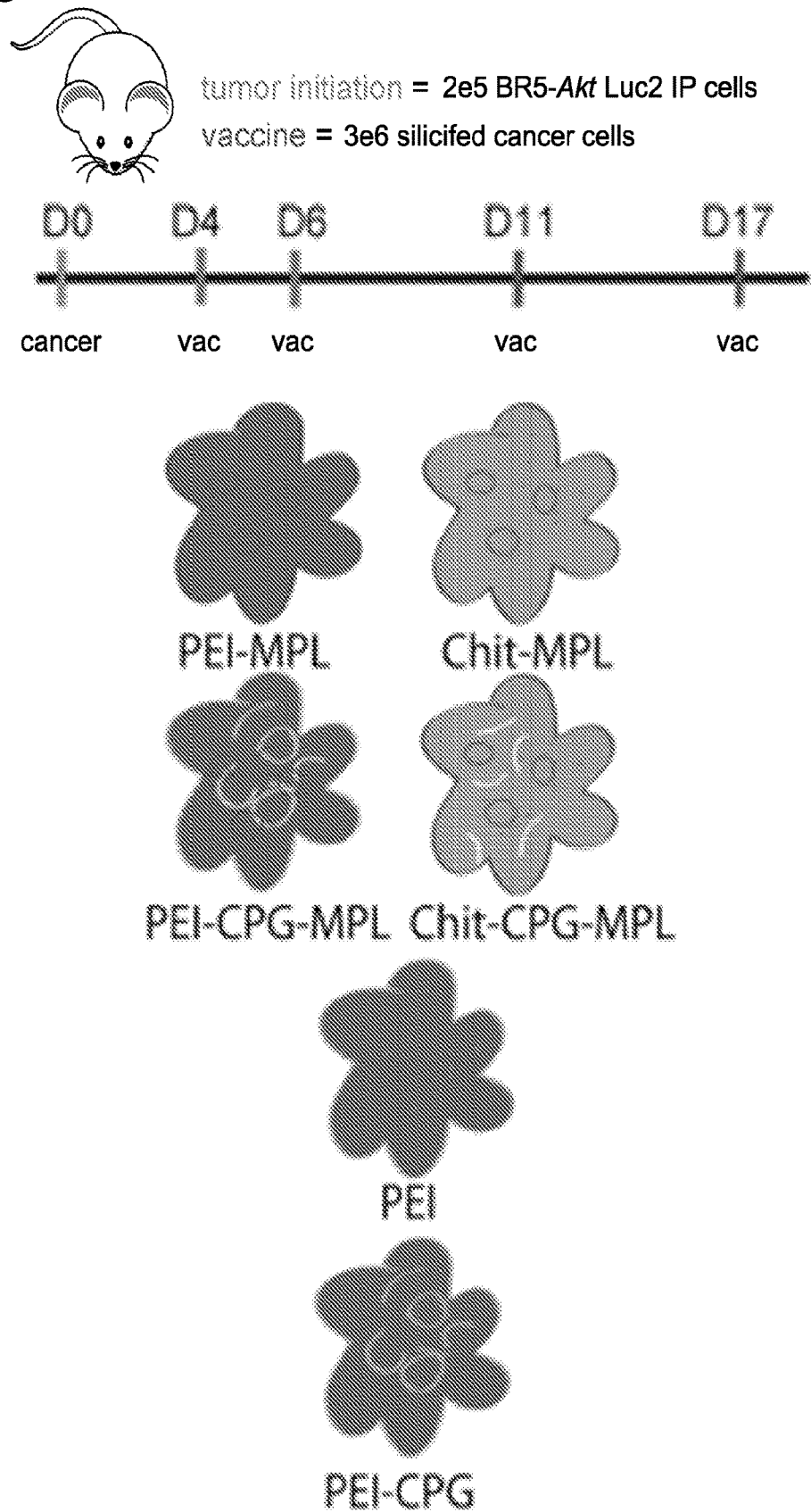
FIG. 26. Therapeutic efficacy of single versus dual TLR ligand vaccine formulations. (A) Timeline for injections and vaccine formulations. (B) IVIS bioluminescence images of FVB mice challenged IP (Day 0) with 2e5 BR5-Akt-Luc2 tumor cells before and after treatment with vaccine (vac) formulations containing chitosan or PEI, with MPL, or MPL and CpG.
Figure 26B:
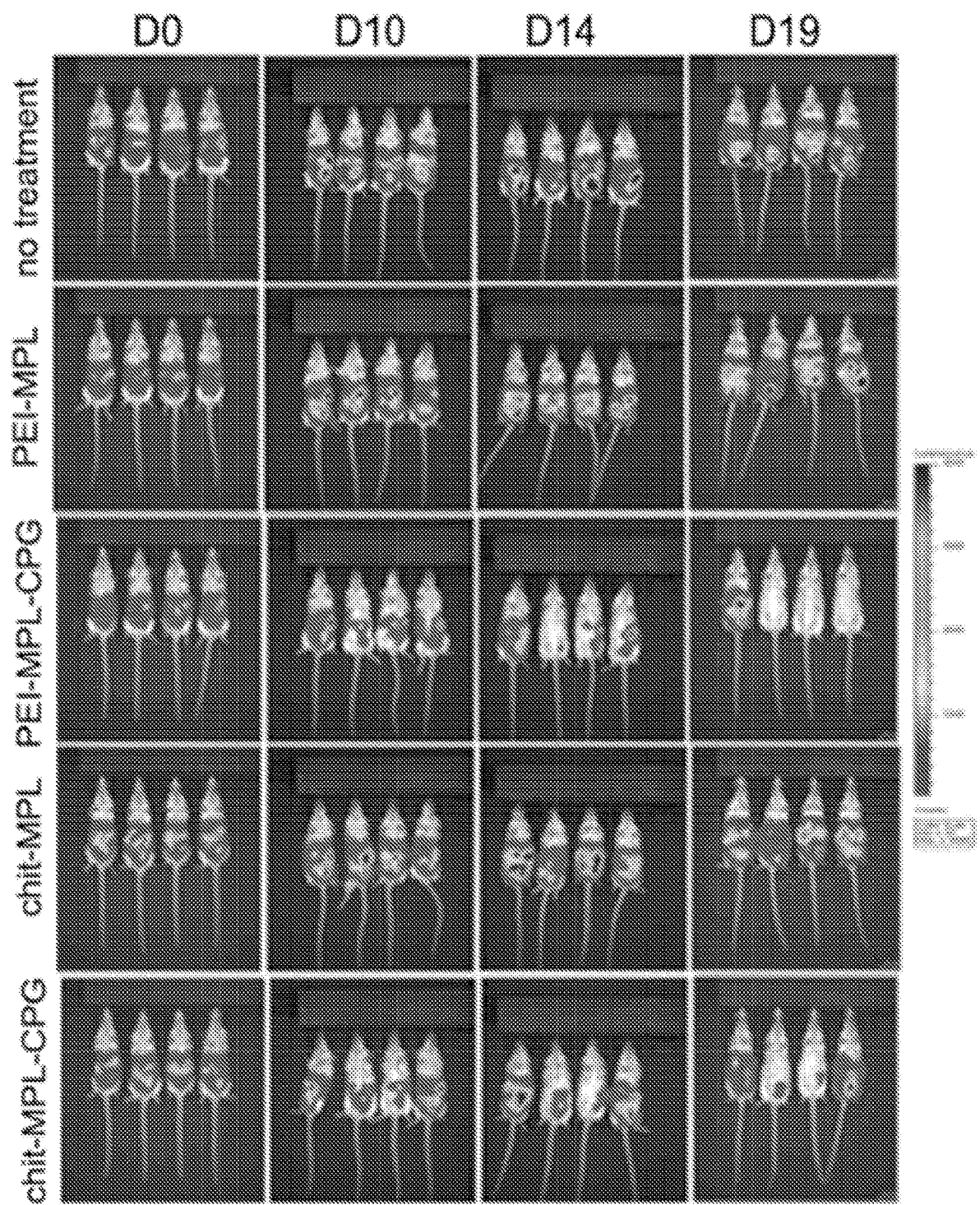
Figure 27A:
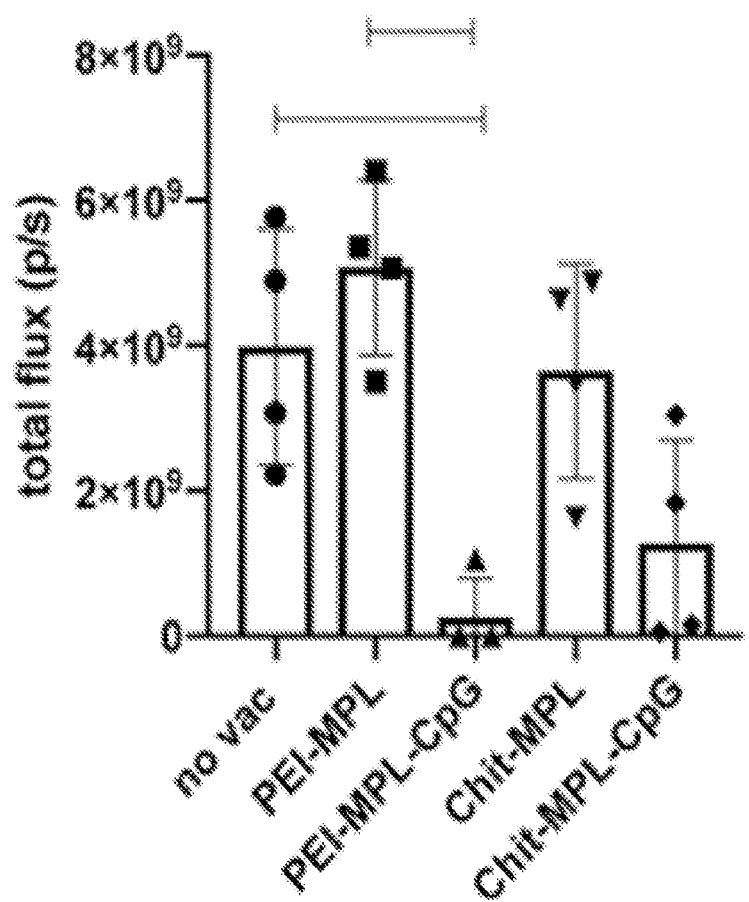
FIG. 27. Therapeutic efficacy of single versus dual TLR ligand vaccine formulations. (A) Average tumor burden (photons/second; p/s) of each group shown in FIG. 25B on Day 19. (B) Survival of FVB mice treated with Si-PEI cells containing CpG, or CpG and MPL.
Figure 27B:
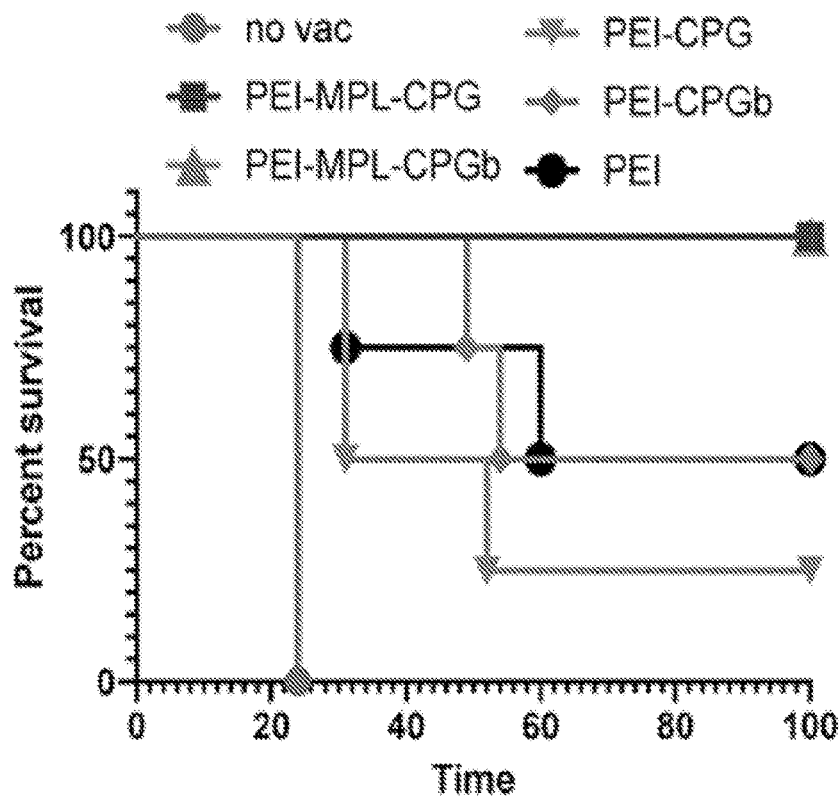

Adsorption of polyethyleneimine (PEI), polylysine (PL), or chitosan (Chit) on the silicified cell surface each reversed the negative silicified cell surface/zeta potential (FIG. 12B). Further, based on zeta potential analysis, PEI, unlike the other cationic molecules, facilitated homogeneous MPL binding to the silicified cell surface (FIG. 12B). PEI is an organic cationic polymer and a reported TLR ligand that increases the immunogenicity of DNA-based vaccines and nanoparticles. Based on these cumulative properties, PEI was selected for vaccine development. Two TLR agonists were selected for surface modification based on their ability to promote Th1 skewing in cancer models: MPL binds to surface/endosomal TLR4, while unmethylated bacterial CpG oligonucleotide (ODN) binds to TLR9 present within the endolysosomal compartment of cells. The effects using single a TLR agonist versus using a combination of TLR4 and TLR9 agonists were compared. Vaccination with Si-PEI-CpG-MPL BR5-Akt cells resulted in optimal treatment outcomes (FIG. 26 and FIG. 27). An exemplary vaccine dose of $3\times10^6$ cells contains approximately 5 μg CpG, 4 μg MPL, 54 μg PEI, and 0.2 Si, with a cells:Si:PEI:CPG:MPL mass ratio of 1000:0.06:18:1.7:1.4, assuming a mass of 1 mg for $1\times10^6$; FIG. 13A).

In some embodiments, one may wish to design the silicified cell to display a cationic, neutral, or hydrophobic immunogenic ligands that requiring the silicified cell surface to be made anionic or hydrophobic to enhance ligand binding. In such embodiments, one can use an anionic molecule or hydrophobic molecule for secondary modification. Exemplary suitable anionic molecules include, but are not limited to, alginate, poly(D-lactic acid), poly(acrylic acid), dextran sulphate, or hyaluronic acid. Embodiments displaying one or more cationic immunogens can includes a first, cationic polymer layer, as described above, and an anionic polymer layer disposed on at least a portion of the cationic polymer layer. The cationic immunogen can then be adsorbed to the anionic polymer layer. Embodiments displaying one or more hydrophobic immunogens can includes a first, cationic polymer layer, as described above, and an hydrophobic polymer layer disposed on at least a portion of the cationic polymer layer. The hydrophobic immunogen can then be adsorbed to the hydrophobic polymer layer.

The coating provided by the polymer or molecule—whether cationic, anionic, or hydrophobic—need not be continuous or uniform. That is, the polymer may provide a discontinuous and/or uneven coating. In certain embodiments, however, the polymer can form a uniform layer that coats the entire silicified cell. When more than one layer is present, each layer can be continuous or discontinuous, independent of the character of any other layer.

The cationic or anionic polymer/molecule surface modification provides an alternative to secondary silane surface modifications described in International Patent Application No. PCT/US2018/050831. Binding of the PAMP, DAMP, cytokine, or other immunogenic moiety to the modified cell surface may include ionic, dipole-dipole, hydrogen bonds, or other type of non-covalent bond. This process provides improved cell integrity and reduced loss of cells compared to secondary silane silicification processes since it does not require successive dehydration and centrifugation steps.

Figure 14A:
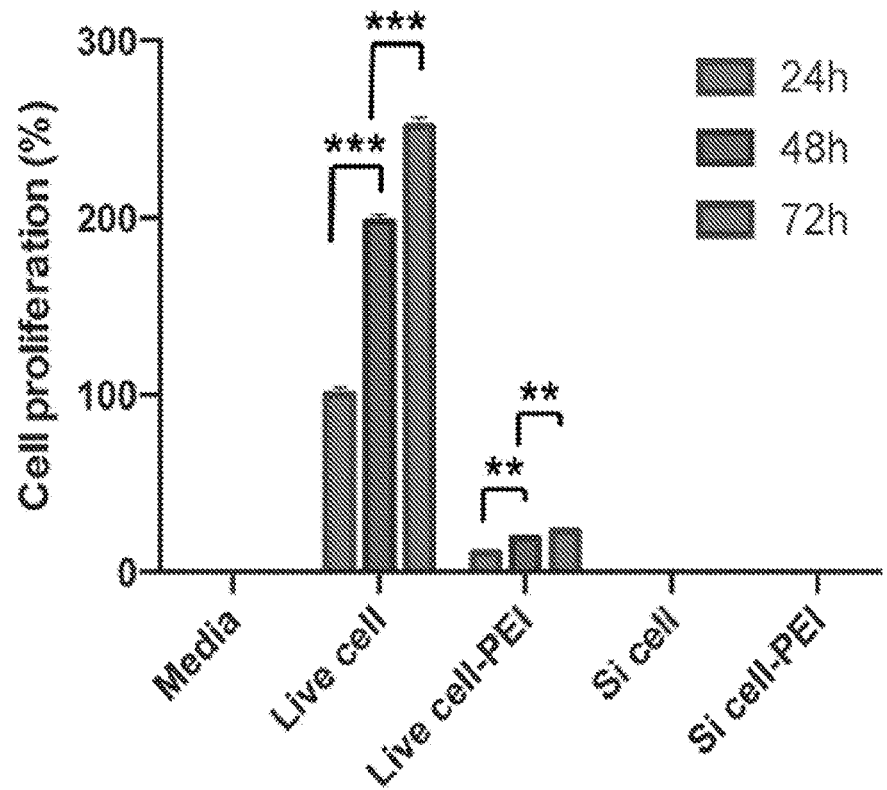
FIG. 14. Silicified cell characterization. (A) Cell-Glo proliferation assay of live or silicified BR5-Akt cells, with and without a 10-minute immersion in 8 μM PEI measured at 24 hours, 48 hours, and 72 hours. (B) Graph of tumor burden over time based on IVIS bioluminescence of FVB mice intraperitoneally injected on Day 0 with either live (cancer challenged) or silicified (vaccine only) BR5-Akt-Luc2 cells (n=3). p<0.01, *p<0.001, ****p<0.0001.
Figure 14B:
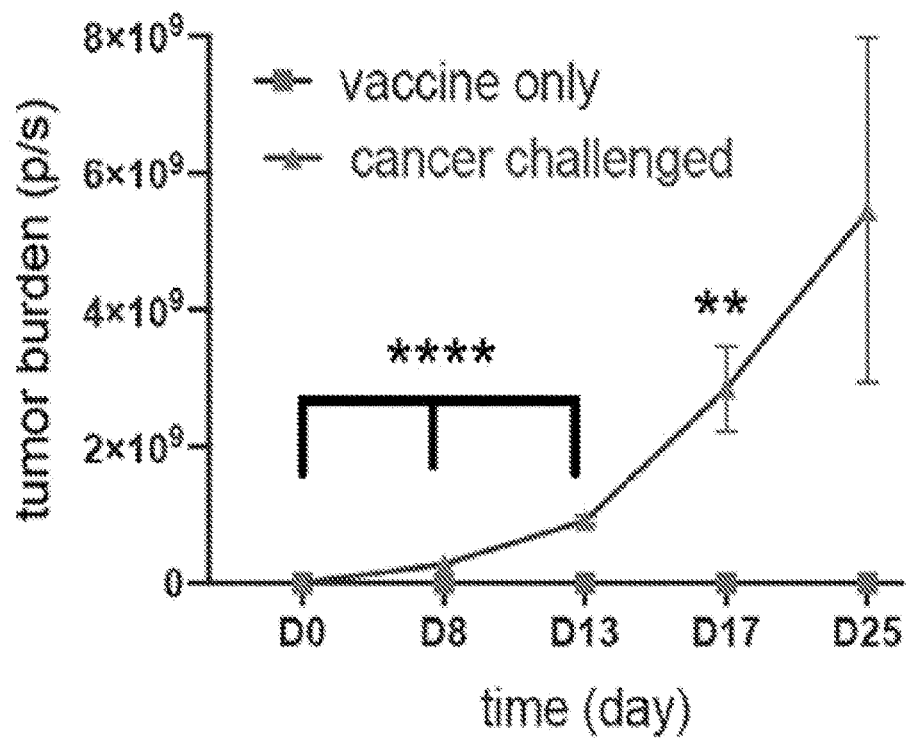

The silicified cells are safe for use in vivo. During vaccine preparation, cancer cells are exposed to an acidic, hypotonic solution, followed by freezing at −80° C., and surface modification, the latter including incubation in 0.2 mg/ml PEI for 10 minutes. Using an absence of ATP production as an in vitro measure of metabolic activity, these methods resulted in complete cell death (FIG. 14A). As an alternative assessment for viability, cellular uptake of propidium iodide (PI) was evaluated by flow cytometry. Notably, scatter dot plots of live or Si-cells supported retention of cell structure following silicification. In these experiments, all silicified cells displayed intracellular PI staining (FIG. 13B), confirming that Si-cells are not viable. Finally, to ensure that silicified tumor cells could not establish tumors in vivo, luciferase positive silicified tumor cells were injected intraperitoneally into mice and tumor growth was assessed (FIG. 14B). None of these mice developed bioluminescent evidence of viable tumor, and histologic assessment at necropsy confirmed a lack of tumor growth. These data confirm that silicified tumor cells can be safely administered in vivo.

Surface modification of Si-cells with TLR agonists enhances uptake by, and activation of, dendritic cells. Presentation of PAMPs, DAMPS, or other immunomodulatory moiety on the surface of silicified cells stimulated internalization by and activation of bone marrow-derived dendritic cells (BMDCs). Cell silicification therefore both preserves cells and can functionalize the cell surface. This disclosure therefore discloses creating immunogenic silicified cells (e.g., silicified tumor cells) that also mimic pathogens, thereby stimulating dendritic cells to internalize the immunogenic silicified cells, activate, and process cellular antigens. Thus, in the context of a silicified tumor cell, the tumor cell is modified to mimic a pathogen so that the silicified tumor cell is internalized by dendritic cells, which then process the tumor antigens.

Figure 15A:
FIG. 15. Surface functionalization enhances DC uptake and activation in vitro. 2D and surface-rendered 3D fluorescent confocal micrographs showing internalization and intracellular location of silicified tumor cells following one-hour incubation with GM-CSF-matured BMDC. (A) Actin fluorescence is shown at three threshold levels for inside and surface views. The arrow points to active phagocytosis. (B) Tumor cells were preincubated with fluorescent nanoparticles prior to silicification to distinguish vaccine cells from DC.
Figure 15B:
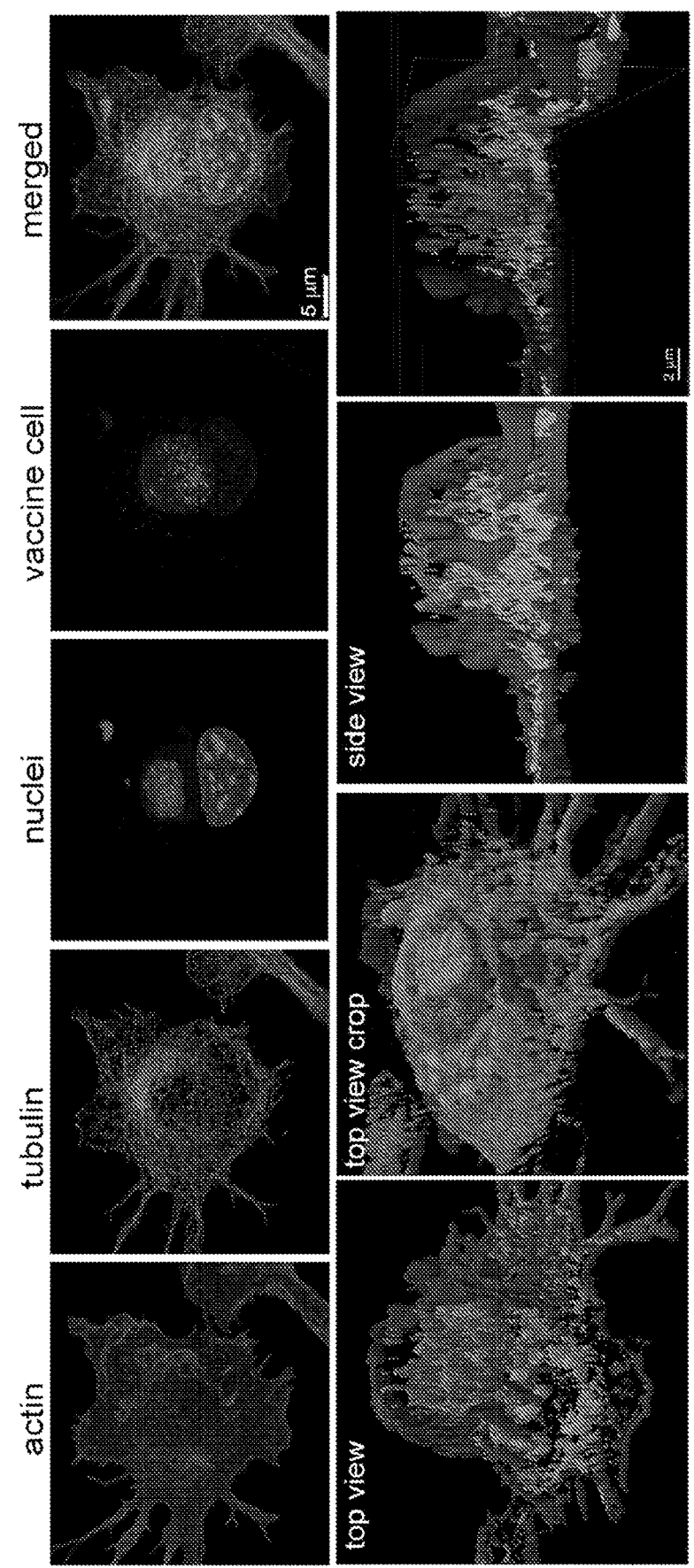
Figure 16A:
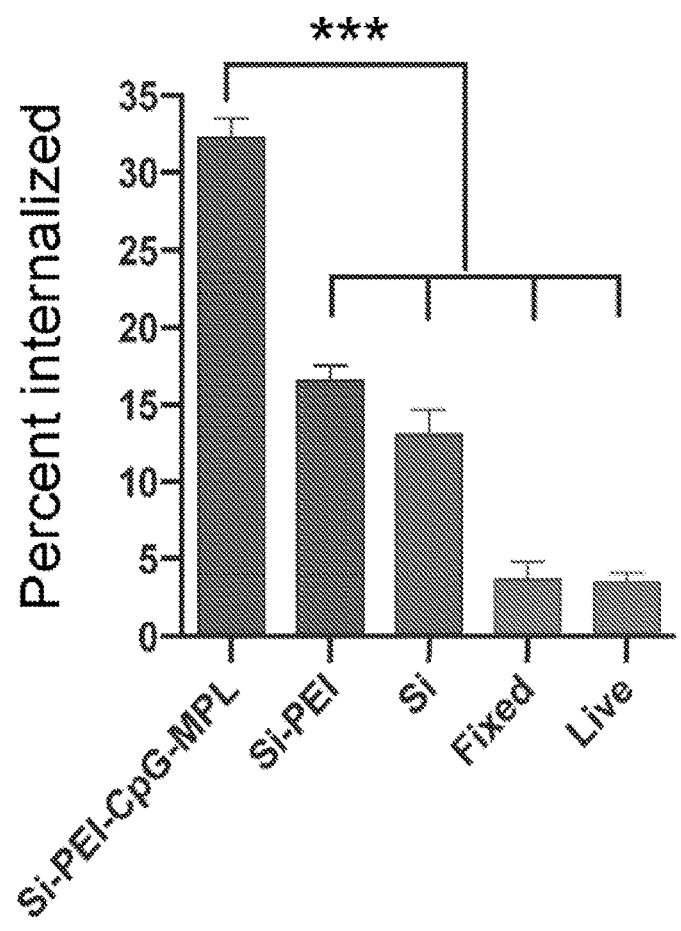
FIG. 16. Surface functionalization enhances DC uptake and activation in vitro. (A) Flow cytometry analysis of DC uptake of silicified BR5-Akt cells presenting no TLR ligands (Si); PEI; or PEI, CpG, and MPL (p<0.001). (B) Flow cytometry analysis of MHC I presentation of tumor antigen (SIINFEKL-H2Kb) on DC 72 hours after addition of ID8ova vaccine cells or control irradiated ID8ova cells. (***p<0.001).
Figure 16B:
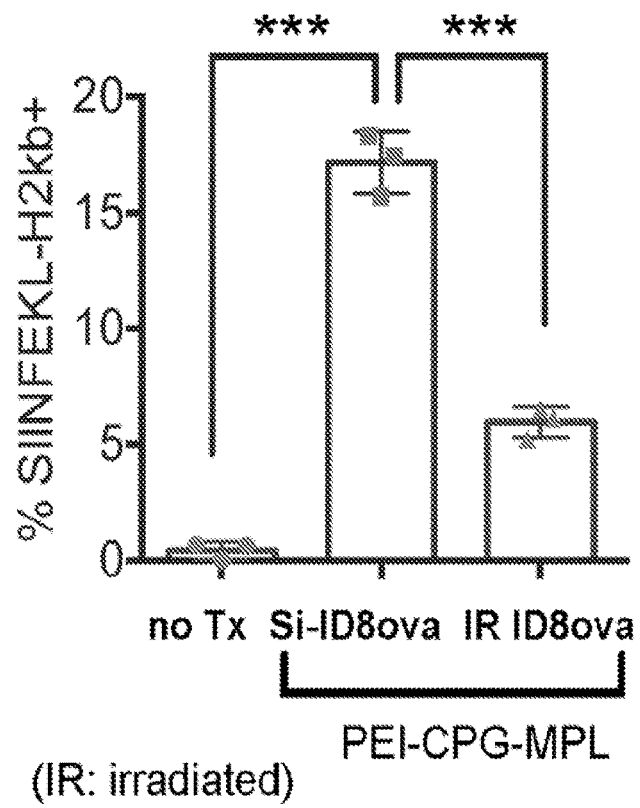

Engagement of TLR4 and TLR9 on antigen presenting cells (APC) promotes antigen internalization, cytokine secretion, and expression of costimulatory molecules and major histocompatibility complex (MEW). To test whether surface modification with CpG and MPL promoted Si-cell uptake and processing by APC, co-culture experiments were performed with bone marrow-derived dendritic cells ex vivo. Confocal microscopy and flow cytometry confirmed that Si-cells are engulfed by dendritic cells in vitro. 3D confocal images of actin-labeled (red: rhodamine phalloidin; blue: DAPI) dendritic cells show the presence of internalized Si-PEI-CpG-MPL BR5-Akt tumor cells after one hour incubation at 37° C. (FIG. 15A, 15B). The actin fluorescence is shown with variable thresholding to enable identification of intracellular and surface binding on the dendritic cells (FIG. 15A). To specifically track silicified cells, tumor cells (blue: actin; green: tubulin; violet: DAPI) were loaded with fluorescent nanoparticles (red; rhodamine B labeled to function as a probe) prior to silicification (FIG. 15B). Internalization of Si-PEI-CpG-MPL, Si-PEI, or Si BR5-Akt tumor cells by dendritic cells was compared to that of live or paraformaldehyde-fixed tumor cells using flow cytometry and fluorescently labeled cells. Silicified tumor cells bound with CpG and MPL had a nine-fold increase in uptake compared to live or fixed tumor cells (FIG. 16A). Finally, tumor antigen presentation in the context of MHC I was tested using the ID8ova cell line that expresses the model antigen ovalbumin. Ova peptide (SIINFEKL; SEQ ID NO:1) presentation on MHC I by dendritic cells was assessed by flow cytometry analysis after 72 hour co-culture with Si-PEI-CpG-MPL-ID8ova cells. These experiments demonstrated that silicification and surface modification significantly enhanced tumor antigen presentation compared with other vaccine preparation methods, specifically irradiation (100 Gy) (FIG. 16B).

Also, silicification of cancer cells without prior fixation results in similar levels of dendritic cell activation and increased antigen presentation compared to paraformaldehyde-fixed, silicified cancer cells. The elimination of fixative is advantageous for clinical use, enabling the use of the silicified cancer cell pathogen mimics as personalized therapeutic cancer vaccines.

While described herein in the context of exemplary embodiments in which the silicified cell is surface modified to be decorated with monophosphoryl lipid A (MPL) or a TLR agonist (e.g., CpG), the silicified cells, and methods of using silicified cells, described herein can involve silicified cells functionalized with one or more PAMPs, one or more DAMPs, or one or more alternative immunomodulatory moieties, or any combination of two or more PAMPs, DAMPS, and/or immunomodulatory moieties, as desired. Exemplary PAMPs include, but are not limited to, lipopolysaccharide (LPS), monophosphoryl lipid (MPL), Poly IC, double-stranded RNA, lipoteichoic acid, peptidoglycan, viruses, and unmethylated CpG. DAMPS are endogenous molecules created upon tissue injury. Exemplary DAMPs include, but are not limited to, heat shock proteins, high mobility group box 1, proteins such as hyaluronan fragments, and non-protein targets such as ATP, uric acid, DNA and heparin sulfate.

Figure 17A:
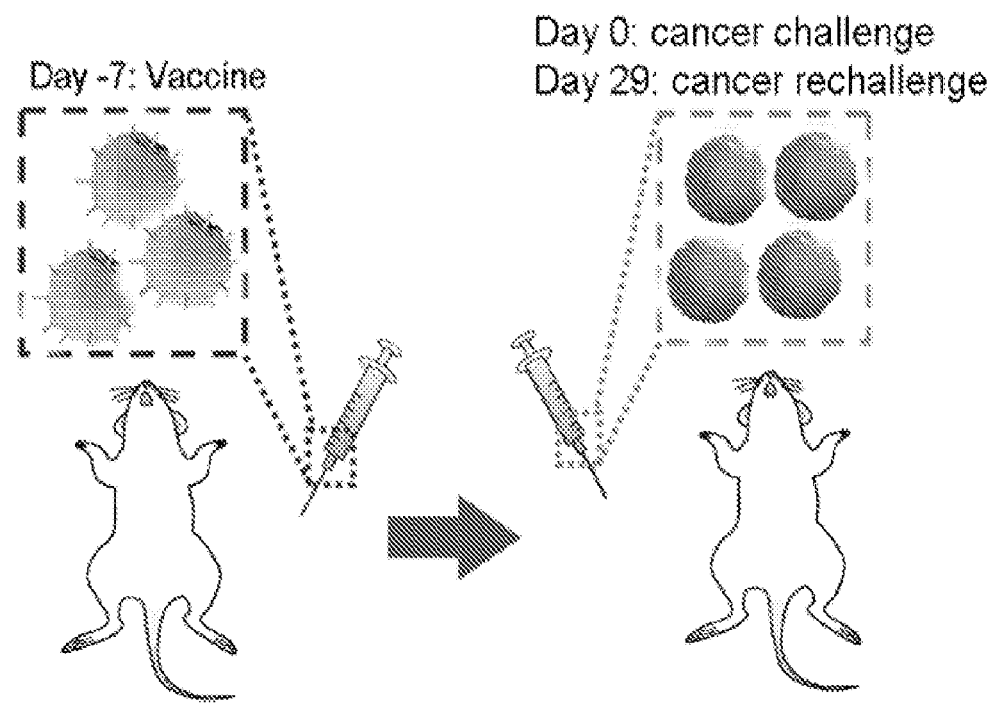
FIG. 17. Treatment with silicified cells induces an immune response in vivo. (A) Tumor engraftment was evaluated in female, six-week-old FVB mice injected intraperitoneally with PBS (no Tx) or 3e6 BR5-Akt vaccine cells (vac) seven days prior to intraperitoneal tumor challenge with 2e5 BR5-Akt-Luc2 cells. Tumor burden is presented graphically as photons/sec (p/s) and corresponding IVIS spectrum images of luciferase bioluminescence are shown. A durable memory response was tested for by secondary tumor challenge on Day 28. (B) Antigen specificity was tested in mice by intraperitoneal injection with vaccine cells or no antigen control mesoporous silica nanoparticles (MSN) presenting PEI, CpG, and MPL. Kaplan-Meier survival curves and tumor burden are shown, the latter graphically and as IVIS images.
Figure 1:
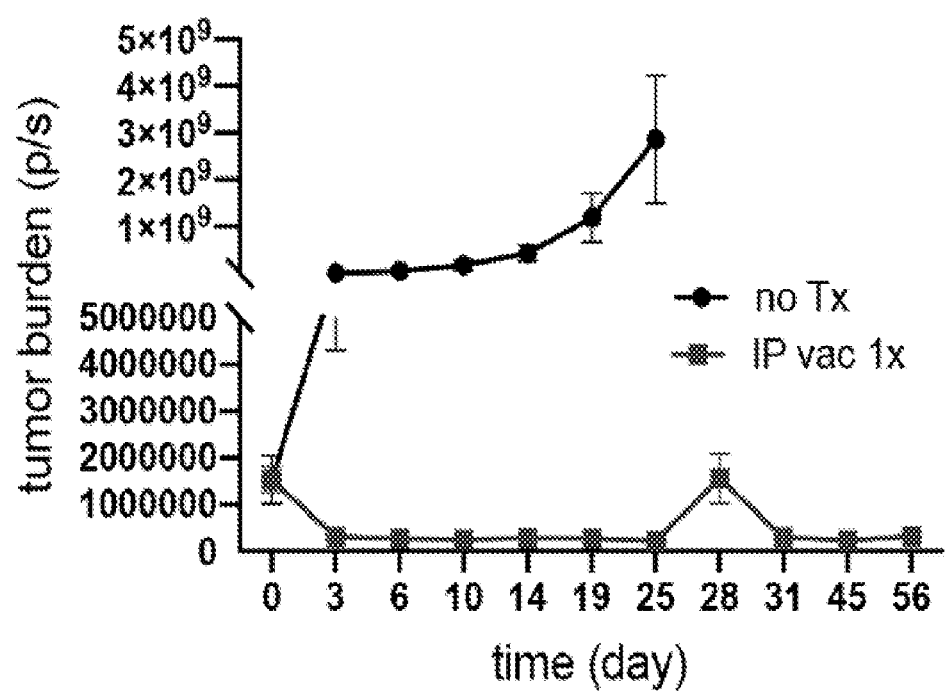
Figures 2, 17A:
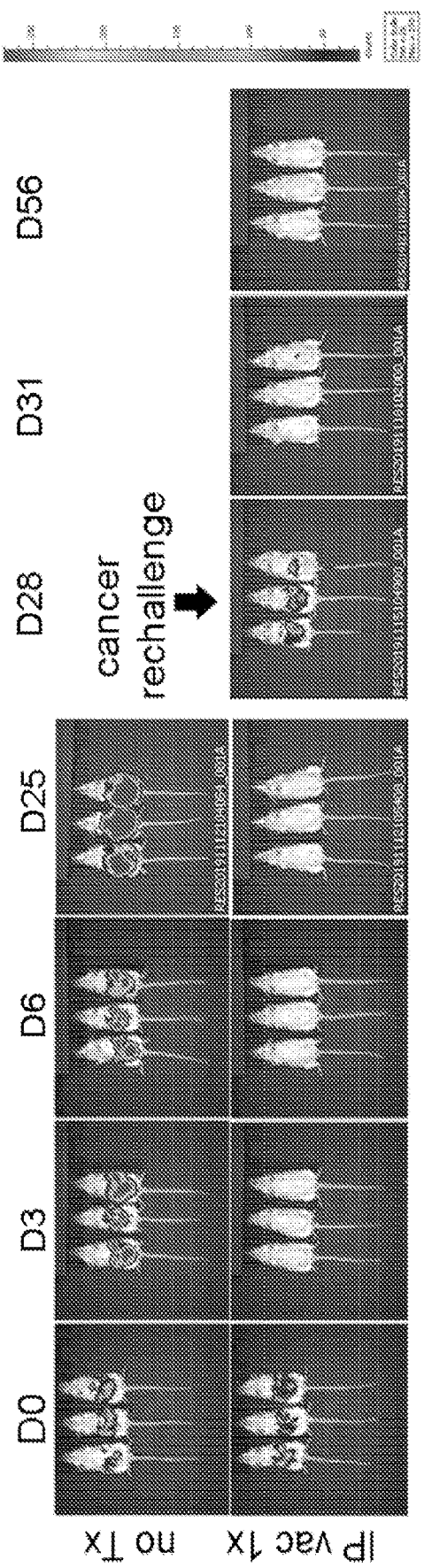
Figures 2, 17B:
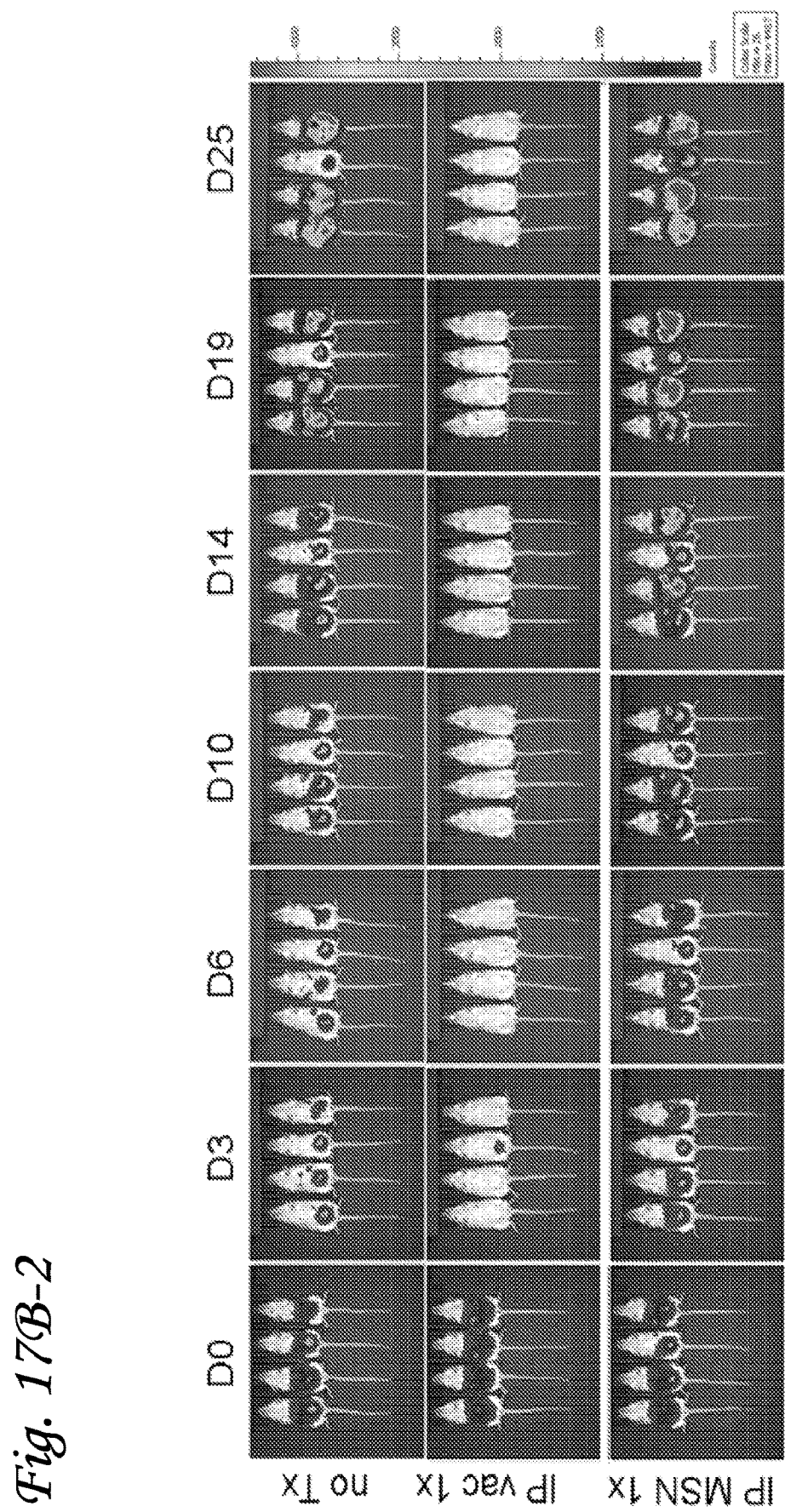

Silicified, surface modified cells generate cell-specific T cell immunity in vivo. To evaluate the immunogenicity of surface-modified Si-cells in vivo, mice were injected with silicified, surface modified tumor cells prior to tumor challenge and evaluated for evidence of a T cell response. In these experiments, female FVB mice (n=3) received $3 \times 10^6$ Si-BR5 tumor cells intraperitoneally (IP) seven days prior to tumor challenge. Tumor burden in vaccinated mice was compared with unvaccinated controls using bioluminescence with IVIS Spectrum imaging and quantified as photons/second (FIG. 17A). Within three days of tumor challenge, no bioluminescence was detectable in the experimental group. In contrast, the PBS treated control mice showed progressive tumor growth requiring euthanization by Day 31. To assess whether this vaccine effect was associated with the generation of immune memory, treated mice that had no evidence of tumor were subjected to a second tumor challenge on Day 28, a time point when all control mice were moribund. Following a second intraperitoneal tumor challenge, these mice were monitored for tumor engraftment through Day 56. None of these mice demonstrated evidence of bioluminescent tumor, and tumor clearance was confirmed histologically at necropsy. To confirm that this effect was antigen-specific, mesoporous silica nanoparticles (MSN) were used as an additional control. MSN have similar surface presentation of PEI, CpG, and MPL as Si-cells but lack the tumor cell component with associated antigens. Vaccination with modified MSN had no survival benefit compared with untreated controls (n=4; FIG. 17B), suggesting that silicified tumor cells generated the effects of vaccination shown in FIG. 17A.

Figure 18A:
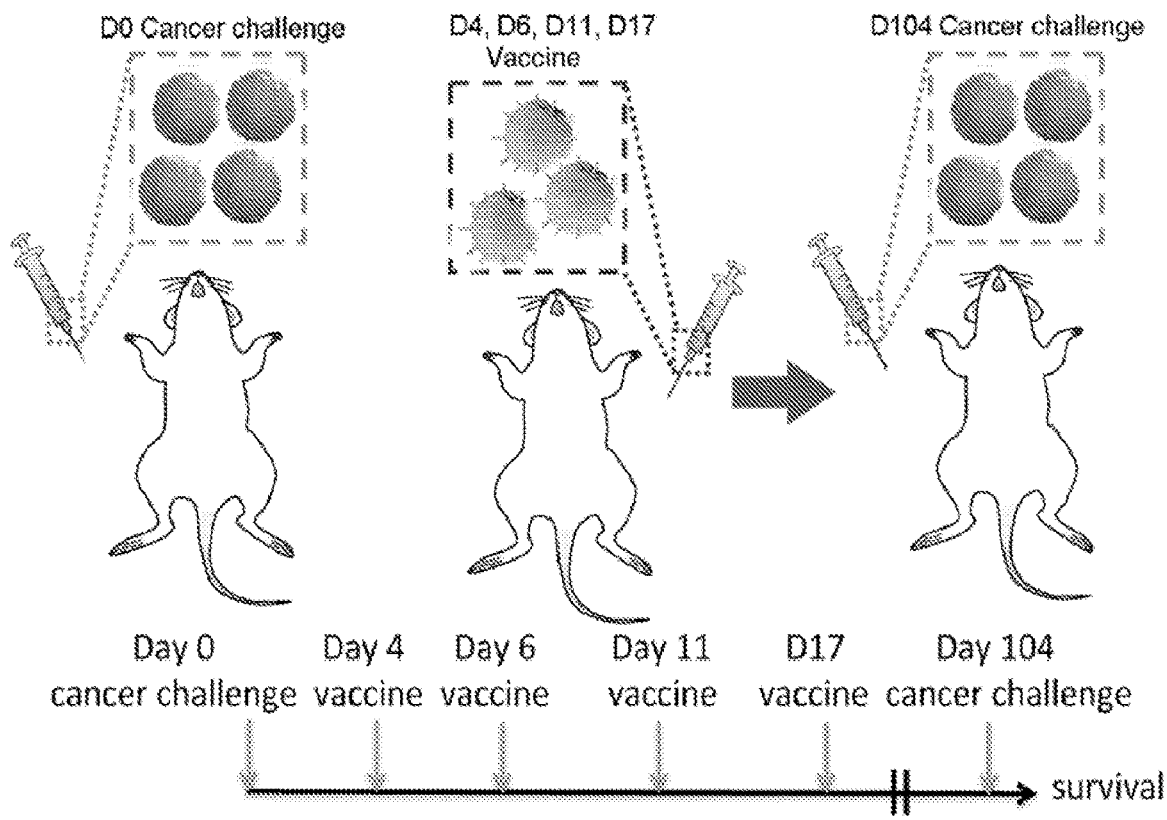
FIG. 18. Therapeutic vaccination clears established ovarian tumors. (A) Diagram of treatment schedule. (B) Tumor burden (photons/s) in FVB mice injected IP with 2e5 BR5-Akt-Luc2 cells (Day 0) and vaccinated with 3e6 BR5 vaccine cells at the schedule indicated. 100 days after initial vaccination, surviving mice were re-challenged with 2e5 BR5-Akt-Luc2 cancer cells.
Figure 18B:
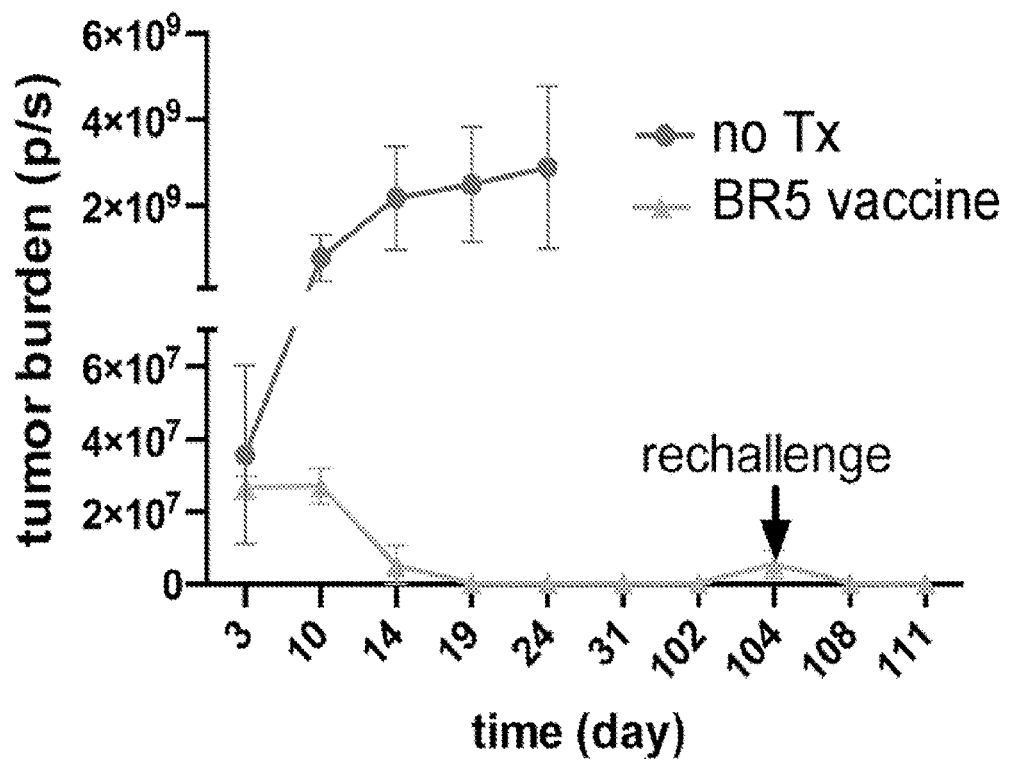
Figure 19A:
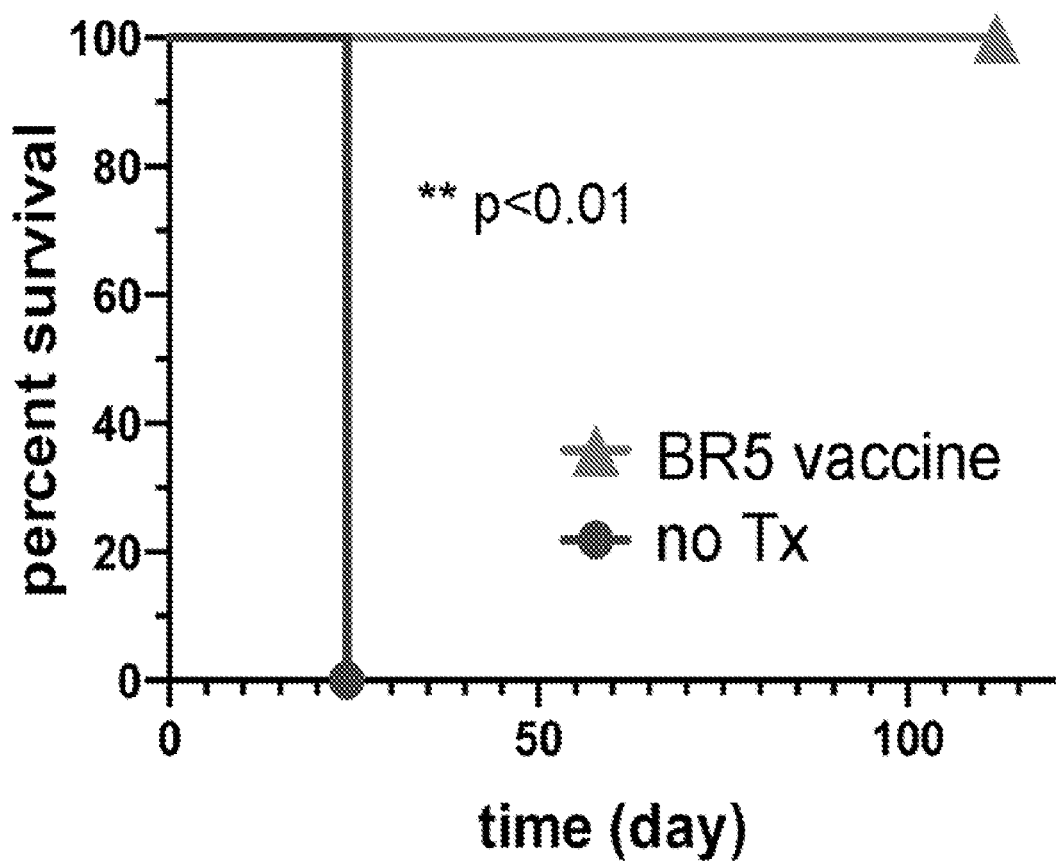
FIG. 19. Therapeutic vaccination clears established ovarian tumors. (A) Kaplan-Meier survival curves. (B) IVIS bioluminescent images of control and vaccinated mice over time.
Figure 19B:
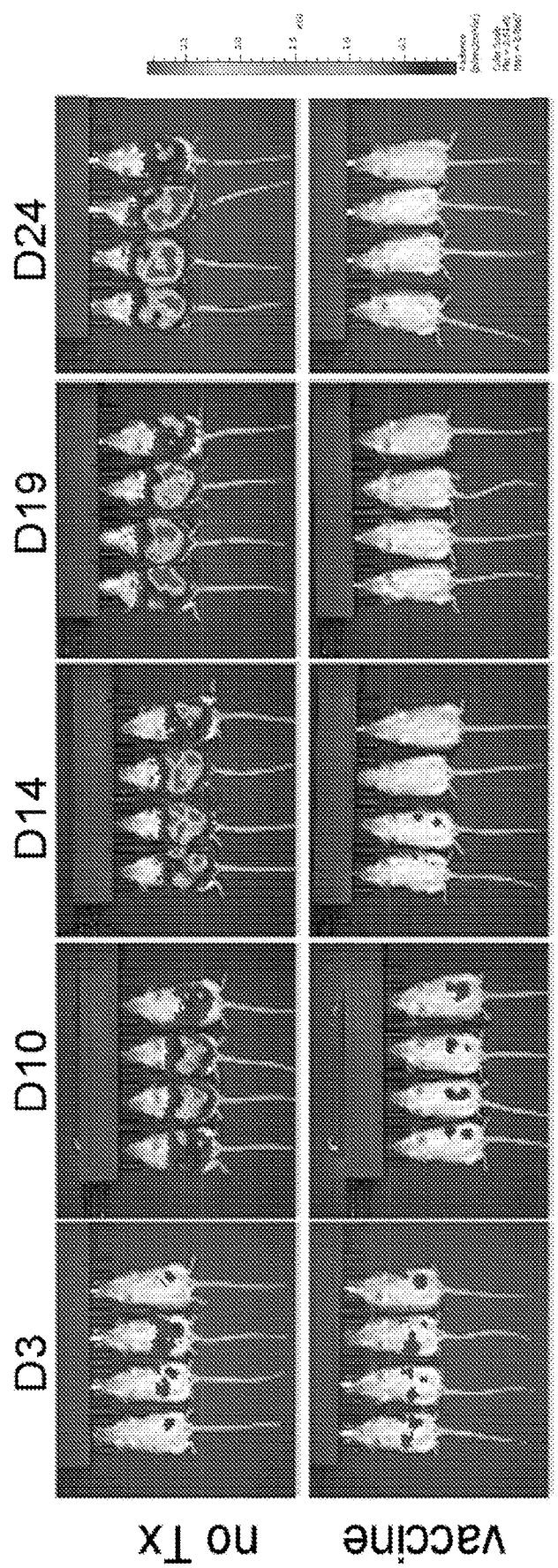

Therapeutic vaccination in vivo results in durable survival benefit. The ability of vaccination to clear established tumors was evaluated in FVB mice with BR5-Akt-Luc2 tumors (n=4). In these experiments, mice were injected with Si-tumor cells on Day 4, Day 6, Day 11, and Day 17 after intraperitoneal tumor challenge (FIG. 18A). Mice vaccinated with the Si-PEI-CpG-MPL tumor cells eliminated all detectable tumor based on bioluminescence, resulting in durable survival beyond 100 days (FIGS. 18B, 19A, and 19B). To test whether therapeutic vaccination could generate an immunological memory response, these mice were subjected to a second tumor challenge on Day 104 and demonstrated that they were again able to clear tumor (FIG. 18B). In summary, vaccination using silicified cells has a marked therapeutic effect and is able to induce immunologic memory.

Figure 20A:
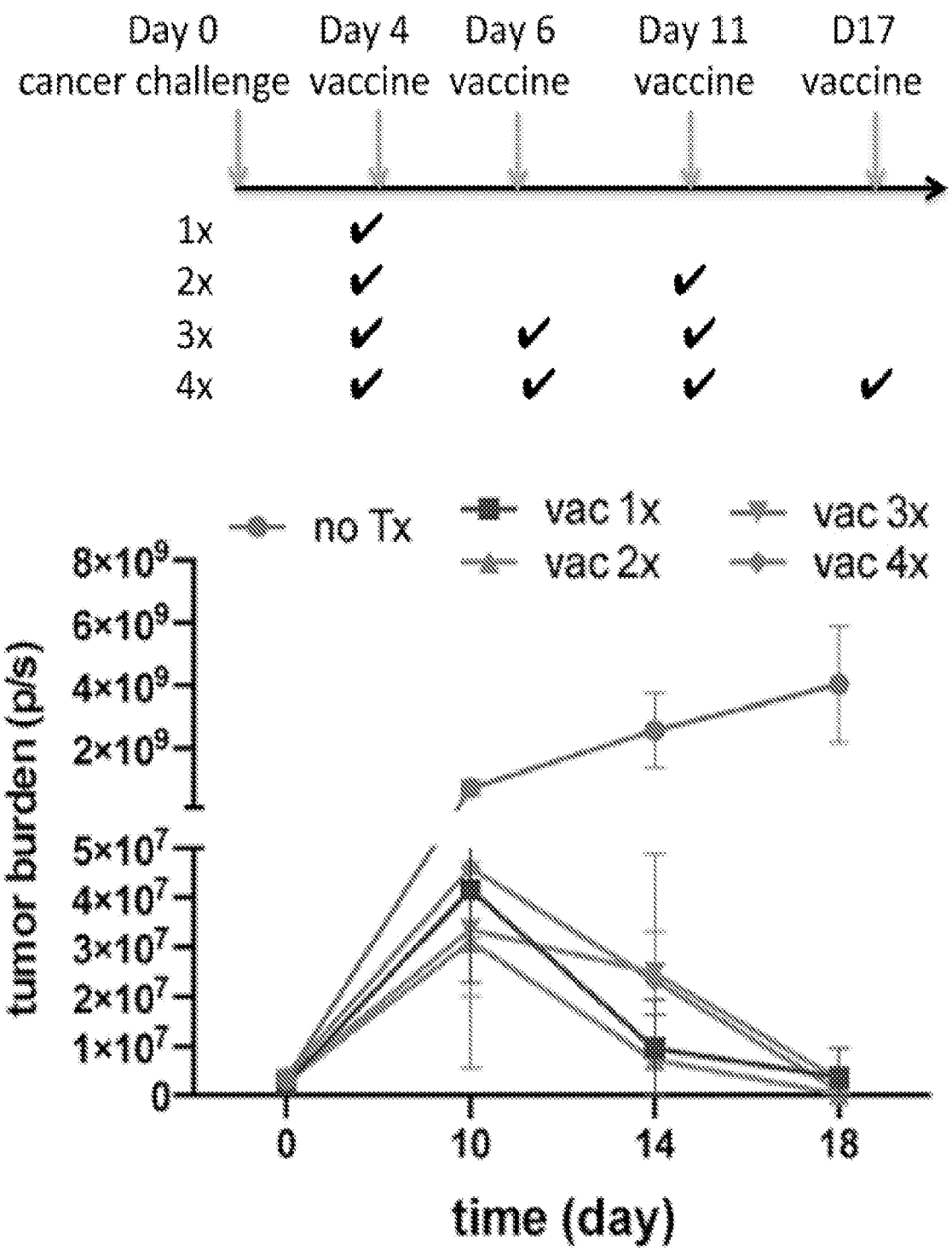
FIG. 20. Dosing was evaluated in FVB mice intraperitoneally injected on Day 0 with $2 \times 10^5$ BR5-Akt-Luc2 cells. (A) Dosing schedule was varied as indicated. Line graph shows tumor burden (photons/second) over time by treatment group. (B) IVIS imaging of tumor burden (photons/second) over time by treatment group.
Figure 20B:
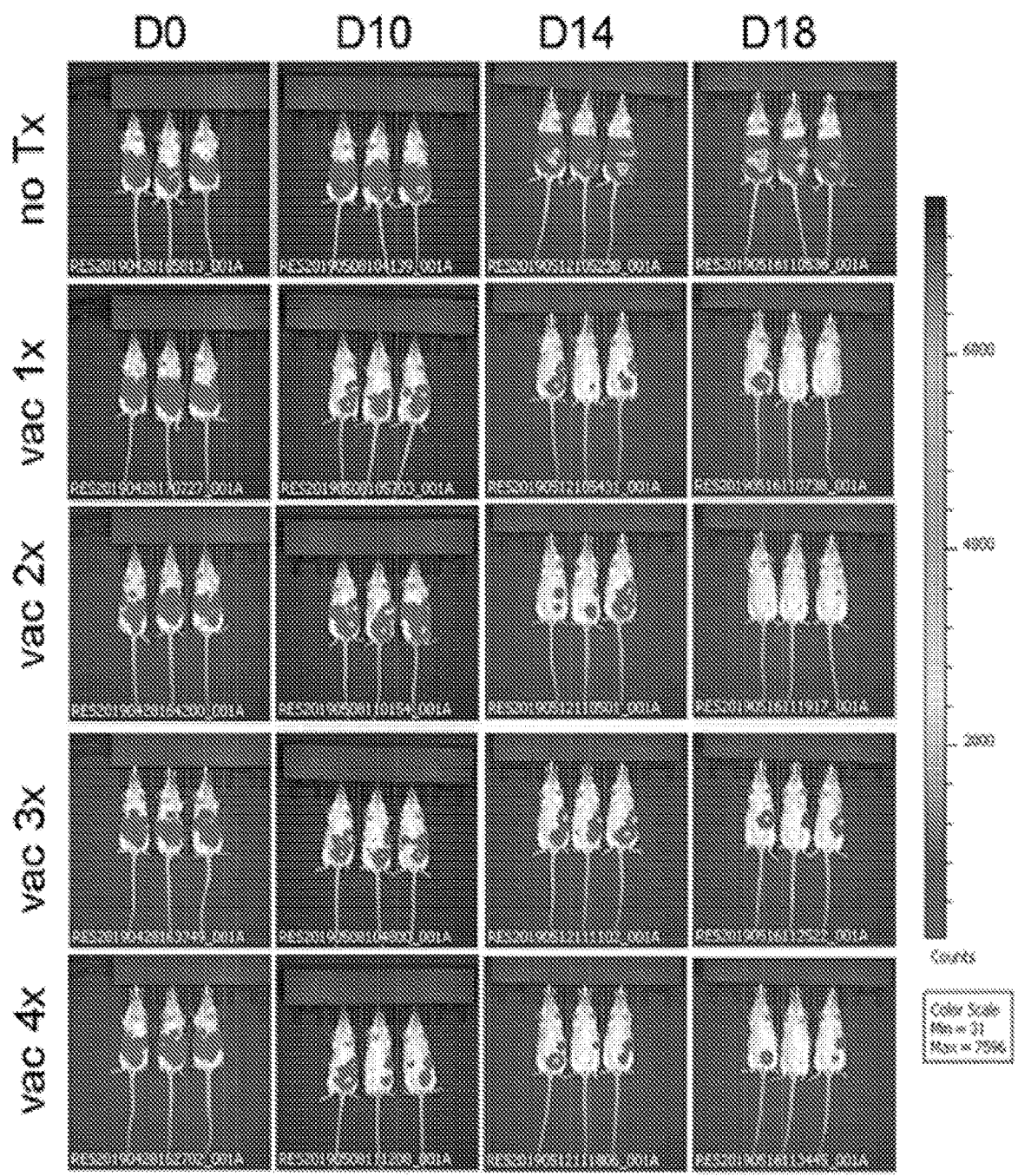

Different dosing and vaccination schedules were tested to optimize the therapeutic efficacy of the Si-PEI-CpG-MPL vaccine. Although all vaccinated mice had improved outcomes compared with controls, the greatest effect was seen in mice receiving two doses of vaccine; a first dose on Days 4 and a second dose on Day 11 (n=3; FIG. 20A, 20B). Dosing at one-week intervals for induction is consistent with previous clinical trials for autologous vaccines (e.g. ONCO-VAX, Vaccinogen, Inc., Baltimore, MD), and may be followed by one or boosters. Boosters may be administered as a single booster six months following the initial vaccination or monthly boosters. Monthly boosters can be administered starting at any suitable time following the initial vaccination such as, for example, one month, two months, three months, four months, five months, six months, seven months, eight months, nine months, ten months, eleven months, or twelve months after the initial vaccination.

Figure 21A:
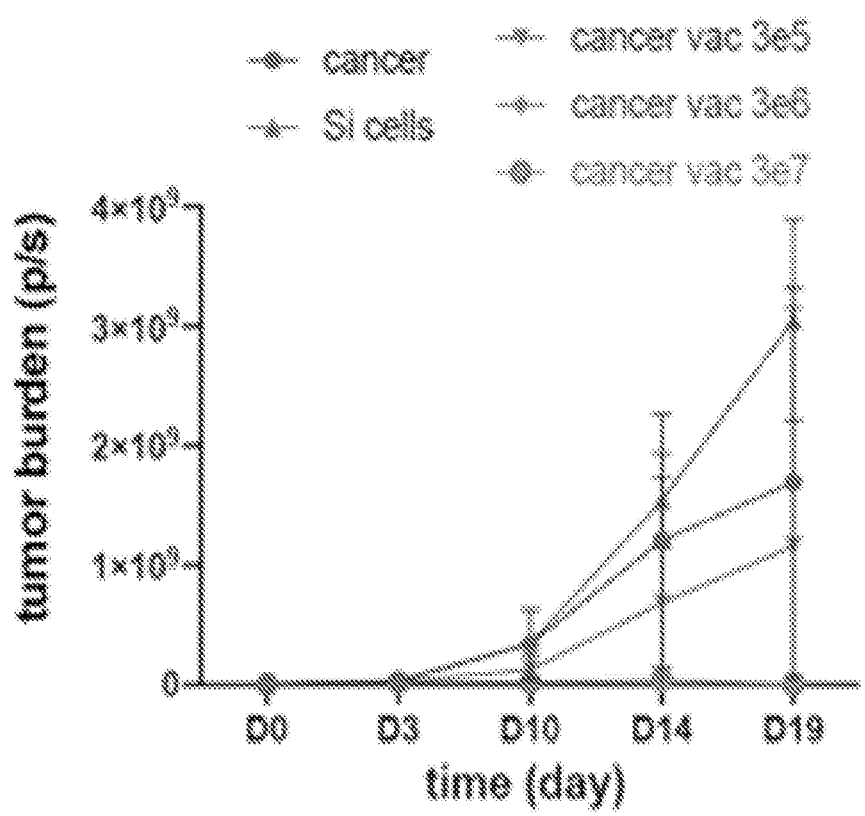
FIG. 21. Effect of dosing (number of vaccine cells per injection) on tumor burden was evaluated in FVB mice intraperitoneally injected on Day 0 with $2 \times 10^5$ BR5-Akt-Luc2 cells. The indicated doses of silicified cells were administered on Day 4 and Day 11 (A) Line graph shows tumor burden (photons/second) over time by treatment group. (B) IVIS imaging of tumor burden (photons/second) over time by treatment group.
Figure 21B:
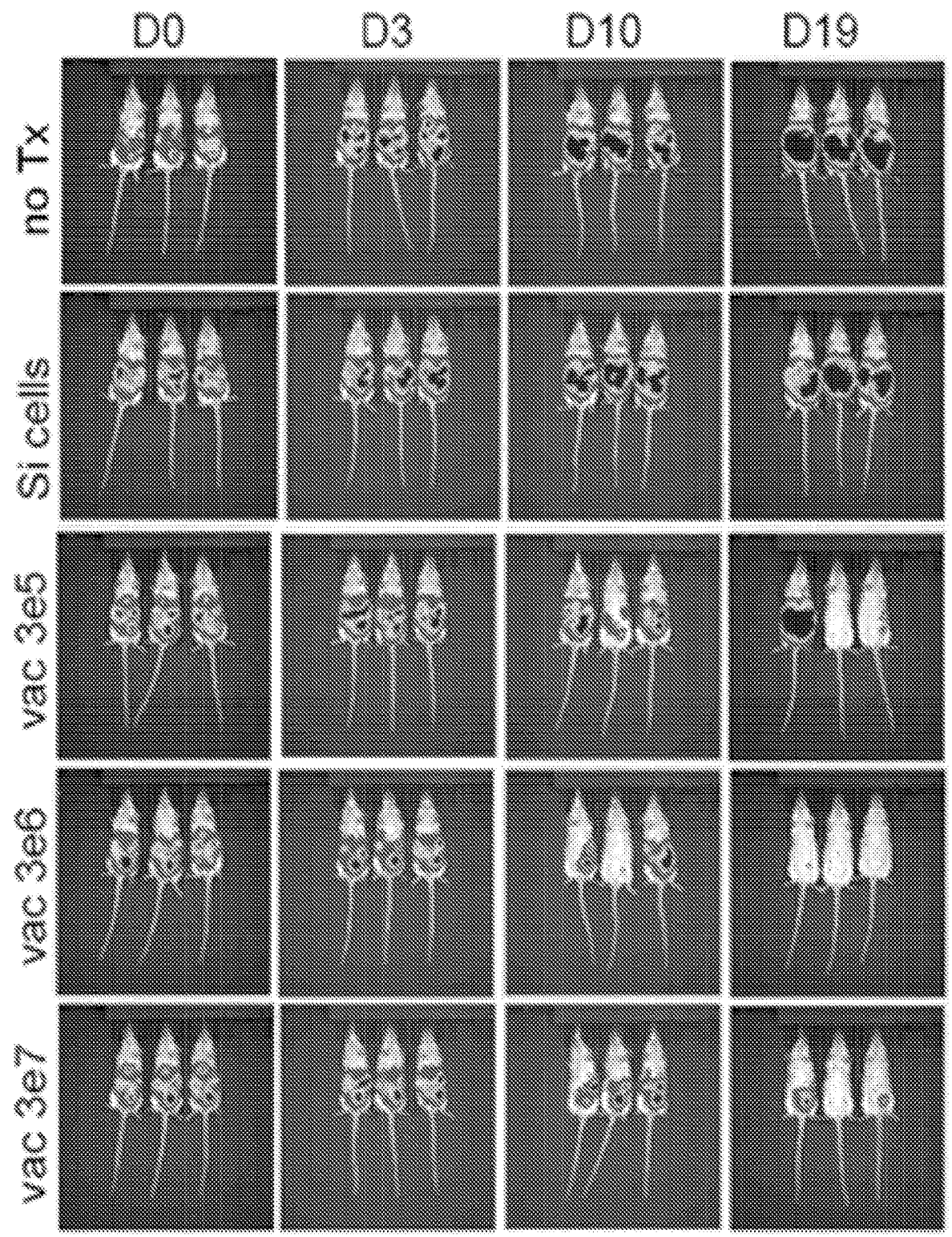

The effect of dose using this schedule was evaluated next. A dose of $3 \times 10^6$ immunogenic silicified cells performed best (n=3; FIG. 21A, 21B). Many autologous tumor cell vaccines are most effective at doses higher than $10 \times 10^6$ cells. As an example, VIGIL (Gradalis, Inc., Carollton, TX) immunotherapy is given to patients at a dose of $1 \times 10^7$ vaccine cells/dose, with a minimum of four doses and a maximum of 12 doses. Dosing for immunotherapy is determined by the amount of immune stimulation needed to produce a measured immune response. Based on the mouse model data presented herein, Si-cells in the range of millions of cells/dose was able to elicit a productive immune response. Based on other clinical trials for cell-based immunotherapy, doses required to stimulate immune responses in humans is also in the range of millions of cell/dose. One also can use immunostimulation modelling methods to inform dosing, as previously described (Rhodes et al., 2018, *npj Vaccines* 3:36).

Figure 28A:
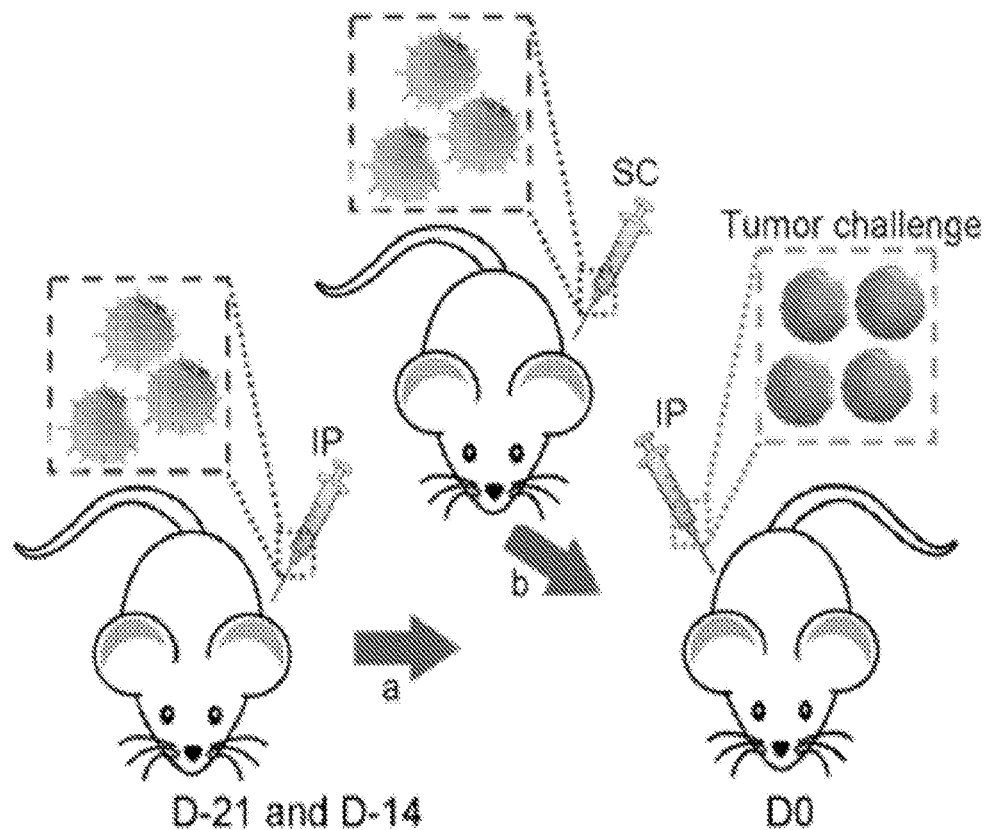
FIG. 28. Vaccination effects on tumor challenge at disparate locations. Both intraperitoneal and subcutaneous treatment with Si-cells reduce tumor burden after intraperitoneal tumor challenge. (A) FVB mice were vaccinated intraperitoneally or subcutaneously (D-21 and D-14) with $3 \times 10^6$ Si-cells. Average tumor burden.
Figure 28B:
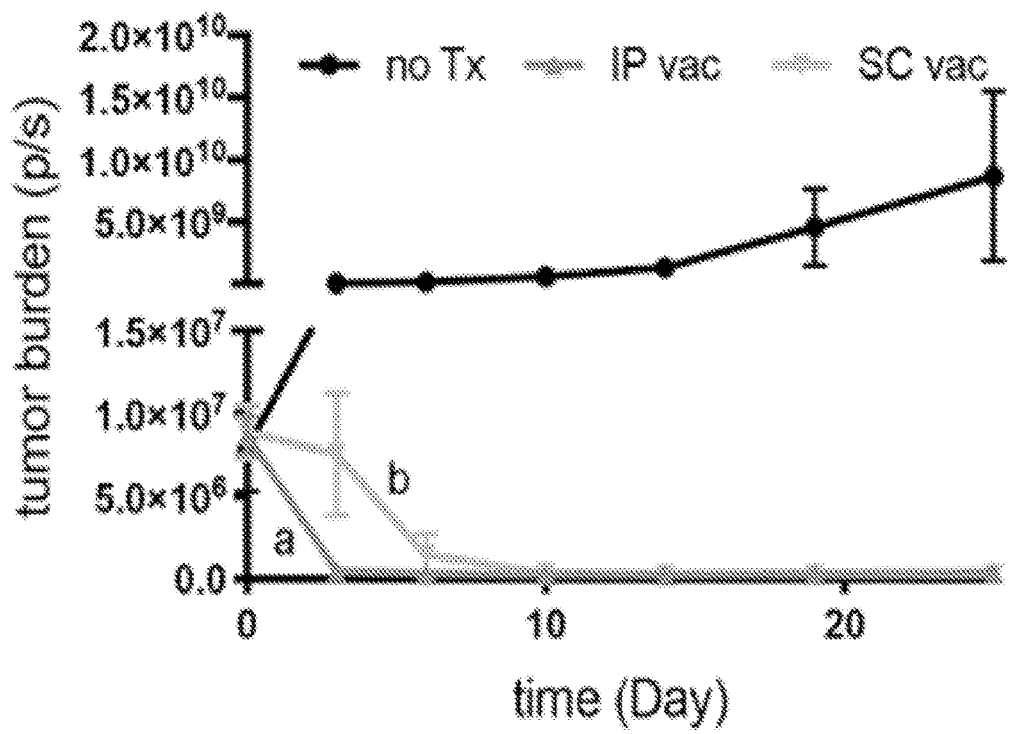
Figure 29A:
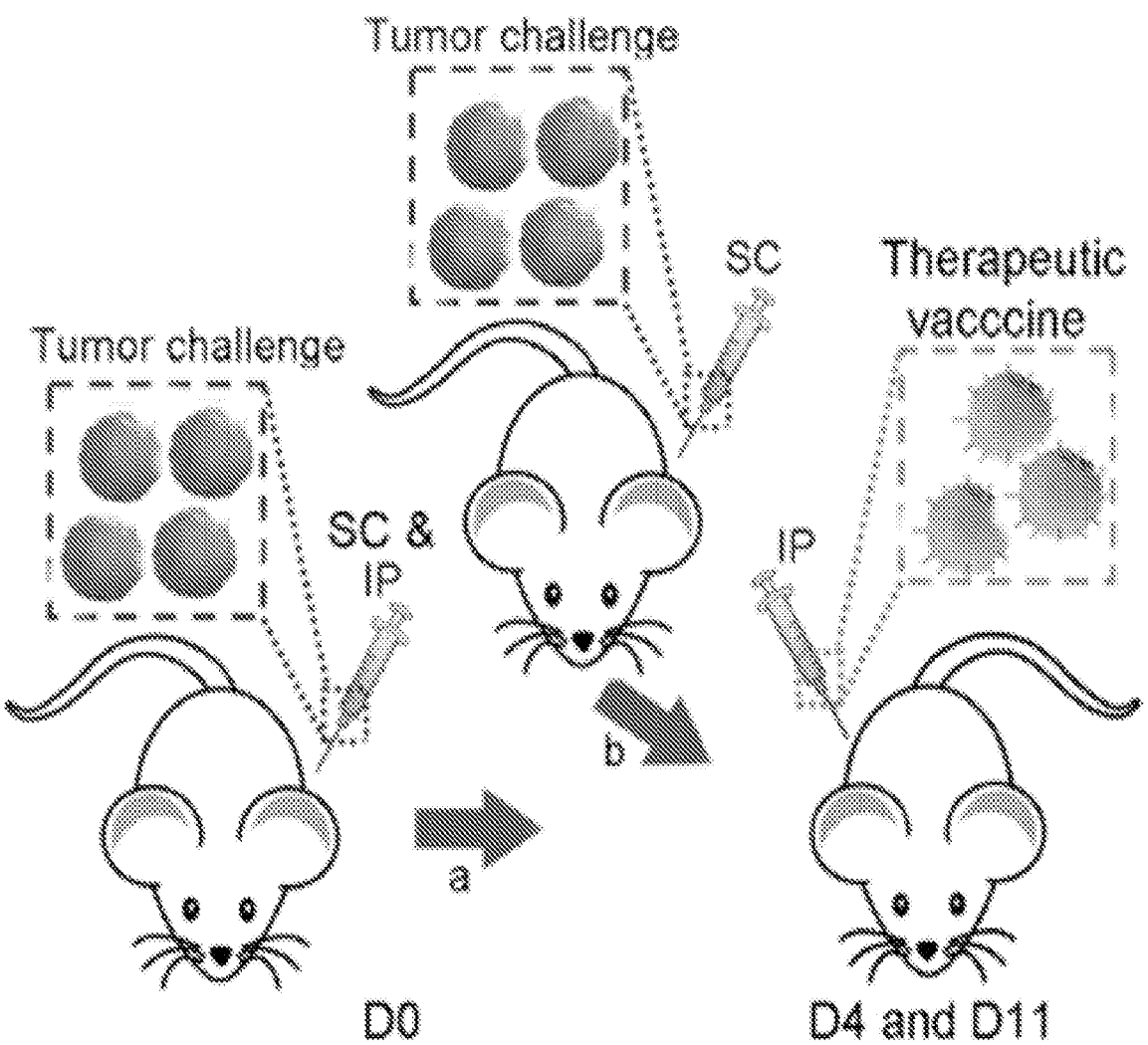
FIG. 29. Intra-tumoral intraperitoneal vaccination clears established intraperitoneal and subcutaneous tumors. (A) FVB mice were tumor challenged on Day 0 either subcutaneously or both subcutaneously plus intraperitoneally, followed by intraperitoneal vaccinations on Day 4 and Day 11, each time with $3 \times 10^6$ Si-cells. (B) Dorsal IVIS bioluminescence images of mice on select days, with ventral views included for mice with intraperitoneal and subcutaneous tumors.
Figure 29B:
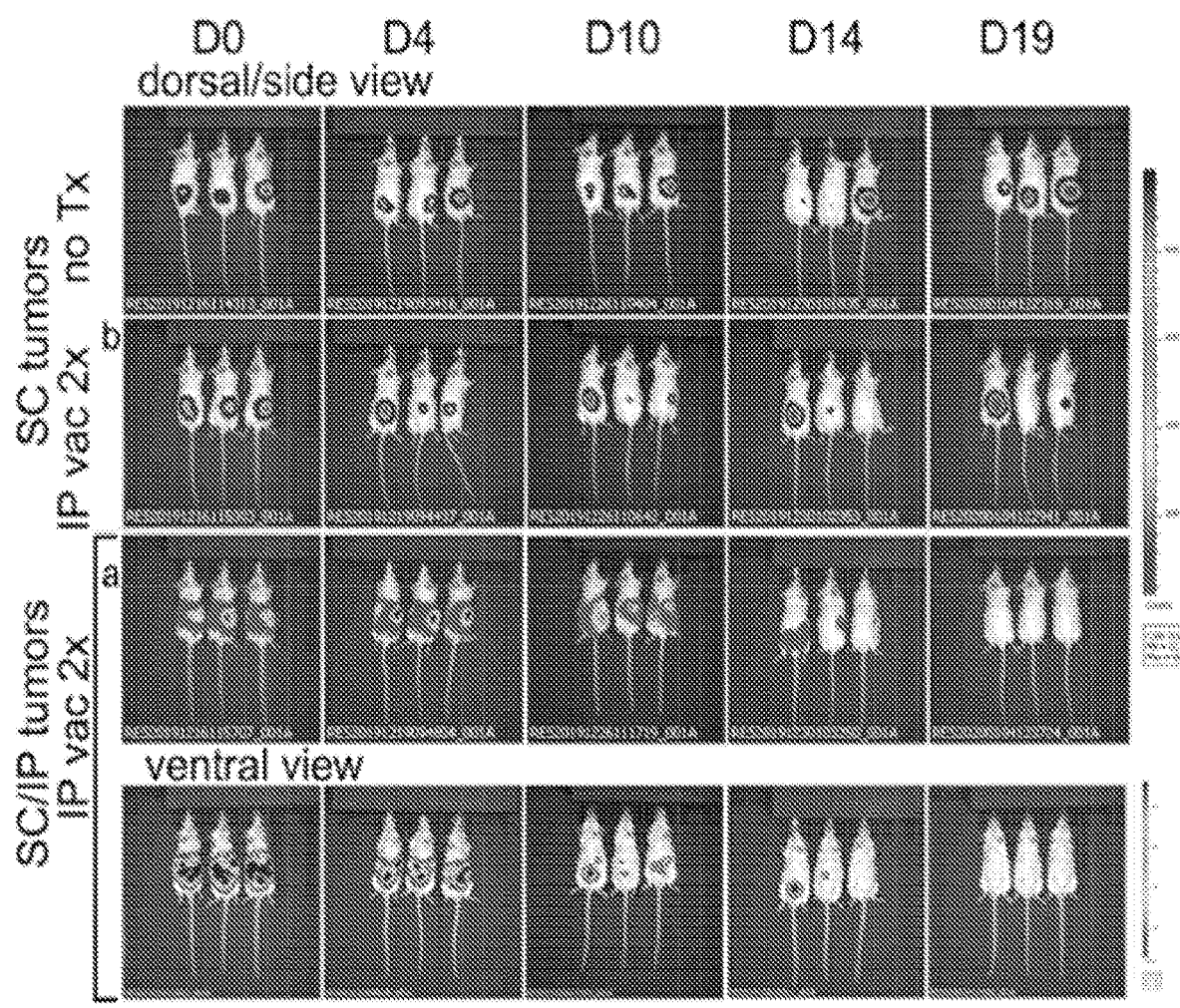

In support of Si-cells generating systemic immunological memory, naïve FVB mice were administered two subcutaneous doses of the optimized vaccine formulation three weeks prior, and two weeks prior to, intraperitoneal tumor challenge (FIG. 28A). Despite a slight delay in tumor clearance following subcutaneous administration compared to single dose intraperitoneal administration, all detectable tumor cells based on bioluminescence were eliminated in treated mice, resulting in durable survival beyond 85 days (FIG. 28B). Furthermore, intraperitoneal vaccination was able to clear established subcutaneous tumors when tumor cells were also present in the peritoneal cavity (FIG. 29A, 29B). Lastly, in support of the immunogenicity of Si-cells in clearing established tumors, intraperitoneal vaccination was compared to free adjuvant administration, the latter failing to clear tumors in the majority of mice.

Figure 6A:
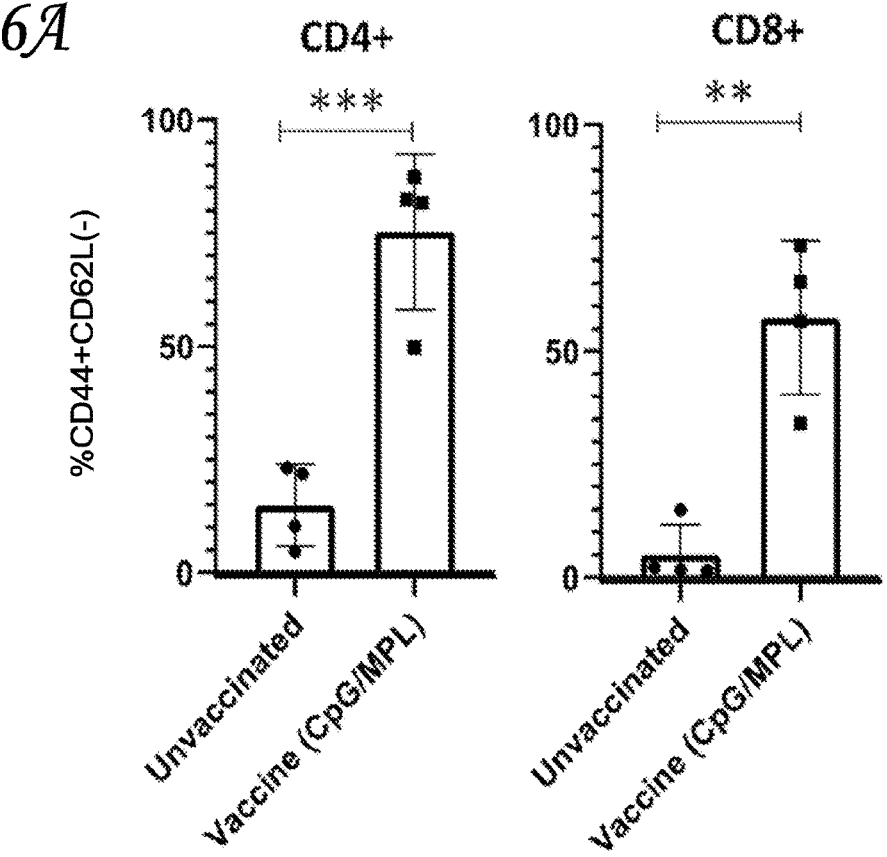
FIG. 6. Vaccination with silicified cells plus MPL/CpG enriches effector cells and IFN-γ production in the peritoneal cavity. (A) Flow cytometry of the percent of peritoneal $CD8^+$ and $CD4^+$ cell with an effector phenotype ($CD44^+$ $CD62L^-$) in mice with and without Si plus MPL/CpG vaccination. Graph shows that vaccination increases the percent of peritoneal effector cells. (B) The percent of peritoneal $CD8^+$ and $CD4^+$ cell with functional capacity based on IFN-γ expression in mice with and without Si+MPL/CpG vaccination. Vaccination enriches the proportion of peritoneal T cells expressing IFN-γ. (P value: *<0.05, <0.005, *<0.0005).
Figure 6B:
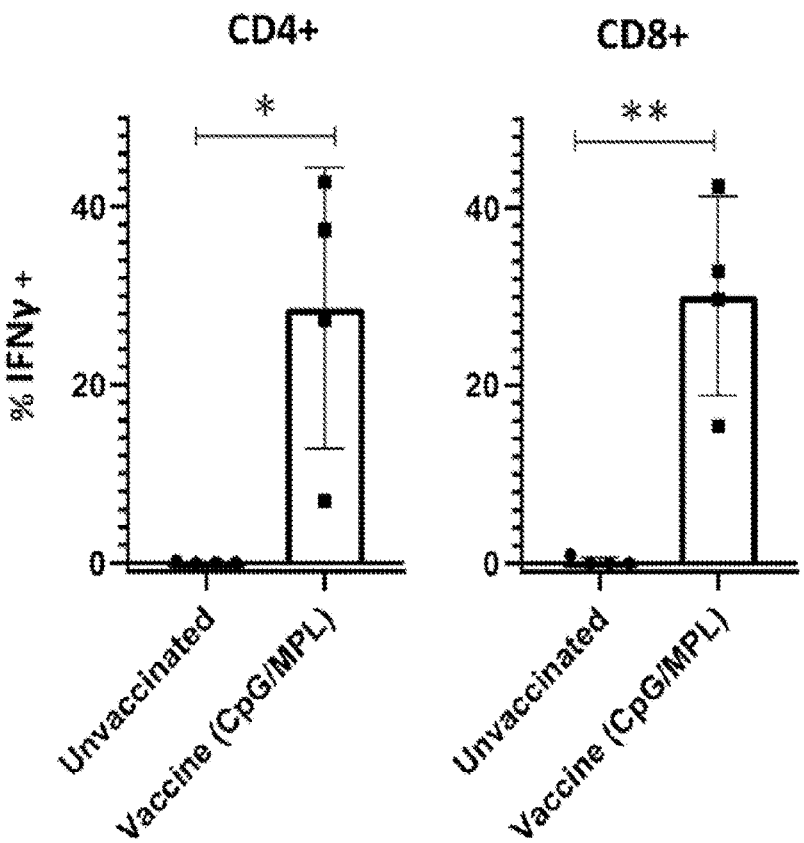
Figure 22C:
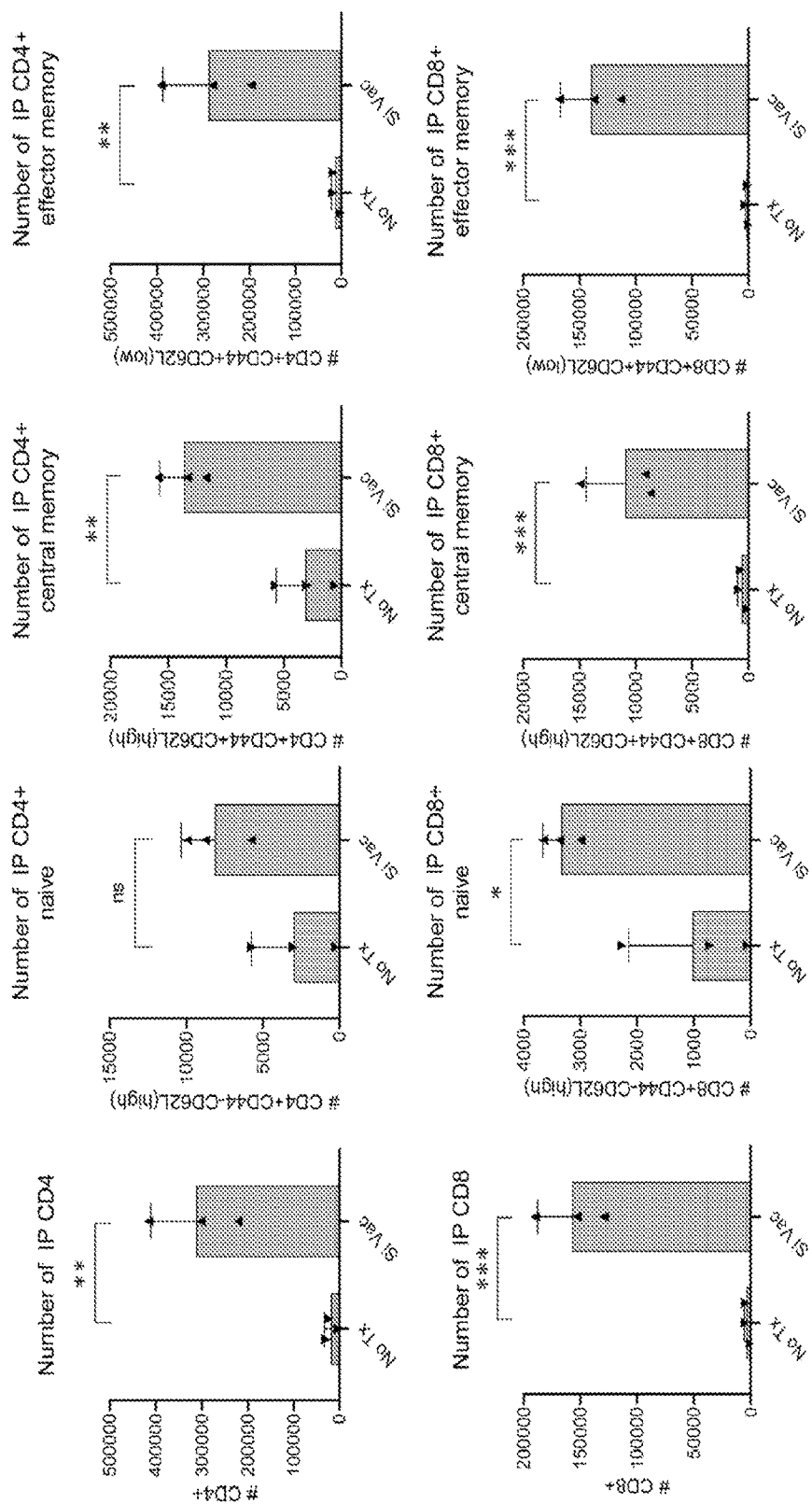
FIG. 22. Therapeutic benefit of vaccination is associated with significant changes in tumor-associated lymphocytes. Flow cytometry was used to define changes in peritoneal T cell type and activation status following vaccination. (A) Female FVB mice were intraperitoneally injected with 2e5 BR5-Akt-Luc2 cancer cells on Day 0, vaccinated on Days 4 and 11 with 3e6 BR5-Akt vaccine cells (Si Vac) or vehicle PBS (no Tx), and peritoneal fluid/wash was collected for analysis on Day 25. (B) Percent of intraperitoneal CD4 and CD8 T cells with naïve (CD44-CD62L(high)), central memory (CD44+CD62L(high)), and effector memory (CD44+CD62L(low)) phenotypes. (C) Number of intraperitoneal CD4 and CD8 T cells with naïve (CD44-CD62L (high)), central memory (CD44+CD62L(high)), and effector memory (CD44+CD62L(low)) phenotypes.
Figure 23A:
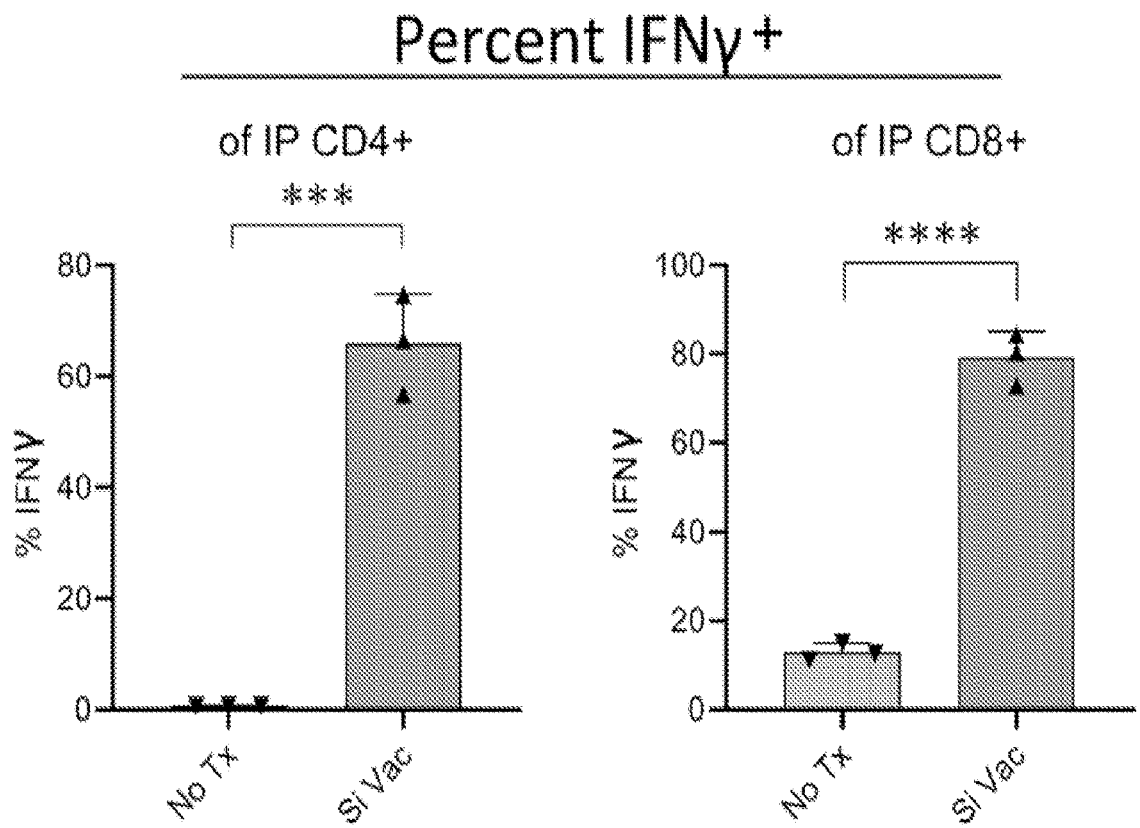
FIG. 23. Therapeutic benefit of vaccination is associated with significant changes in tumor-associated lymphocytes. (A) Percent of CD4 and CD8 cells expressing IFN-γ after re-stimulation with PMA/ionomycin. (B) Percent of IP CD4 cells expressing regulatory T cell markers FoxP3 and CTLA4. *$p<0.05$, $p<0.01$, *$p<0.001$.
Figure 23B:
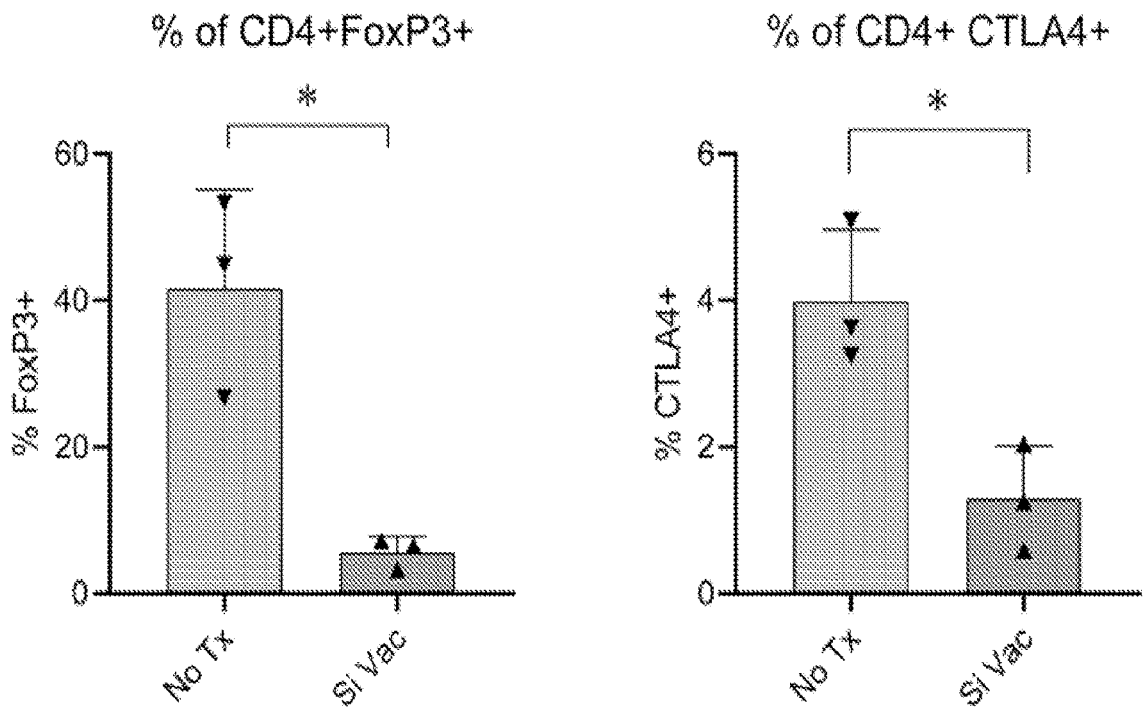

FIG. 6 shows that vaccination with Si+MPL/CpG results in the intraperitoneal enrichment of functional effector cells, which indicates that the vaccine induces a strong immune response and suggests a potential mechanism for the anti-tumor efficacy. Vaccination significantly modulates the functional status of tumor-associated lymphocytes. Flow cytometric analysis of immune cell phenotypes in the tumor microenvironment was performed to study mechanisms underlying vaccine efficacy. FVB mice with established BR5-Akt-Luc2 tumors were vaccinated with the protocol established above and euthanized on Day 25 to collect tumor-associated leukocytes for phenotypic and functional analyses. Based on previously published work demonstrating that peritoneal leukocytes are representative of tumor-infiltrating leukocytes (Flies et al., 2016, *Front Immunol* 7:581), the composition and activation status of lymphocytes in peritoneal washings of vaccinated mice were compared to untreated controls. Vaccinated mice had a significant increase in the total number of T cells and a marked increase in the proportion of effector memory cells among both $CD4^+$ and $CD8^+$ populations in the peritoneal tumor environment (FIG. 22, FIG. 23). In contrast, both the number and proportion of immune suppressive regulatory T cells decreased in vaccinated mice, illustrating substantial remodeling of the tumor immune microenvironment. Confirming the Th1 skewing expected with TLR4 an TLR9 engagement, a significant increase in CD4 and CD8 cells producing IFN-γ following ex vivo stimulation was noted in vaccinated mice. In keeping with the enhanced tumor control observed with two doses of $3 \times 10^6$ Si-tumor cells, analysis of tumor-associated lymphocytes using this dosing and schedule showed the most beneficial changes in the tumor microenvironment. These findings illustrate that vaccination with Si-PEI-CpG-MPL cells reverses the suppressive immune conditions in the tumor microenvironment and, in doing so, support tumor clearance.

Figure 7A:
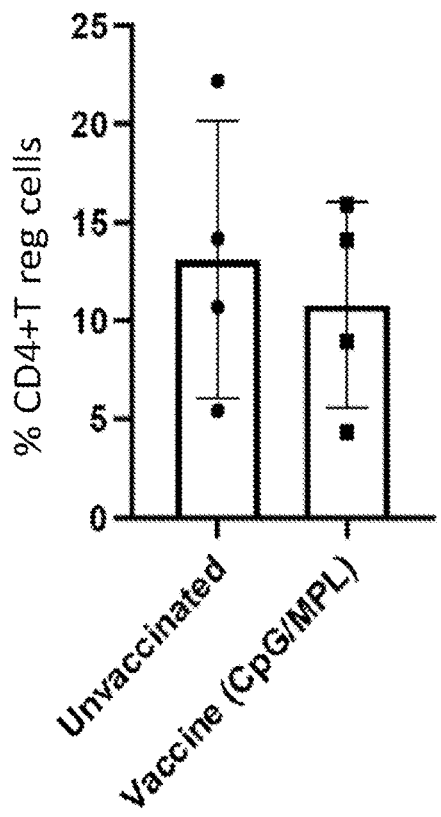
FIG. 7. Vaccination with silicified cells plus MPL/CpG does not change the proportion of regulatory T cells, macrophages, or MDSCs. (A) No change in the proportion of CD4+ peritoneal cells that are $FoxP3^+$ $CD4^+$ regulatory cells (y-axis). (B) No proportional change in peritoneal F4/80 macrophages. (C) No proportional change in peritoneal myeloid-derived suppressor cells (MDSCs).
Figure 7B:
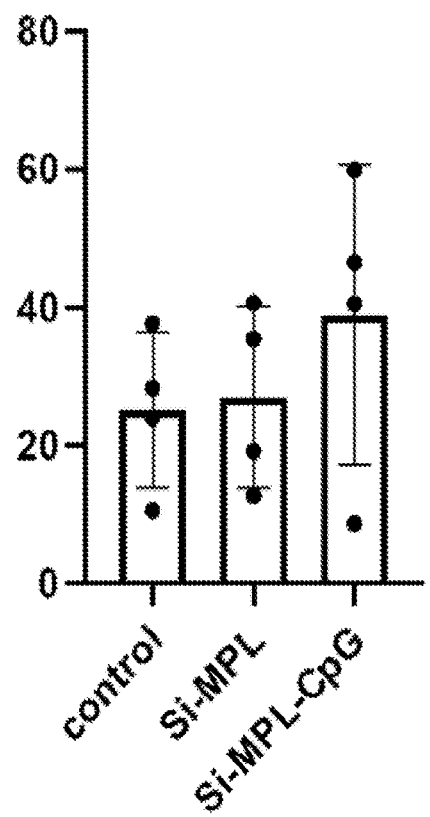
Figure 7C:
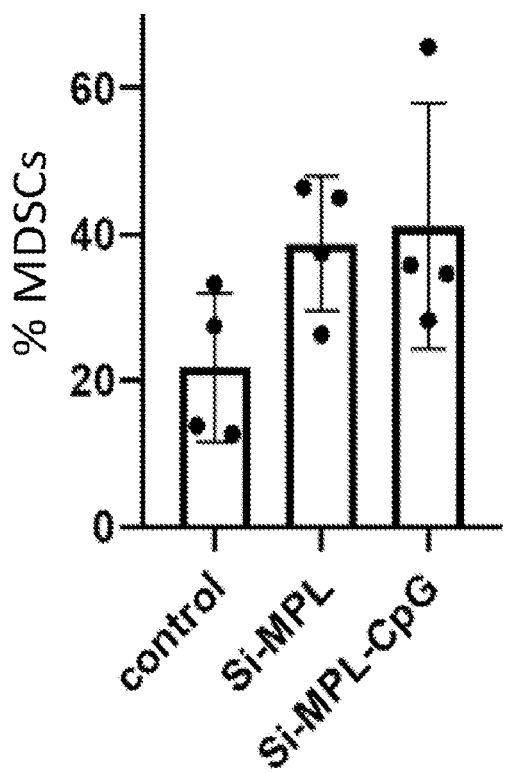

FIG. 7 indicates that the mechanism of action for the vaccine is not through altering pro-inflammatory macrophages or inhibitory immune subsets. However, other ligand combinations may provide immune benefits through these immune subsets.

Figure 8:
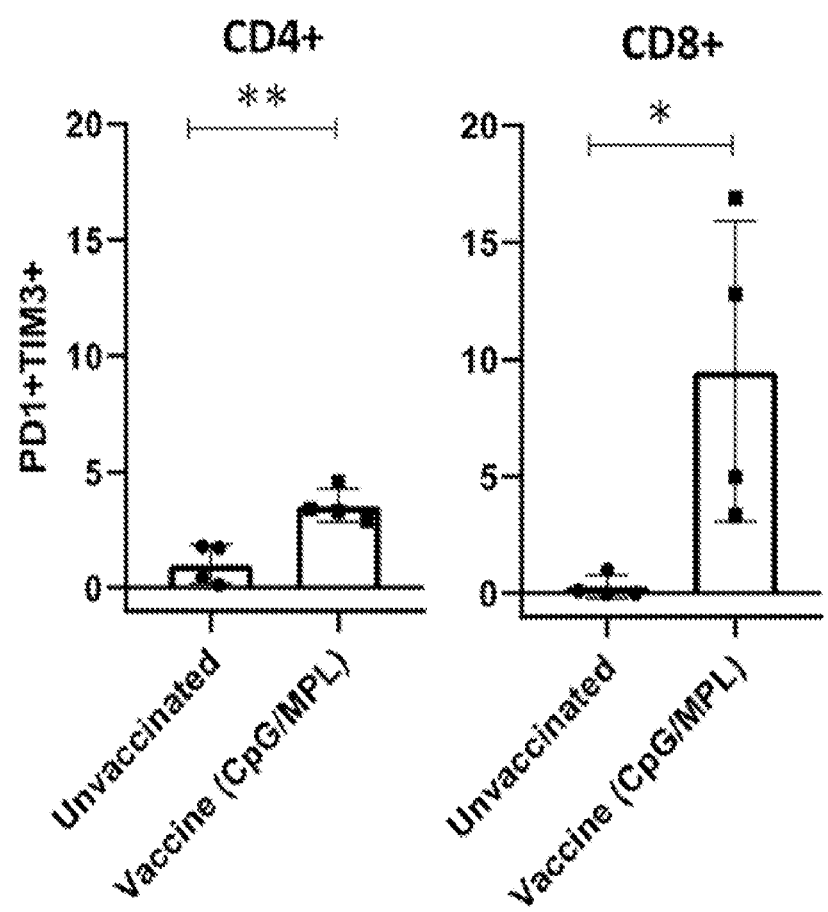
FIG. 8. Vaccination with silicified cells plus MPL/CpG increases expression on immune checkpoint inhibitors. Using flow cytometry we found mice vaccinated with Si plus MPL/CpG had increased expression of immune checkpoint inhibitors PD1 and TIM3 on $CD4^+$ and $CD8^+$ cells.
Figure 9:
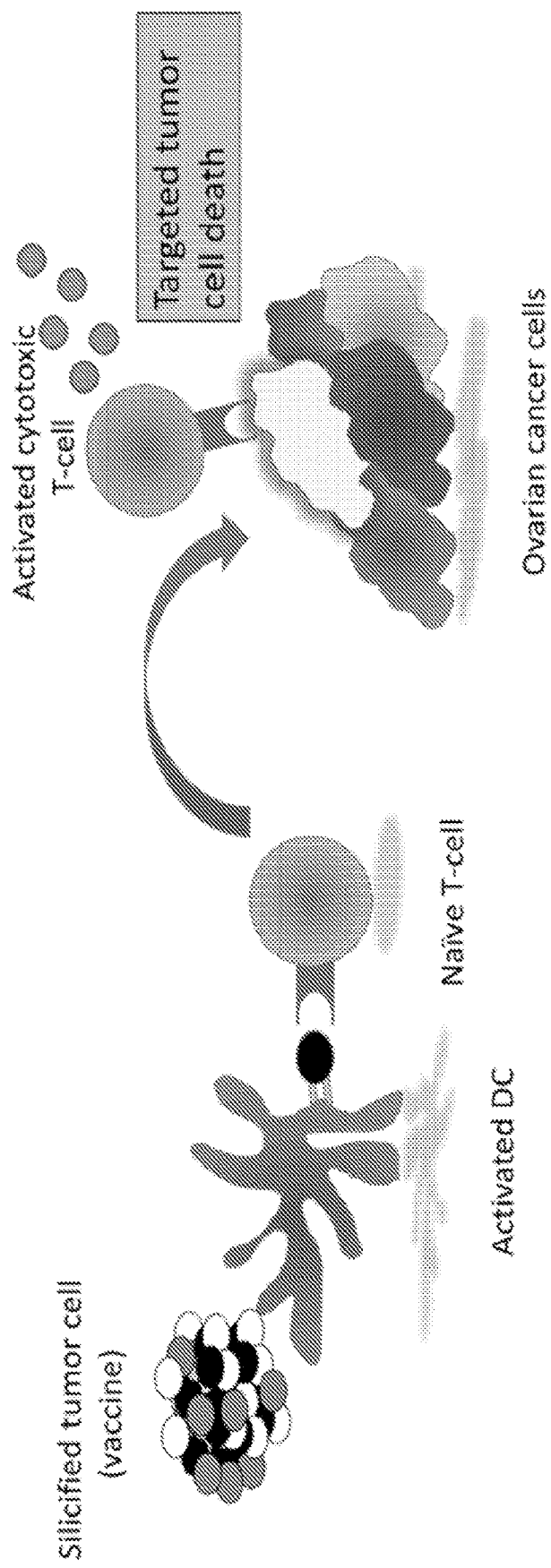
FIG. 9. Silicified tumor cell activation of DC-mediated T cell activation and tumor killing. Silicified tumor cells coated with pathogen-associated molecular patterns induce DC activation resulting in antigen uptake, processing, and presentation in vitro. Activated anti-tumor T cells have effector phenotypes and produce IFN-γ.
Figure 10A:
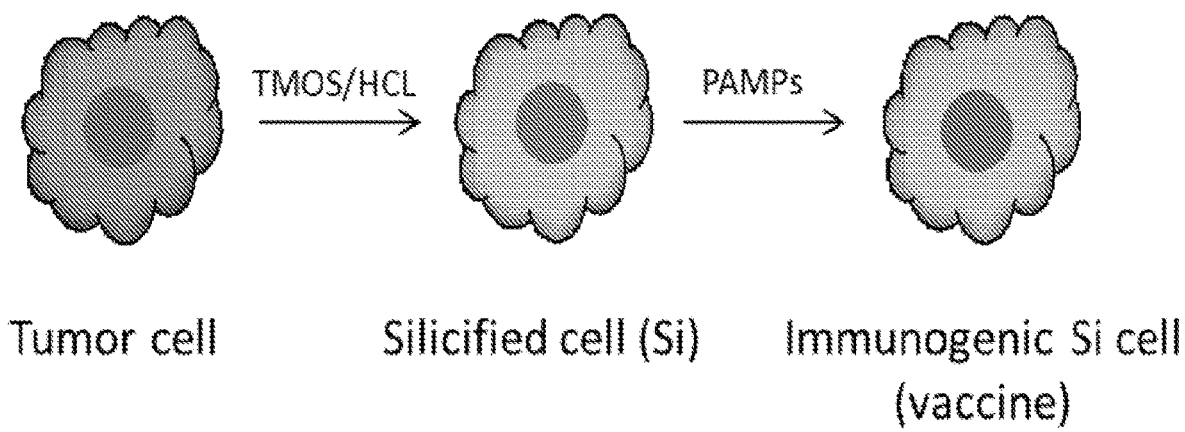
FIG. 10. Process of silicifying tumor cells. (A) Illustration of the general process to silicify a tumor cell. A tumor cells is subjected to silicification to produce a silicified cell. Silicified cells are non-viable, highly stable, and retain a full tumor antigen repertoire. The surface of the silicified cell can then be decorated with pathogen-associated molecular patterns (PAMPs), thereby enhancing immunogenicity of the silicified cell. (B) Scanning electron microscopy (SEM) images of silicified tumor cells.
Figure 10B:
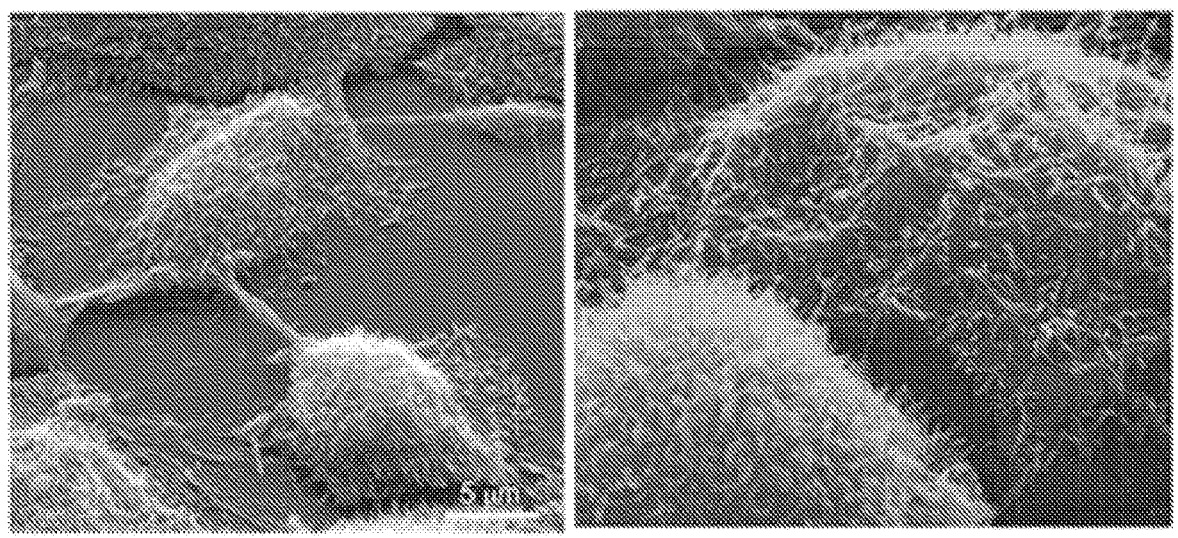

FIG. 8 shows that effective vaccination induces the upregulation of inhibitory molecules on T cells, suggesting self-regulation and T cell exhaustion. Inhibiting these regulatory pathways represents a potential approach for increasing the efficacy of the Si-MPL/CpG vaccine. (P value: *<0.05, **<0.005).

Figure 24A:
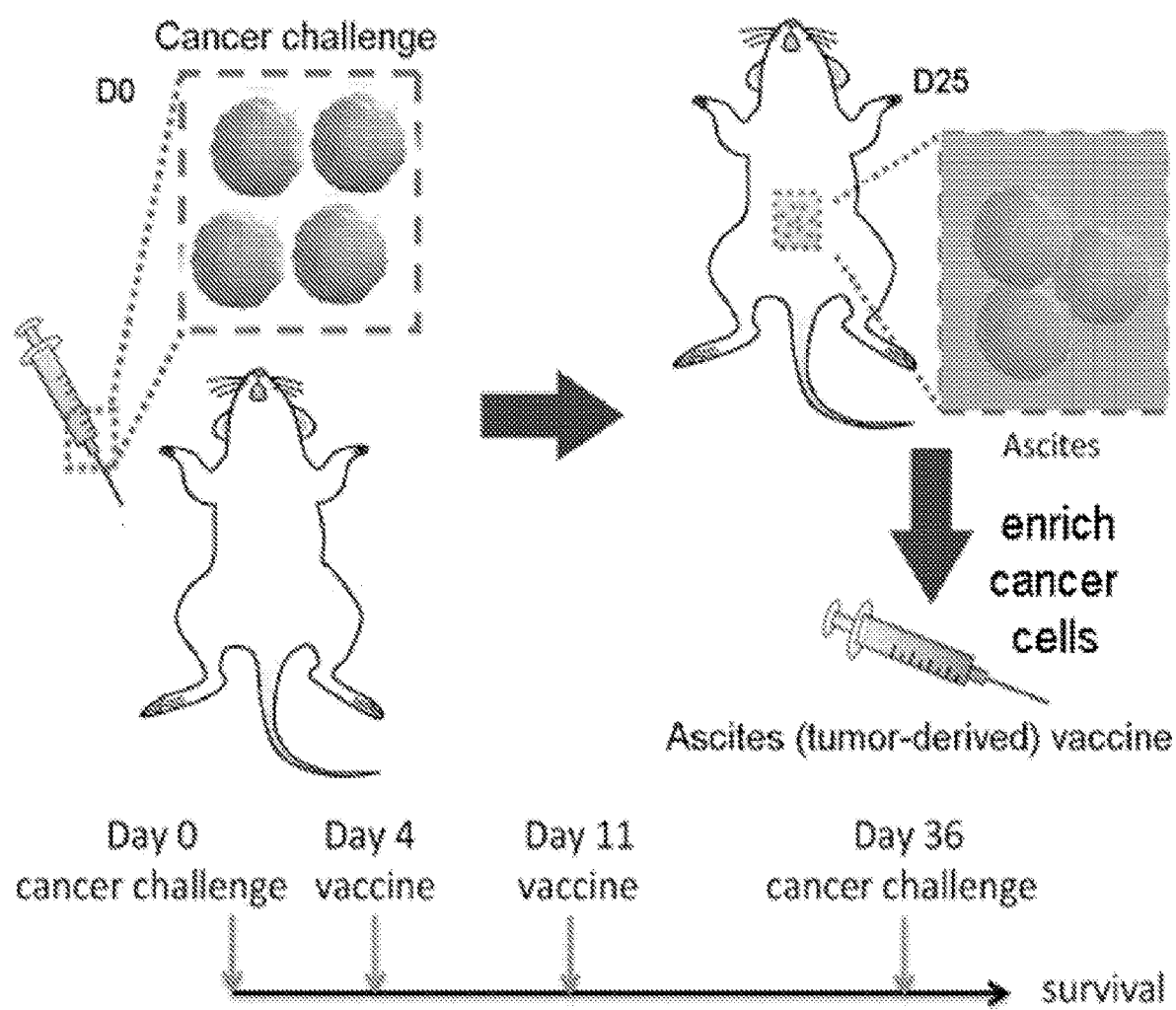
FIG. 24. Effective vaccine can be developed from ascites. (A) Treatment schedule and diagram showing vaccine preparation using ascites from a FVB mouse with late stage BR5-Akt ovarian cancer. (B) Flow cytometry histograms of human or mouse ascites, or mouse solid tumor cells (Ep-CAM$^+$) before and after filtration enrichment. (C) Tumor burden in mice intraperitoneally vaccinated on Day 4 and Day 11 with cell line (BR5 vac) or ascites vaccines (n=4). (D) Kaplan-Meier survival curves. (E) IVIS Spectrum bioluminescent images. To test immunological memory, vaccinated mice were re-challenged with BR5-Akt-Luc2 tumor cells on Days 36.
Figure 24B:
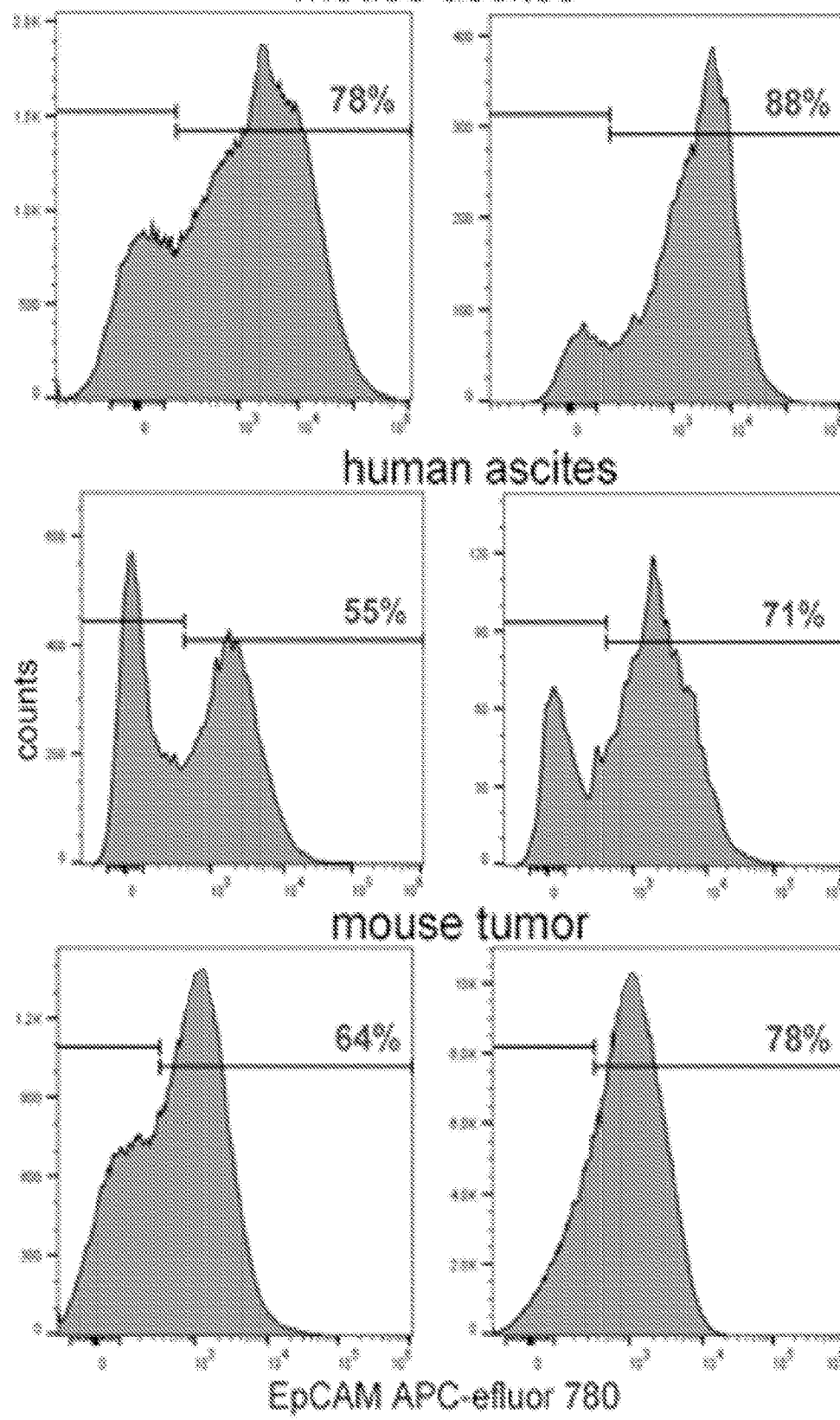
Figure 24C:
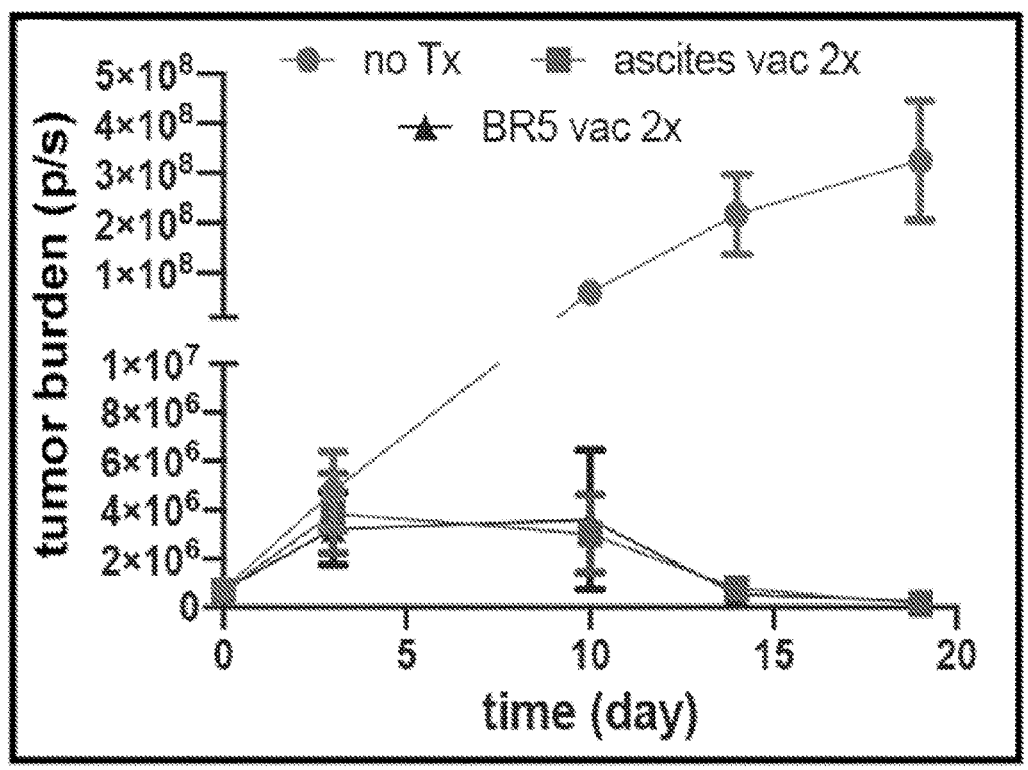
Figure 24D:
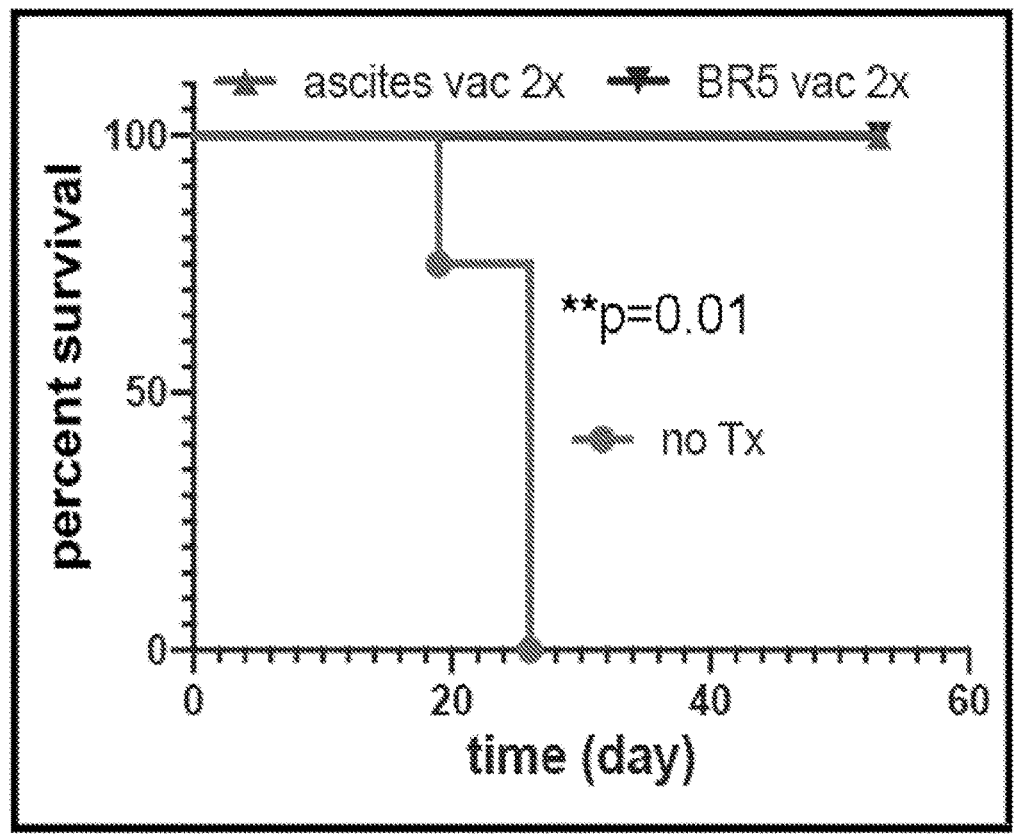
Figure 24E:
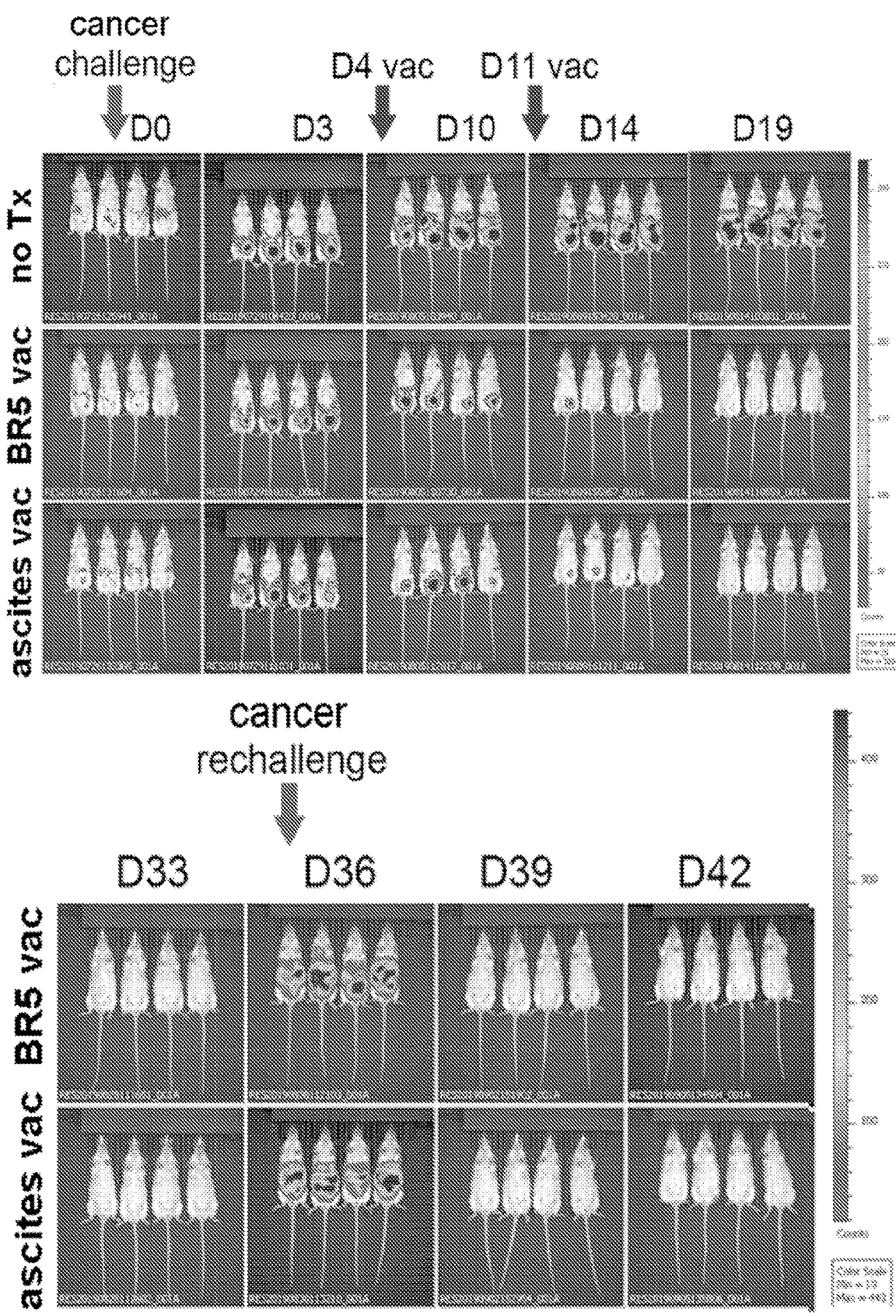
Figure 25:
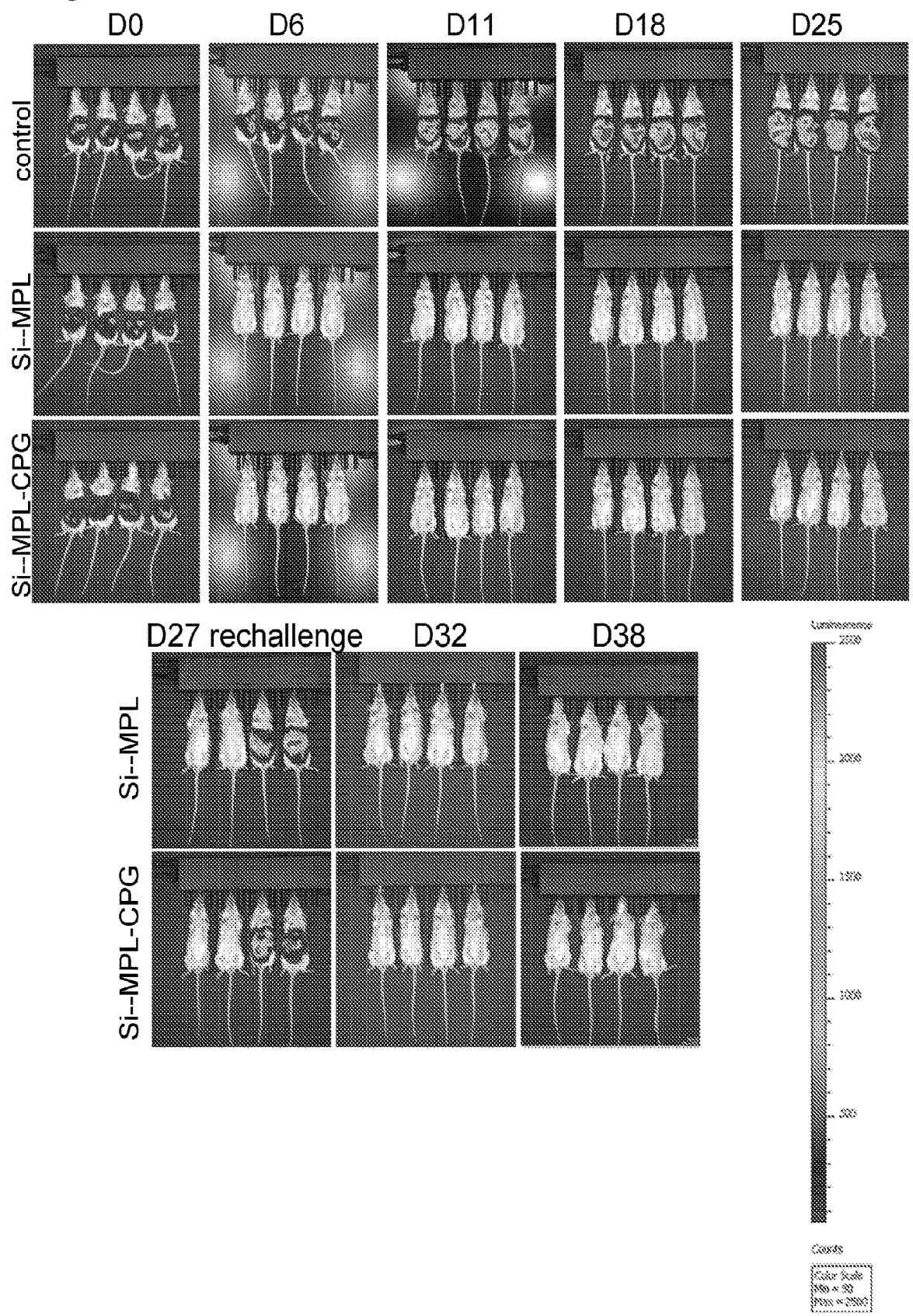
FIG. 25. Weekly bioluminescence imaging of mice from the experiment shown in FIG. 19 and FIG. 20 using the IVIS Spectrum following intraperitoneal luciferin injection demonstrate efficacy against tumor engraftment in mice vaccinated with MPL or MPL plus CpG biomineralized cancer cells.

Ascites can be used for Si-tumor cell vaccine development. Creating silicified tumor cell vaccines for cancer patients can involve using autologous tumor cells. Clinically, ovarian cancer presents at late stages of disease when patients have metastases throughout the peritoneal cavity and accumulation of malignant ascites. Ascites fluid is rich in tumor spheroids, simplifying cancer cell enrichment. To test the feasibility of using ex vivo samples for vaccine production, ascites cells were collected from mice with late-stage BR5-Akt tumors for silicification (FIG. 24A). Ascites tumor cells were enriched by filtration capture and silicified using the protocol developed with cancer cell lines. Notable, human and mouse ascites pre-enrichment and post-enrichment displayed similar percentages of $EpCAM^+$ tumor cells (FIG. 24B). The efficacy of the ascites cell vaccine administered was compared with vaccination using silicified tumor cells grown in vitro using the same silicified cell dose and schedule. The therapeutic benefit of the ascites vaccine was equivalent to the cell line vaccine, inducing durable therapeutic effects and prophylactic effects against repeat tumor challenge (FIG. 24C, 24D, 24E). These results demonstrate that vaccine production is feasible using available tumor samples to create personalized vaccines.

Treatment with silicified tumor cells is not associated with significant immune-related toxicity. To determine whether vaccination with silicified tumor cells was associated with any immune toxicity, blood and tumor samples were evaluated in untreated and vaccinated mice. No consistent significant changes in CBC, hemoglobin, or platelet levels were observed in vaccine recipients. Slight differences in neutrophil numbers were assessed to not be clinically significant. Importantly, assays of renal and hepatic function showed no significant change with vaccination. Finally, none of the vaccinated mice developed rash, alopecia, diarrhea, or weight loss suggestive of autoimmune disease.

Histopathologic analysis performed by a board-certified veterinary pathologist showed pronounced necrosis in small residual islands of tumor in vaccinated mice. These subclinical implants were associated with marked immune cell infiltration. Similarly, higher numbers of leukocytes were noted in peritoneal tissue samples from vaccinated mice but no evidence of suppurative peritonitis was found. Overall, vaccination resulted in tumor necrosis and increased lymphocyte infiltration as expected, with no indication of autoimmune disease.

Collectively, these results show that vaccination with silicified cancer cells coated in MPL/CpG is an effective strategy to block tumor engraftment and/or reduce tumor burden in a pre-clinical model of ovarian cancer. Moreover, the data in FIG. 7 and FIG. 8 show that a vaccine containing immunogenic silicified cells increases PD-1 and TIM3 expression. Thus, in some embodiments, the vaccine may be combined with an agent that blocks immune suppression— e.g., a checkpoint blockade antibody or other agent that blocks immune suppression.

Silicified cells can be used as a modular vaccine platform for personalized immune therapy that demonstrates durable therapeutic efficacy. The silicified cell vaccine platform provides advantages over existing cell-based vaccines, including, but not limited to: preserved personalized antigens (e.g., tumor antigens), surface binding capacity for localized delivery of immune adjuvants, activation of both innate and adaptive immunity, potent therapeutic efficacy without demonstrated toxicity, and simplified production and storage requirements for broader accessibility.

Cell silicification as a method of cell fixation represents a major advance in the ability to engineer cells to safely deliver target antigens. Because the silica surface is highly absorbent and readily binds adjuvants such as lipopolysaccharide and monophosphoryl lipid A, silicified cells acquire surface functionalization that can be exploited to direct specific immune responses. Coating silicified cancer cells with TLR agonists successfully induced innate immune activation, demonstrating enhanced internalization and processing by dendritic cells. Notably, dendritic cells s possess a unique mechanism for phagosome maturation, maintaining the phagosome at an alkaline pH of 7 to 7.5 in the first few hours after phagocytosis. During this time, dendritic cells s recruit NADPH oxidase 2 (NOX2), leading to proton consumption by oxygen radicals and cell neutralization to facilitate peptide loading onto MHC molecules. These same conditions also favor silica hydrolysis, facilitating dissociation of silicified cells. Adsorption of PEI to silica further promotes silica degradation at neutral and acidic pH due to pH buffering.

Further, data presented herein demonstrate that dendritic cell activation in response to the vaccine is associated with the induction of tumor-specific adaptive immunity and is effective against secondary tumor challenge. The silicified cell surface can bind a broad array of molecules or drugs, presenting diverse opportunities for immunomodulation and targeted therapy. The choice of surface-bound adjuvant could be based on an individual patient's response to treatment or tailored for the immune landscape of a patient's tumor. In addition, the integration of antibodies or molecules that reverse inhibitory pathways in the tumor microenvironment can help sustain the activation of cancer-specific T cells generated in response to the vaccine.

Ovarian cancer is characterized by rapid peritoneal dissemination and a highly immunosuppressive tumor microenvironment, which may, in part, explain the limited efficacy of immune therapy in this disease. It is notable, therefore, that vaccination with the PEI-CpG-MPL vaccine, even in the immunosuppressive ovarian cancer models used herein, significantly increased the proportion of effector memory T cells while reducing the suppressive regulatory T cell subset in peritoneal samples. The substantial increase in IFN-γ production among both $CD4^+$ and $CD8^+$ T cells in response to vaccination is associated with durable treatment efficacy in ovarian cancer models (Higuchi et al., 2015, *Cancer Immunol Res* 3:1257-1268). By reversing the effects of cancer engraftment on regional lymphocytes, vaccination with the PEI-CpG-MPL cells restricts immune escape and disease recurrence for lasting survival benefit. Importantly, women with ovarian cancer typically present with widely metastatic disease, often associated with abdominal ascites. Ascites fluid can be removed percutaneously with paracentesis or evacuated at the time of tumor debulking surgery. It is not uncommon for several liters of fluid to be removed at one time, and typically most is discarded. This disclosure describes using ascites samples to develop a highly effective silicified vaccine, presenting a clinically feasible strategy for rapid vaccine development that can be integrated into standard management of this disease.

Finally, a personalized silicified vaccine can be produced within 24 hours, substantially reducing the time required for cell culture and ex vivo modification for existing cell-based vaccines. Once silicified, cells are stable at room temperature, enabling long term storage without cryopreservation. These features have the potential to address a global need for versatile vaccines with the potential to reduce existing disparities in access to immune therapy(e.g., cancer immunotherapy). As a result, the silicified cell platform can transform both the production and distribution of vaccines and facilitate the integration of immunotherapy into treatment protocols.

Thus, in one aspect, this disclosure describes a vaccine platform that takes into account biological targets, mechanisms of antigen presentation by dendritic cells, and T cell activation. The modular platform can be loaded with unique molecules to drive diverse responses, both within or on the silicified cell surface. Delivering a silicified cell vaccine directly to the tumor microenvironment reprograms the suppressive milieu, supporting the development of antitumor immune responses and immunological memory.

In another aspect, this disclosure describes a pharmaceutical composition (e.g., a vaccine) that includes an immunogenic silicified cell and method of preparing immunogenic silicified cells. The ability to silicify, for example, cancer cells and modify the surface with pathogen-derived immunogenic molecules results in enhanced activation and internalization by dendritic cells. Silicified cells can be designed to mimic pathogens, thereby enhancing a subject's immune response to the silicified cell, driving immune responses against patient-specific antigens.

As used herein, "immunogenic silicified cell" refers collectively to a silicified cell or a silicified cell fragment or silicified cell-derived body, such as, for example, a silicified exosome, a silicified microvesicle, or a silicified apoptotic body. Exemplary tumor cells include cells derived from patient tumors (autologous or allogenic), blood, ascites, or established tumor cell lines. The composition may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with an immunogenic silicified cell without causing any undesirable biological effects or interacting in a deleterious manner with any of the other components of the pharmaceutical composition in which it is contained.

An immunogenic silicified cell may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical can be administered via a sustained or delayed release.

Thus, an immunogenic silicified cell may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, solution and the like. The formulation may further include one or more additives including such as, for example, an adjuvant. Exemplary adjuvants include, for example, pathogen-associated molecular patterns (PAMPs), such as Toll-like receptor (TLR) ligands, damage-associated molecular patterns (DAMPs), cytokines, proteins, carbohydrates, lectins, Freund's adjuvant, aluminum hydroxide, or aluminum phosphate.

A formulation may be conveniently presented in unit dosage form and may be prepared by methods well known in the art of pharmacy. Methods of preparing a composition with a pharmaceutically acceptable carrier include the step of bringing the immunogenic silicified cell into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of immunogenic silicified cell administered can vary depending on various factors including, but not limited to, the specific silicified cell being administered, the weight, physical condition, and/or age of the subject, and/or the route of administration. Thus, the absolute amount of immunogenic silicified cell included in a given unit dosage form can vary widely, and depends upon factors such as the species, age, weight and physical condition of the subject, and/or the method of administration. Accordingly, it is not practical to set forth generally the amount that constitutes an amount of immunogenic silicified cell effective for all possible applications. Those of ordinary skill in the art, however, can readily determine the appropriate amount with due consideration of such factors.

In some embodiments, the method can include administering sufficient immunogenic silicified cells to provide a dose of, for example, from about 50 silicified cells/kg to about $1 \times 10^{10}$ silicified cells/kg to the subject, although in some embodiments the methods may be performed by administering the immunogenic silicified cells in a dose outside this range. In some of these embodiments, the method includes administering sufficient immunogenic silicified cells to provide a dose of from about 100 silicified cells/kg to $1 \times 10^9$ silicified cells/kg to the subject, for example, a dose of from about 1000 silicified cells/kg to about 10,000 silicified cells/kg.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2 = (wt\ kg^{0.425} \times height\ cm^{0.725}) \times 0.007184$.

In some embodiments, immunogenic silicified cells may be administered, for example, from a single dose to multiple doses per week, although in some embodiments the method can be performed by administering immunogenic silicified cells at a frequency outside this range. In certain embodiments, immunogenic silicified cells may be administered from about once every six months to about three times per week.

The silicified cells described herein can be used to treat a subject having, or at risk of having, a condition for which treatment is intended. That is, the treatment may be therapeutic or prophylactic. Treatment that is prophylactic—e.g., initiated before a subject manifests a symptom or clinical sign of the condition for which treatment is intended such as, for example, while an infection remains subclinical—is referred to herein as treatment of a subject that is "at risk" of having the condition. As used herein, the term "at risk" refers to a subject that may or may not actually possess the described risk. Thus, for example, a subject "at risk" of developing a tumor is a subject possessing one or more risk factors associated with developing the tumor such as, for example, genetic predisposition, ancestry, age, sex, geographical location, lifestyle, or medical history. As another example, a subject "at risk" of an infectious condition is a subject present in an area where individuals have been identified as infected by the microbe that causes the condition and/or is likely to be exposed to the microbe that causes the condition even if the subject has not yet manifested any detectable indication of infection by the microbe that causes the condition and regardless of whether the subject may harbor a subclinical amount of the microbe that causes the condition.

Accordingly, a composition can be administered before, during, or after the subject first exhibits a symptom or clinical sign of the condition for which treatment is intended. Treatment initiated before the subject first exhibits a symptom or clinical sign of the condition may result in decreasing the likelihood that the subject experiences clinical evidence of the condition compared to a similarly situated subject to whom the composition is not administered, decreasing the severity of symptoms and/or clinical signs of the condition, and/or completely resolving the condition. Treatment initiated after the subject first exhibits a symptom or clinical sign of the condition for which treatment is intended may result in decreasing the severity of symptoms and/or clinical signs of the condition compared to a similarly situated subject to whom the composition is not administered, and/or completely resolving the condition.

Thus, the method includes administering an effective amount of the composition to a subject having, or at risk of having, a condition for which treatment is intended. In this aspect, an "effective amount" is an amount effective to reduce, limit progression, ameliorate, or resolve, to any extent, a symptom or clinical sign related to the condition.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Preparation of Silicified Cells

The cells were rinsed twice with 1×PBS, once with 154 mM NaCl solution and then suspended in a silicification solution containing 10 mM TMOS, 100 mM NaCl and 1.0 mM HCl (pH 3.0). After overnight or longer silicification at −80° C., silicified cells were rinsed once with water and once with 1×PBS. The silicified cells were stored in 1×PBS before use.

Preparation of Cationic Polymer Coated Silicified Cells

The silicified cells were incubated for 30 minutes in chitosan solution (2 mg/mL in 1×PBS) or for 10 minutes in polyethylenimine (PEI) solution (0.2 mg/mL in 1×PBS; or 0.05-1 mg/ml for titration) under constant rotation. The cationic polymer coated silicified cells were washed with 1×PBS and resuspended in 1×PBS.

Zeta Potential Measurements

Zeta potential measurements were made using a ZETASIZER NANO-ZS analyzer (Malvern Panalytical, Inc., Westborough, MA) equipped with a He—Ne laser (633 nm) and non-invasive backscatter (NIBS) optics. The samples for zeta potential measurements were suspended in 10 mM NaCl solution. All reported values correspond to the average of at least three independent samples.

Scanning Electron Microscopy (SEM) Imaging

The morphology of samples were characterized using scanning electron microscope (SEM). SEM samples were prepared by drop casting. Briefly, all samples were suspended in water, and then dropped onto 5×5 mm glass slides. The glass slides were then mounted on SEM stubs using conductive adhesive tape (PELCO TABS, 12 mm OD; Ted Pella, Inc., Redding, CA). Samples were sputter coated with a 10 nm layer of gold using a sputtering system (CRC-150, Torr International, Inc., New Windsor, NY). SEM images were acquired under high vacuum, at 10 kV, using an FEI Quanta series scanning electron microscope (Thermo Fisher Scientific, Waltham, MA).

Cell Viability Assay

Cell culture was performed using standard procedures. ID8 and BR5akt cells were maintained in the DMEM media containing 10% FBS at 37° C. and 5% $CO_2$. Cells were passaged at approximately 70% confluency. Mouse bone marrow dendritic cells were maintained in the RPMI media containing 10% FBS, 50 µM beta mercaptoethanol, and 20 ng/ml GM-CSF at 37° C. and 5% $CO_2$. For cell viability assays, 100 µL of cell suspension (100,000 cells/mL) were seeded into a white opaque 96-well plate and cultured for 24 hours at 37° C. The cells were then incubated with 100 µL of different concentrations of silicified cells, polymer-coated silicified cells, and polymer-coated silicified cells with monophosphoryl lipid A (MPL). After 24 hours incubation, 100 µL of CELLTITER-GLO 2.0 reagent (Promega Corp., Madison, WI) was added into each well and incubated for 10 minutes at room temperature. The luminescence readings were then obtained/recorded using microplate reader (BioTek Instruments, Inc., Winooski, VT). The percent cell viability was calculated relative to the control non-treated cells.

Epithelial ovarian cancer is frequently diagnosed at late stages, with tumors found throughout the peritoneal cavity. For in vivo murine experiments, established fully immune competent murine models, specifically ID8-ova (Roby et al., *Carcinogenesis* 21:585-591, 2000) and the BR5-Akt Luc2 BRCA-1 deficient (Xing et al., *Cancer Res* 66:8949-8953, 2006; Higuchi et al., *Cancer Immunol Res* 3:1257-1268, 2015) models were used. Both are models of high-grade serous epithelial adenocarcinoma, consistent with the most common type of human ovarian cancer. The BR5-Akt BRCA1-deficient epithelial ovarian cancer cell line was generated on an FVB background as previously described (Xing et al., *Cancer Res* 66:8949-8953, 2006). Following intraperitoneal inoculation with 2×10$^5$BR5-Akt cells, 6-8-week-old female mice reliably developed peritoneal carcinomatosis and ascites by day 21, mimicking the most common pattern seen in patients with ovarian cancer. Following intraperitoneal injection of ID8-ova cells, mice developed malignant ascites and tumor implants in the omentum and along peritoneal surfaces, mimicking the typical clinical presentation in patients. By expressing targetable tumor antigens, this second model permits direct analysis of tumor-specific lymphocyte function. Expression of a foreign tumor antigen does not prevent the establishment of tumor-associated T cell dysfunction. Also, peritoneal leukocyte infiltrates in these models mirror the phenotype and functional status of ascites leukocytes from women with ovarian cancer.

Prepare Biomineralized, PAMP Modified Cancer Cells

Figure 4A:
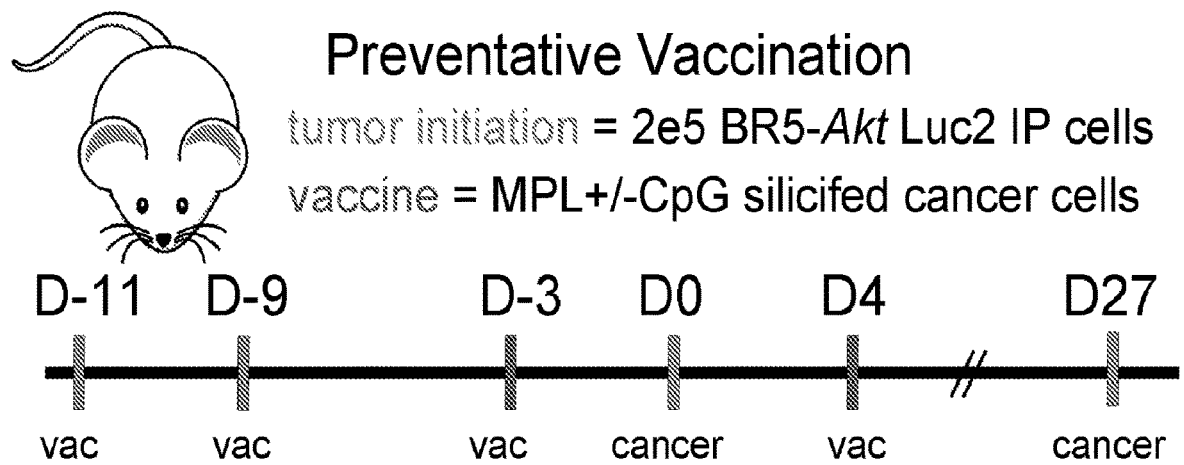
FIG. 4. Vaccination with silicified BR5-Akt Luc2 ovarian cancer cells blocks tumor engraftment in mice. Cancer cells were silicified and coated with PAMPs. A mouse model of serous epithelial ovarian cancer was used to test the efficacy of pathogen mimic cancer cells as a preventative vaccine. (A) Timeline for vaccinations and tumor challenge. (B) Weight gain as a metric for tumor progression development. (C) Day 25 average weight of mice per group. (D) Kaplan-Meier survival curves demonstrating significant survival advantage associated with vaccination.
Figure 4B:
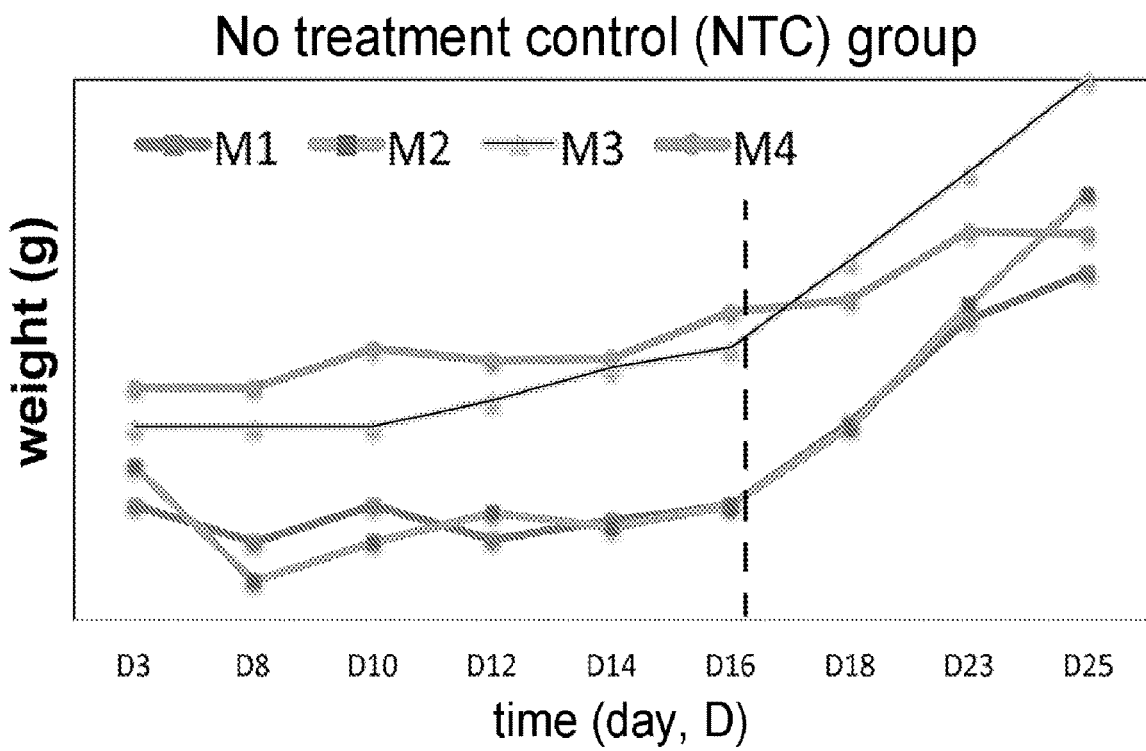
Figure 4C:
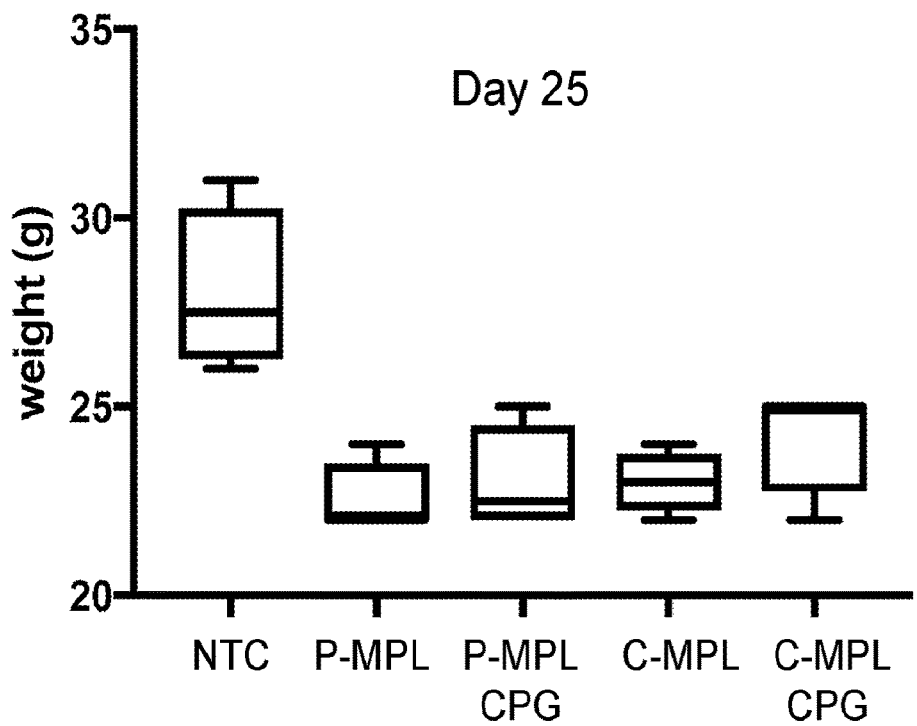
Figure 4D:
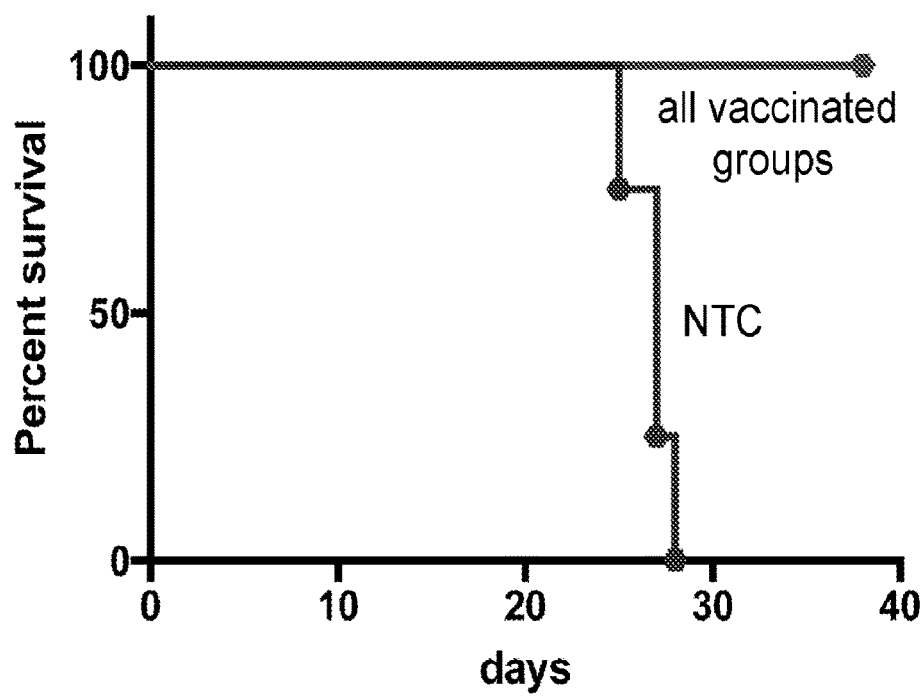
Figure 5A:
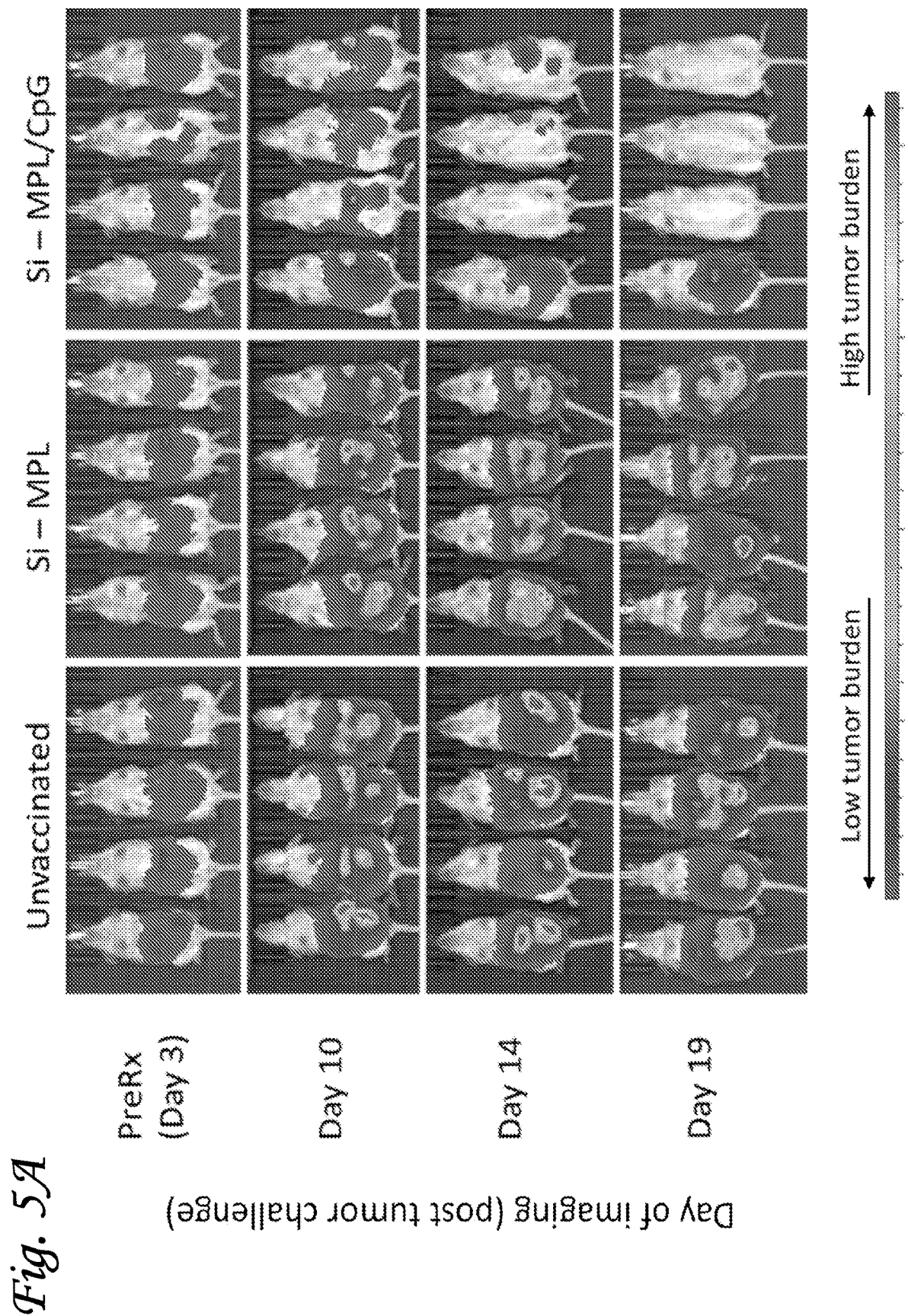
FIG. 5. Vaccination with silicified cells+MPL/CpG clears established tumor in vivo. (A) Heat map of peritoneal tumor burden over time in unvaccinated, Si-MPL vaccinated, and Si-MPL/CpG vaccinated mice as measured by bioluminescence (p/s) with more tumor appearing as red. Image shows vaccination with Si-MPL/CpG cleared intraperitoneal tumor cells in three of four mice by Day 19. (B) The average tumor burden per group over time by bioluminescence (p/s), showing the Si-MPL-CpG group experienced progressive tumor loss after vaccination. Bioluminescence was normalized to Day 3 (pre-treatment control). (C) Analysis of tumor burden by bioluminescence on Day 19, showing Si-MPL/CpG significantly reduced peritoneal tumor burden. (P value: *<0.05, <0.005, *<0.0005).
Figure 5B:
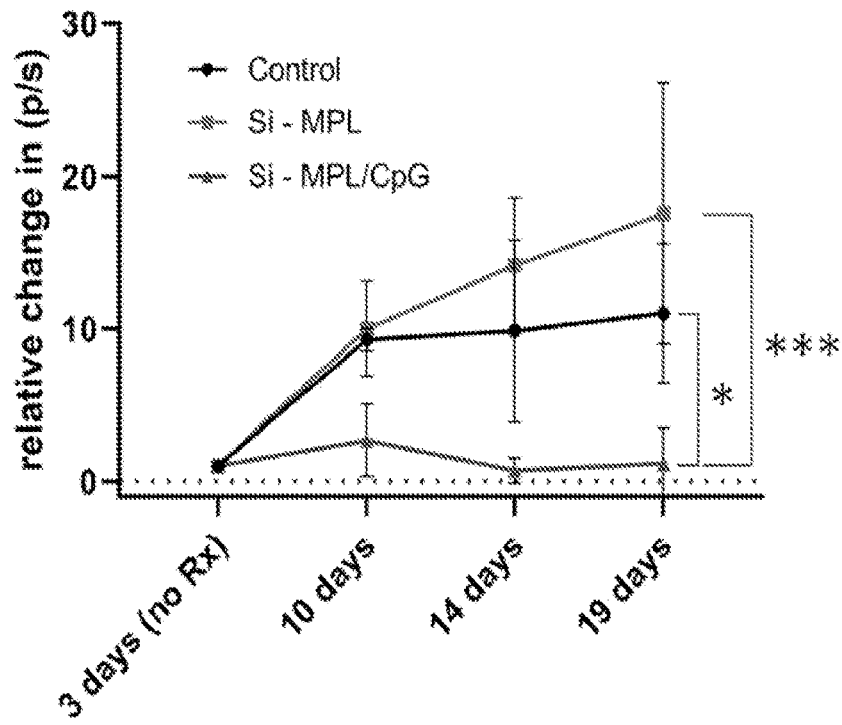
Figure 5C:
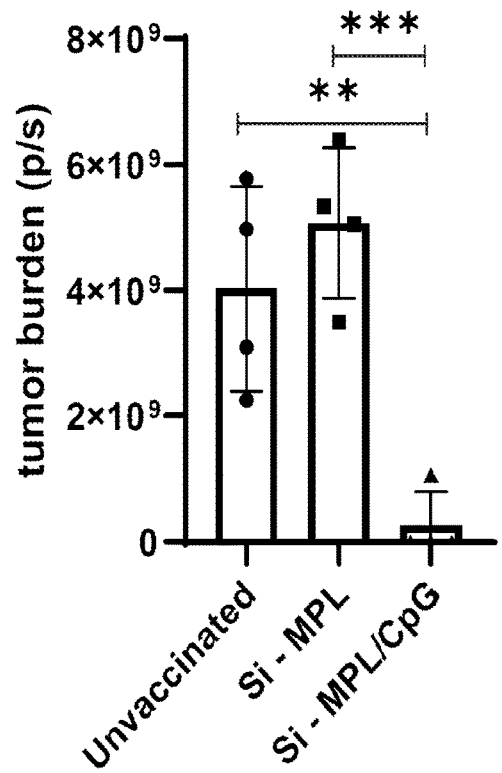

Murine ID8-ova and BR5-AKT ovarian cancer cells were silicified in 100 mM tetramethyl orthosilicate (TMOS) in 1 mM HCl (pH 3), 100 mM NaCl at −80° C. for 24 hours. Since the reaction is self-limiting, longer incubation times are acceptable. Upon thawing, secondary cell surface modification with polyamine enabled strong adsorption of TLR ligand to the cell surface. Effects of vaccination with TLR-ligand-functionalized silicified cells against tumor engraftment in mice challenged with BR5-Akt cancer cells, both at first exposure (Day 0) and again when re-challenged 27 days later are shown in FIG. 4B and FIG. 4C. While MPL-coated Si-cells were able to reduce tumor engraftment (prophylactic injection), addition of other immunogenic ligands (e.g., CpG) improved the treatment of established tumors (therapeutic vaccination). While MPL-coated Si-cells were able to reduce tumor engraftment (prophylactic injection), addition of other immunogenic ligands (e.g., CpG) improved the treatment of established tumors (therapeutic vaccination). Unvaccinated control mice began to gain weight near Day 16 (FIG. 4B), with average weight by group shown for Day 25 (FIG. 4C). Survival of untreated and vaccinated mice is shown in FIG. 4D, with all mice in the vaccinated groups surviving.

Ovarian Cancer Tumor Model

The benefit of treating tumor-bearing mice was tested with silicified BR5-Akt cells coated with either monophosphoryl lipid A (MPL) or MPL+CpG. BALB/c mice were vaccinated with silicified BR5-Akt cells (3×10$^6$ intraperitoneally) coated with MPL or MPL/CpG at four days, six days, 11 days, and 17 days after intraperitoneal tumor challenge (2×10$^5$ ip BR5-Akt-luciferase2+ cells). Tumor burden was monitored before treatment on day 3 and after treatment on day 10, day 14, and day 19 using bioluminescence quantification on an in vitro imaging system (IVIS, PerkinElmer, Inc., Waltham, MA). On day 20, all mice were sacrificed, and peritoneal wash and splenic tissues were collected for analysis using flow cytometry. Enhanced anti-tumor immunity was tested by screening for functional effector T cells based on their phenotype ($CD44^+CD62L^-$) and capacity to produce IFN-γ. Changes in local regulatory subsets, including $CD4^+FoxP3^+$ Treg cells and myeloid derived suppressor cells, were analyzed to test a mechanism of anti-tumor immunity.

Example 2

Materials

Low molecular weight chitosan, poly-L-lysine, puromycin dihydrochloride, rhodamine B isothiocyanate mixed isomers, and 10% buffered formalin, were purchased from Sigma-Aldrich (St. Louis, MO). PROLONG Gold Antifade Mountant with DAPI, Alexa Fluor 488 alpha tubulin antibody phosphate-buffered saline (PBS) and RPMI 1640 were purchased from Thermo Fisher Scientific (Waltham, MA). Fetal bovine serum (FBS) was purchased from ATCC (Manassas, VA). 0.05% EDTA trypsin solution, penicillin-streptomycin, and rhodamine or Alexa Fluor 647 phalloidin were purchased from Life Technologies Corporation (Carlsbad, CA). Dulbecco's Modified Eagle's Medium (DMEM) was obtained from Caisson Labs (Smithfield, UT). Cell Titer-Glo 2.0 Assay was purchased from Promega (Madison, WI).

Recombinant murine granulocyte macrophage colony stimulating factor (GM-CSF) was purchased from R&D Systems (Minneapolis, MN). XenoLight D-Luciferin Potassium Salt was purchased from Perkin Elmer (Boston, MA). Reversible Strainers (37 µm mesh) were purchased from STEMCELL Technologies (Cambridge, MA).

Antibodies

CD3 (17A2) APC-eFluor 780, CD4 (GK1.5) APC, CD8a (53-6.7) eFluor 450 and Alexa Flour 488, CD11b (M1/70) APC and FITC, CD11c (N418) PerCP-Cyanine5.5 and PECy7, CD40 (3/23) PE, CD44 (IM7) PerCP-Cyanine5.5, CD62L (L-selectin, MEL 14) FITC, CD152 (CTLA-4, UC10-4B9) PE and PerCp-Cy5.5, CD223 (LAG3, C9B7W) PerCP-Cy5.5 BD, CD279 (PD-1, J43) PE-Cyanine7, CD305 (LAIR1; 113) PE, APC-eFluor 780, F4/80 (BM8) Alexa Fluor 488 PE and eFlour 450, and (MF48020) Alexa Flour 488, FOXP3 (FJK-16s) PE, IFN-γ (XMG1.2) Alexa Fluor 488, Ly-6C (HK1.4) eFluor 450 and PerCP-Cy5.5, MHC Class II (I A/I E) (M5/114.15.2) FITC, Pan Cytokeratin (AE1/AE3) eFluor 570, Ly-6G (1A8-Ly6g) APC-eFluor 780, F4/80 (BM8) PE and Alexa Fluor 488, CD305 (LAIR1, 113) PE, CD45R (B220) FITC, Fc receptor blockers (anti-CD16/CD32 (clone 2.4G2)), mouse IgG (31205), and LIVE/DEAD Fixable Aqua Dead Cell Stain Kit for 405 nm excitation were purchased from eBioscience, Inc./Thermo Fisher Scientific (Waltham, MA). CD152 PerCP, TIM3 (B8.2C12) APC, CD103 (2E7) Brilliant Violet 605, and CD69 (H1.2F3) Brilliant Violet 605 were purchased from BioLegend (San Diego, CA).

Cell Lines and Mouse Models of Ovarian Cancer

The BRCA1-deficient BR5-Akt cell line, generated on an FVB background, was previously described (Xing, D. & Orsulic, S., 2006, Cancer Res 66:8949-8953). The ID8ova cell line, generated from C57BL/6 ovarian epithelial cells, and transfected to express ovalbumin constitutively, were previously described (Roby et al., 2000, Carcinogenesis 21:585-591). Both ID8ova and BR5-Akt cell lines are syngeneic models of high-grade serous epithelial ovarian cancer. To monitor tumor burden using a bioluminescent tag, ID8ova and BR5-Akt lines were lentivirus transduced to constitutively express firefly2 luciferase. Cell lines were cultured in DMEM containing 10% FBS and 100 units/100 µg penicillin/streptomycin at 37° C. and 5% $CO_2$.

Trypsin-EDTA was Used to Harvest Cells.

To prepare bone marrow-derived dendritic cells (DC), bone marrow was harvested from the femurs of female murine C57BL/6 or FVB mice using a 27-gauge needle and syringe to flush the marrow from the bone. Bone marrow cells were cultured for 8-10 days in RPMI 1640 medium supplemented with 10% FBS, 100 mM β-mercaptoethanol, penicillin/streptomycin, and 10 ng/ml recombinant murine GM-CSF.

Mice were purchased from Charles River Laboratories (Wilmington, MA) and housed in a specific pathogen-free facility. To generate tumors, $2 \times 10^5$ BR5-Akt-Luc2 cells in 2004, PBS were administered by intraperitoneal (IP) injection into 6-7 week old FVB female mice. Injection concentrations were chosen to give a consistent engraftment and predictable disease progression. Mice were sacrificed when moribund or when weight reached 30 g due to ascites accumulation. Mice were monitored and weighed every 2-3 days. For studies that included subcutaneous (SC) tumors, female mice were injected with 200 µl PBS containing $2 \times 10^5$ BR5-Akt-Luc2 cells on the dorsal surface using isoflurane as an inhalation anesthetic.

Cell Silicification $3 \times 10^6$ BR5-Akt or ID8ova cells were washed with PBS, followed by 154 mM NaCl solution, and then suspended in 1 mL silicic acid solution containing 10 mM tetramethyl orthosilicate (TMOS), 100 mM NaCl and 1.0 mM HCl (pH 3.0), with scale up as needed. Following a 5-10-minute incubation at room temperature, the cell suspension was transferred to −80° C. for 24 hours. Silicified cells were then washed with endotoxin-free water, followed by PBS. To compare Si content with published cell silicification techniques, cells were silicified at room temperature in silicic acid solution containing 100 mM TMOS, 154 mM NaCl and 1.0 mM HCl (pH 3.0) for 24 hours as previously described (Kaehr et al., 2012, Proc Natl Acad Sci USA 109:17336-17341).

Coating Silicified Cells with Cationic Polymer

Silicified cells were made cationic using chitosan, poly-L-lysine or polyethyleneimine (PEI). $3 \times 10^6$ silicified cells were washed with water, followed by PBS, and then suspended in 1 mL of either 0.2 mg/mL PEI or 2 mg/mL chitosan in PBS. Following 10 minutes (or as indicated) of rotation at room temperature, the Si-PEI or Si-Chit cells were washed twice with PBS.

Adsorption of TLR Ligand to Silicified (Si) Cells $12 \times 10^6$ silicified cells, with or without polymer coating, were washed with PBS and then suspended in 25 µL of 1 mg/mL MPL in DMSO. After a 10-minute incubation at room temperature, Si-PEI-MPL or Si-MPL cells (or their chitosan counterparts) were washed with PBS by centrifugation at 2000×g for five minutes followed by suspension in PBS. 1826 oligodeoxynucleotide adsorption followed a similar protocol using 20 µL of 2 mg/mL CpG in endotoxin-free water for every $12 \times 10^6$ silicified cells. For dual adsorption of MPL and CpG, CpG was introduced first for 10 minutes, followed by the addition of MPL for an additional 10 minutes. To evaluate the strength of adjuvant binding, loss during three consecutive PBS washes was quantified using fluorescent TLR ligands and a microplate reader (BioTek Instruments, Inc., Winooski, VT) with excitation/emission at 470/560 nm for PEI-Cy3, and excitation/emission at 488/528 nm for CpG-FITC detection. MPL was quantified by absorption at 290 nm using a ThermoScientific NanoDrop 2000.

Zeta Potential Measurements

Zeta potential measurements were performed using the Malvern Zetasizer Nano-ZS (Westborough, MA) equipped with a He—Ne laser (633 nm) and non-invasive backscatter optics (NIBS). Cells were suspended in 5 mM NaCl solution with measurements performed using the monomodal analysis tool. All reported values correspond to the average of at least three independent samples.

Optical Microscopy

For bright field imaging, BR5-Akt cells at 100,000 cells/mL in the water or PBS were imaged using the Nikon eclipse TS 100 inverted microscope equipped with a Nikon digital-sight DS-L3 camera.

In Vitro DC Internalization of Fluorescent Silicified Cells

To image DC association with silicified cells, BR5-Akt cancer cells were first incubated with fluorescent mesoporous silica nanoparticles labeled with rhodamine B isothiocyanate (RITC) for four hours. Tumor cells were then silicified using optimized conditions and surface-masked with TLR ligands (as indicated). DCs were seeded onto glass coverslips in 6-well plates at a density of $5 \times 10^5$ cells per well and the next day, fluorescent silicified vaccine cells were added and DC were incubated for an additional one hour. DCs were then washed with PBS and fixed with 4% paraformaldehyde for 15 minutes at room temperature followed by overnight incubation at 4° C. The following day, cells were washed with PBS, permeabilized with 0.1% Triton-X in PBS for 15 minutes, blocked with 1% BSA for 20 minutes, and then labeled with Alexa Fluor 647 phalloidin and alpha-tubulin antibody Alexa Fluor 488 (Invitrogen, Carlsbad, CA) in 1% BSA for one hour. After a final wash in PBS, coverslips were mounted on slides using PROLONG Gold with DAPI (Thermo Fisher Scientific, Inc., Waltham, MA). Images were acquired using a 63×/1.4NA oil objective in sequential scanning mode using a confocal microscope (TCS SP8, Leica Microsystems, Wetzlar, Germany).

DC uptake of silicified cells was quantified by flow cytometry. BR5-Akt cells were stained with CELL TRACE Far Red (Thermo Fisher Scientific, Inc., Waltham, MA) prior to silicification. Silicified cells, surface modified with TLR ligands as indicated, were co-cultured with CELL TRACE Violet (Thermo Fisher Scientific, Inc., Waltham, MA)-labeled DCs for 1-4 hours, and then analyzed by flow cytometry for double-positive cell populations.

Scanning Electron Microscopy (SEM) and Energy Dispersive X-Ray (EDX) Analysis

Silicified tumor cells were suspended in 100% ethanol and then dropped onto 5×5 mm glass slides. The glass slides were then mounted on SEM stubs using conductive adhesive tape (12 mm OD PELCO Tabs). SEM and EDX images were acquired under high vacuum at 7.5 k using a FEI Quanta 3D Dualbeam FIB-FEGSEM with EDAX SDD EDS detector (Thermo Fisher Scientific, Inc., Waltham, MA).

Inductively Coupled Plasma-Optical Emission Spectroscopy (ICP-OES)

ICP-OES was used to measure Si concentration in silicified cells. The cells were dried under vacuum for seven days and then mineralized in aqua regia (1:3 mixture of ultrapure $HNO_3$ and HCl) with a Digi prep MS SCP Science block digester at 95° C. for four hours. The digested samples were diluted and passed through 0.45 μm filter. The concentration of Si was then measured using an OPTIMA 5300DV ICP-OES (PerkinElmer, Inc., Waltham, MA), with a detection limit of <0.5 mg/L. ICP-OES is calibrated with a five-point calibration curve. QA/QC measurements were also obtained to ensure quality results.

Proliferation Assays

Native and silicified cells, with or without PEI coating, were assessed for cell growth using the CELLTITER-GLO 2.0 assay (Promega Corp., Madison, WI). Briefly, cells were seeded at a density of 100,000 cells/mL in culture media in white opaque 96-well plates. After 24 hours, CELLTITER-GLO 2.0 reagent (Promega Corp., Madison, WI) was added to each well and incubated for 10 minutes. Luminescence was determined using a microplate reader (BioTek Instruments, Inc., Winooski, VT). To assess the impact of silicified cells on the growth of live cancer or dendritic cells, attached cells were incubated with increasing concentrations of silicified cells for 24 or 72 hours, and cell growth was evaluated as stated above. Percent cell viability was calculated relative to control, non-treated cells.

Preparation of Mesoporous Silica Nanoparticles (MSN)

A mixture of water (100 mL), ethanol (40 mL), sodium hydroxide (NaOH, 2M, 0.75 mL) and cetyltrimethylammonium bromide (CTAB, 0.640 g) was heated to 70° C. under vigorous stirring (750 rpm) in a round bottom flask immersed in an oil bath. Afterwards, tetraethyl orthosilicate (TEOS, 1 mL) was added dropwise to the solution. The TEOS was allowed to undergo a series of hydrolysis condensation reactions for two hours to yield silica CTAB-templated silica nanoparticles. The particles were then isolated by centrifugation (2000×g, 20 minutes) and then washed with MeOH three times. The surfactant removal was performed by suspending the nanoparticles in a solution of 0.45 g/L ammonium nitrate in ethanol and stirring at 60° C. for 20 minutes. Finally, the template-free MSN were consecutively washed twice with water and ethanol and stored suspended in ethanol. MSN (0.5 mg) were rinsed twice with water and then suspended in 1 mL of 0.2 mg/mL PEI in PBS solution. After 10 minutes rotation at room temperature to allow PEI binding on the MSN surface, the MSN with PEI coating (MSN-PEI) were then rinsed with PBS twice. MSN-PEI (0.5 mg) were suspended in 20 μL of 2 mg/mL CpG in double distilled water solution. After a 10-minute incubation at room temperature, 25 μL of 1 mg/mL MPL in DMSO solution was added and incubated another 10 minutes. MSN-PEI-CpG-MPL particles were then centrifuge at 20,000 rcf for five minutes to remove extra free ligand, and then resuspended and stored in 0.5 mL PBS.

In Vitro DC Functional Studies

DCs were seeded in 12-well plates at a density of $1\times10^5$ cells per well. After 24 hours, the media was removed and replaced with 2 mL of fresh complete media supplemented with 100,000 Si-PEI-CpG-MPL (or irradiated PEI-CpG-MPL) ID8ova cells for 72 hours. DCs were collected using 3 mM EDTA. The suspended cells were centrifuged, washed with PBS containing 1% BSA, and labeled with fluorescent antibodies specific for CD11c and either co-stimulatory molecules or SIINFEKL-H2-$k^b$. Cells were analyzed by flow cytometry.

Vaccination of Mice with Si-Tumor Cells

Female FVB mice were vaccinated intraperitoneally with silicified BR5-Akt (or BR5-Akt-Luc2 for viability studies) cells (with TLR ligands as indicated) using doses of $3\times10^4$, $3\times10^5$, $3\times10^6$, or $3\times10^7$ cells/mouse in 200 μl of PBS at the indicated schedules. Alternatively, mice were vaccinated subcutaneously (SC) with $3\times10^6$ Si-cells by scruffing the skin at the back of their neck and injecting into the loose fold of skin. Mice that cleared all tumor cells based on IVIS Spectrum bioluminescent imaging were re-challenged at a later date, as indicated for each study. All control (no Tx) mice received sham PBS injections (200 μl/mouse).

Preparation of Ascites-Derived Tumor Vaccines

To prepare vaccine using murine tumor (ascites) cells, peritoneal fluid was collected from mice with late-stage BR5-Akt cancer. The intact peritoneal cavity was exposed and ascites, as well as two peritoneal wash samples with cold PBS, were collected using an 18-gauge needle and 5 mL syringe inserted in the hypogastric region and positioned towards the cecum. In addition, ascites fluid or peritoneal washing samples were collected from patients with a diagnosis of ovarian cancer at the time of surgical debulking in accordance with approved IRB Protocol #UNM INST 1509, entitled "Single Institution (UNM) Prospective Laboratory Study of Cancer and Immune Cells in the Ascites Fluid of Ovarian Cancer Patients to Test Alternative Therapies." Human specimens were de-identified prior to transfer for research purposes. To isolate peritoneal cells, ascites were centrifuged at 1400 RPM for five minutes, after which the supernatant was removed, and RBCs were removed using ACK lysis buffer. Tumor cells were enriched using a 37-μm reversible strainer. Solid murine tumor tissue was enzymatically and mechanically dissociated. EpCAM$^+$ and CD45$^+$ populations were evaluated by flow cytometry. Cells were then silicified and surface modified as previously described.

Imaging Tumor Burden

For in vivo monitoring of tumor burden, mice with BR5-Akt-Luc2 tumors were administered 150 mg luciferin/kg by intraperitoneal injection. Mice were then anesthetized using 2.5% isoflurane, and 2D bioluminescence images were acquired using the XENOGEN IVIS Spectrum animal imager (PerkinElmer, Inc., Waltham, MA). ROI measurements of total flux (photons/sec) were acquired using LIVING IMAGE software (Perkin Elmer, Inc., Waltham, MA).

Murine Tissue/Cell Collection

All mice were euthanized in accordance with Institutional Animal Care and Use Committee (IACUC) at the University of New Mexico (Albuquerque NM). Spleens were mechanically dissociated, and RBC were eliminated using ACK or BD Pharm Lyse. Blood was collected retro-orbitally with EDTA or heparin. Omentum, peritoneal tumor, lungs, gut, brain, and kidneys were dissected out and fixed in 10% buffered formalin. Tissues were embedded in paraffin, sectioned and stained with H&E by the University of New Mexico Health Science Center Histology and Molecular Pathology Shared Resource.

Immune Cell Phenotyping

Single-cell suspensions were first blocked with Fc receptor blockers (1 µg anti-CD16/CD32 (clone 2.4G2) and 1 µg mouse IgG. Next, samples were surface stained with conjugated primary antibodies at room temperature for 30 minutes in the dark. Samples were then stained with LIVE/DEAD Fixable Aqua Dead Cell Stain (eBioscience, Inc./Thermo Fisher Scientific, Inc., Waltham, MA) for 15 minutes at room temperature in the dark. For intracellular cytokine analysis, cells were stimulated using Cell Stimulation Cocktail (plus protein transport inhibitors, 500×; eBioscience, Inc./Thermo Fisher Scientific, Inc., Waltham, MA) for four hours in RMPI complete media. Cell permeabilization for intracellular staining was done using the FoxP3/Transcription Factor Staining Buffer Set (eBioscience, Inc./Thermo Fisher Scientific, Inc., Waltham, MA). Phenotyping was performed on stained cells by flow cytometry.

Blood Metabolite Measurements

Blood metabolites and complete blood counts were measured on Day 18 or Day 19 using the Vetscan VS2 analyzer and comprehensive or partial diagnostic profile discs (Abaxis, Union City, CA) as described by the vendor.

Statistical Analysis

PRISM software (GraphPad Software, San Diego, CA) was used for all statistical analysis. Log-rank (Mantel-Cox) and Gehan-Breslow-Wilcoxon tests were used for two curve comparisons presented in Kaplan-Meier survival curves. Unpaired, parametric, two-tail t tests assumed populations had the same standard deviation.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

SEQUENCE LISTING FREE TEXT

SEQ ID NO: 1
SIINFEKL

What is claimed is:

1. A pharmaceutical composition comprising:
a silicified cell, a silicified cell-derived body, or a silicified vesicle, the silicified cell, silicified cell-derived body, or silicified vesicle comprising a silicified surface;
a cationic layer disposed on at least a portion of the silicified surface; and
an immunomodulatory moiety bound to at least a portion of the cationic layer.

2. The pharmaceutical composition of claim 1, wherein the immunomodulatory moiety comprises a pathogen-associated molecular pattern (PAMP), a danger-associated molecular molecule (DAMP), a cytokine, an antibody, or other immunogenic entity.

3. The pharmaceutical composition of claim 2, wherein the PAMP comprises lipopolysaccharide (LPS), monophosphoryl lipid A (MPL), CpG, R-848, or PolyIC.

4. A method of inducing an immune response against a silicified cell, a silicified cell-derived body, or a silicified vesicle, the method comprising:
providing the pharmaceutical composition of claim 1; and
administering the pharmaceutical composition to a subject in an amount effective to induce the subject to produce an immune response directed against the silicified cell, silicified cell-derived body, or silicified vesicle in the pharmaceutical composition.

5. The method of claim 4, wherein the pharmaceutical composition is administered to the subject in a composition that comprises an effective amount of a pharmaceutically acceptable adjuvant.

6. The method of claim 4, wherein the pharmaceutical composition is administered to the subject in a composition that includes an agent that blocks immune suppression.

7. The method of claim 6, wherein the agent that blocks immune suppression comprises an anti-TGF-β antibody or an anti-IL-10 antibody.

8. The method of claim 6, wherein the agent that blocks immune suppression comprises an immune checkpoint inhibitor.

9. The method of claim 8, wherein the immune checkpoint inhibitor comprises an anti-PD-1 antibody, an anti-PD-L1 antibody, an anti-TIM3 antibody, or an anti-CTLA-4 antibody.

10. A method for treating a subject having, or at risk of having, a tumor, the method comprising:
providing a silicified tumor cell comprising:
a silicified surface;
a cationic layer disposed on at least a portion of the silicified surface of the silicified tumor cell; and
an immunomodulatory moiety bound to at least a portion of the cationic layer; and
administering the silicified tumor cell to the subject in an amount effective to ameliorate at least one symptom or clinical sign of having the tumor.

11. The method of claim 10, wherein the tumor cell is an autologous cancer cell obtained from the subject.

12. The method of claim 10, wherein the tumor cell is an allogenic cancer cell obtained from a second subject.

13. The method of claim 10, wherein the silicified cell is administered to the subject in a composition that comprises an effective amount of a pharmaceutically acceptable adjuvant.

14. The method of claim 11, wherein the tumor cell is obtained from fluid from the subject's peritoneal cavity.

15. The method of claim 11, wherein the tumor cell is obtained from a solid tumor, at least a portion of which is removed from the subject.

* * * * *